(12) United States Patent
Shaw et al.

(10) Patent No.: US 8,318,451 B2
(45) Date of Patent: Nov. 27, 2012

(54) **PROCESS OF OBTAINING ETHANOL WITHOUT GLUCOAMYLASE USING *PSEUDOMONAS SACCHAROPHILA* G4-AMYLASE VARIANTS THEREOF**

(75) Inventors: Andrew Shaw, San Francisco, CA (US); Regina Chin, Palo Alto, CA (US); Karsten M. Kragh, Viby J (DK)

(73) Assignee: Danisco US Inc., Palo Alto, CA (US)

( * ) Notice: Subject to any disclaimer, the term of this patent is extended or adjusted under 35 U.S.C. 154(b) by 803 days.

(21) Appl. No.: 12/318,513

(22) Filed: Dec. 30, 2008

(65) Prior Publication Data

US 2009/0311764 A1 Dec. 17, 2009

Related U.S. Application Data

(60) Provisional application No. 61/006,240, filed on Jan. 2, 2008.

(51) Int. Cl.
- *C12Q 1/40* (2006.01)
- *C12N 9/26* (2006.01)
- *C12N 9/28* (2006.01)
- *C07K 14/00* (2006.01)
- *C12P 21/00* (2006.01)

(52) U.S. Cl. ......... 435/22; 435/202; 435/69.1; 435/201; 530/350

(58) Field of Classification Search .................. 435/201, 435/202, 22, 69.1; 530/350
See application file for complete search history.

(56) References Cited

U.S. PATENT DOCUMENTS

| | | | |
|---|---|---|---|
| 5,874,276 | A | 2/1999 | Fowler et al. |
| 6,022,725 | A | 2/2000 | Fowler et al. |
| 6,077,316 | A | 6/2000 | Lund et al. |
| 6,268,328 | B1 | 7/2001 | Mitchinson et al. |
| 6,667,065 | B1 | 12/2003 | Kragh et al. |
| 6,890,572 | B2 | 5/2005 | Kragh et al. |
| 7,166,453 | B2 | 1/2007 | Kragh et al. |
| 7,371,552 | B2 | 5/2008 | Kragh et al. |
| 7,638,299 | B2 | 12/2009 | Cho et al. |
| 8,030,050 | B2 | 10/2011 | Berg et al. |
| 2005/0136524 | A1 | 6/2005 | Kragh et al. |
| 2005/0137111 | A1 | 6/2005 | Kragh et al. |
| 2006/0008888 | A1 | 1/2006 | Kragh et al. |
| 2006/0008890 | A1 | 1/2006 | Kragh et al. |
| 2006/0018997 | A1 | 1/2006 | Kragh et al. |
| 2006/0019347 | A1 | 1/2006 | Cho et al. |
| 2006/0073583 | A1 | 4/2006 | Kragh et al. |
| 2007/0020727 | A1 | 1/2007 | Berg et al. |
| 2007/0020731 | A1 | 1/2007 | Kragh et al. |
| 2007/0072270 | A1 | 3/2007 | Kragh et al. |
| 2007/0141693 | A1 | 6/2007 | Berg et al. |
| 2008/0107773 | A1 | 5/2008 | Kragh et al. |
| 2008/0274531 | A1 | 11/2008 | Berg et al. |
| 2009/0202675 | A1 | 8/2009 | Derkx et al. |
| 2009/0214706 | A1 | 8/2009 | Berg et al. |
| 2011/0212241 | A1 | 9/2011 | Kragh et al. |

FOREIGN PATENT DOCUMENTS

| | | |
|---|---|---|
| EP | 0 214 761 | 3/1987 |
| EP | 0 215 594 A2 | 3/1987 |
| EP | 0 238 023 | 9/1987 |
| EP | 0 244 234 A2 | 11/1987 |
| EP | 0 305 216 | 3/1989 |
| IE | 1991/1797 | 12/1991 |
| WO | WO88/02775 | 4/1988 |
| WO | WO89/01032 | 2/1989 |
| WO | WO91/04669 | 4/1991 |
| WO | WO91/19782 | 12/1991 |
| WO | WO92/01793 | 2/1992 |
| WO | WO92/17573 | 10/1992 |
| WO | WO95/00636 | 1/1995 |
| WO | WO 02/068589 | 9/2002 |
| WO | WO 2004/091544 | 10/2004 |
| WO | WO 2004/111217 | 12/2004 |
| WO | WO 2004/111218 A | 12/2004 |
| WO | WO2005/000339 | 1/2005 |
| WO | WO 2005/003339 A | 1/2005 |
| WO | WO 2005/007867 | 1/2005 |
| WO | WO 2006/003461 | 1/2006 |
| WO | WO 2007/007053 A | 1/2007 |
| WO | WO 2007/148224 A | 12/2007 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al. , J. Bacteriol. 183(8):2405-2410, 2001.*
Altschul, S.F. et al. "Local alignment statistics." *Methods Enzymol* 266:460-80, 1996.
Altschul, S.F. et al. "Basic local alignment search tool." *J. Mol. Biol* 215(3):403-410, 1990.
Campbell, E.I. et al. "Improved transformation efficiency of *Aspergillus niger* using the homologous niaD gene for nitrate reductase." *Current Genetics* 16(1):53-56, 1989.
CCP4. "The CCP4 suite: programs for protein crystallography." *Acta Crystallographica Section D Biological Crystallography* 50(5):760-763, 1994.
Database GenBank. "*P. saccharophila* mta gene encoding maltotetraohydrolase (EC number=3.2.1.60)," Accession No. X16732, Apr. 18, 2005.
Davies, G.J. et al. "Nomenclature for sugar-binding subsites in glycosyl hydrolases.." *Biochemical Journal* 321(Pt 2):557-559, 1997.
Devereux, P. et al. "A comprehensive set of sequence analysis programs for the VAX." *Nucl. Acids Res* 12:387-395, 1984.

(Continued)

*Primary Examiner* — Delia Ramirez
(74) *Attorney, Agent, or Firm* — Danisco US Inc.

(57) ABSTRACT

*Pseudomonas saccharophila* G4-forming amylase (PS4), and variants thereof, advantageously can be used in an enzyme-catalyzed high temperature liquefaction step to produce ethanol from starch, e.g., cornstarch. PS4 produces significant amounts of maltotrioses, which can be utilized by *S. cerevisiae* in a subsequent fermentation step to produce ethanol. This property of PS4 advantageously allows ethanol to be produced from liquefacted starch in the absence of a saccharification step. PS4 variants are provided that exhibit improved properties, such as thermostability and/or altered exo-specific and endo-specific amylase activity.

18 Claims, 8 Drawing Sheets

OTHER PUBLICATIONS

Dietvorst, J. et al. "Attachment of <I>MAL32</I>-encoded maltase on the outside of yeast cells improves maltotriose utilization." *Yeast* 24(1):27-38, 2007.

Dietvorst, J. et al. "Maltotriose utilization in lager yeast strains: <I>MTT1</I> encodes a maltotriose transporter." *Yeast* 22(10):775-788, 2005.

Harkki, A. et al. "Genetic engineering of Trichoderma to produce strains with novel cellulase profiles." *Enzyme Microb. Technol* 13(3):227-33, 1991.

Harkki, A. et al. "A Novel Fungal Expression System: Secretion of Active Calf Chymosin from the Filamentous Fungus *Trichoderma reesei*." *Bio/Technology* 7(6):596-603, 1989.

Hasegawa, K. et al. "Roles of catalytic residues in alpha-amylases as evidenced by the structures of the product-complexed mutants of a maltotetraose-forming amylase." *Protein Eng.* 12(10):819-824, 1999.

van den Hondel, C. et al. "Heterologous gene expression in filamentous fungi." In *More Gene Manipulations in Fungi*, eds. J.W. Bennett et al. San Diego, CA: Academic Press, pp. 396-428, 1991.

Karlin, S. et al. "Applications and statistics for multiple high-scoring segments in molecular sequences." *Proc. Natl. Acad. Sci. USA* 90(12):5873-7, 1993.

Kelly, J.M. et al. "Transformation of *Aspergillus niger* by the amdS gene of *Aspergillus nidulans*." *The EMBO Journal* 4(2):475-479, 1985.

Needleman, S.B. et al. "A general method applicable to the search for similarities in the amino acid sequence of two proteins." *J. Mol. Biol* 48(3):443-53, 1970.

Pearson, W.R. et al. "Improved Tools for Biological Sequence Comparison." *Proc. Natl. Acad. Sci. USA* 85(8):2444-2448, 1988.

Penttilä, M. et al. "A versatile transformation system for the cellulolytic filamentous fungus *Trichoderma reesei*." *Gene* 61(2):155-64, 1987.

Smith, H. et al. "Characterization of signal-sequence-coding regions selected from the *Bacillus subtilis* chromosome." *Gene* 70(2):351-361, 1988.

Smith, T.F. et al. "Comparison of biosequences." *Adv. Appl. Math* 2:482-489, 1981.

Stambuk, B.U. et al. "Improvement of maltotriose fermentation by *Saccharomyces cerevisiae*." *Letters in Applied Microbiology* 43(4):370-376, 2006.

Yoon, S.-H. et al. "Specificity of yeast (*Saccharomyces cerevisiae*) in removing carbohydrates by fermentation." *Carbohydrate Research* 338(10):1127-1132, 2003.

Yoshioka, Y. et al. "Crystal structures of a mutant maltotetraose-forming exo-amylase cocrystallized with maltopentaose." *Journal of Molecular Biology* 271(4):619-628, 1997.

Zhou, J.H. et al. "Nucleotide sequence of the maltotetraohydrolase gene from *Pseudomonas saccharophila*." *FEBS Letters* 255(1):37-41, 1989.

International Search Report for PCT/US2008/014105, mailed Jun. 29, 2009.

Christophersen, C., et al., "Enzymatic Characterisation of Novamyl®, a Thermostable a-Amylase." Starch/Stärke 50: 39-45, 1998.

Feng, D.-F., et al., "Progressive Sequence Alignment as a Prerequisite to Correct Phylogenetic Trees." *J. Mol. Evol.* 25: 351-360, 1987.

Gayle, R.B., et al., "Identification of regions in interleukin-1 alpha important for activity." *J. Biol. Chem.* 268(29): 22105-22111, 1993.

Higggins, D.G., et al., "Fast and sensitive multiple sequence alignments on a microcomputer." *CABIOS Communications* 5(2): 151-153, 1989.

Whisstock, J.C., et al., "Prediction of protein function from protein sequences and structure." *Q. Rev. Biophys.* 36(3): 307-340, 2003.

\* cited by examiner

SEQUENCE LISTING

<160> NUMBER OF SEQ ID NOS: 45

<210> SEQ ID NO 1
<211> LENGTH: 530
<212> TYPE: PRT
<213> ORGANISM: Pseudomonas saccharophila

<400> SEQUENCE: 1

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Asn Asp Trp Tyr Asn Ile Leu Arg Gln Gln Ala Ser Thr Ile Ala Ala
            35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

```
Val Val Pro Asn His Met Asn Arg Gly Tyr Pro Asp Lys Glu Ile Asn
        115                 120                 125
Leu Pro Ala Gly Gln Gly Phe Trp Arg Asn Asp Cys Ala Asp Pro Gly
    130                 135                 140
Asn Tyr Pro Asn Asp Cys Asp Gly Asp Arg Phe Ile Gly Gly Glu
145                 150                 155                 160
Ser Asp Leu Asn Thr Gly His Pro Gln Ile Tyr Gly Met Phe Arg Asp
                165                 170                 175
Glu Leu Ala Asn Leu Arg Ser Gly Tyr Gly Ala Gly Gly Phe Arg Phe
                180                 185                 190
Asp Phe Val Arg Gly Tyr Ala Pro Glu Arg Val Asp Ser Trp Met Ser
        195                 200                 205
Asp Ser Ala Asp Ser Ser Phe Cys Val Gly Leu Trp Lys Gly Pro
    210                 215                 220
Ser Glu Tyr Pro Ser Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
    290                 295                 300
Gln His His Trp Ala Leu Gln Asp Gly Leu Ile Arg Gln Ala Tyr Ala
305                 310                 315                 320
Tyr Ile Leu Thr Ser Pro Gly Thr Pro Val Val Tyr Trp Ser His Met
                325                 330                 335
Tyr Asp Trp Gly Tyr Gly Asp Phe Ile Arg Gln Leu Ile Gln Val Arg
            340                 345                 350
Arg Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
    370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Gly Asn Asp Gly Gly Glu Gly Gly
            420                 425                 430
Leu Val Asn Val Asn Phe Arg Cys Asp Asn Gly Val Thr Gln Met Gly
        435                 440                 445
Asp Ser Val Tyr Ala Val Gly Asn Val Ser Gln Leu Gly Asn Trp Ser
    450                 455                 460
Pro Ala Ser Ala Val Arg Leu Thr Asp Thr Ser Ser Tyr Pro Thr Trp
465                 470                 475                 480
Lys Gly Ser Ile Ala Leu Pro Asp Gly Gln Asn Val Glu Trp Lys Cys
                485                 490                 495
Leu Ile Arg Asn Glu Ala Asp Ala Thr Leu Val Arg Gln Trp Gln Ser
            500                 505                 510
Gly Gly Asn Asn Gln Val Gln Ala Ala Gly Ala Ser Thr Ser Gly
        515                 520                 525

Ser Phe
```

<210> SEQ ID NO 2
<211> LENGTH: 418
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly

-continued

```
                355                 360                 365
Tyr Ser Gly Leu Val Ala Thr Val Ser Gly Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser

<210> SEQ ID NO 3
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Pro Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300
```

```
Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser

<210> SEQ ID NO 4
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Asn Asp Trp Tyr Asn Ile Leu Arg Gln Gln Ala Ser Thr Ile Ala Ala
            35                  40                  45

Asp Gly Phe Ser Ala Ile Trp Met Pro Val Pro Trp Arg Asp Phe Ser
        50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Pro Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240
```

```
Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser

<210> SEQ ID NO 5
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
```

```
                180                 185                 190
Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Ala Pro
        210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
        290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
        370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser

<210> SEQ ID NO 6
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Arg Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125
```

Leu Pro Ala Gly Gln Arg Phe Trp Arg Asn Asp Cys Pro Asp Pro Gly
    130                 135                 140

Asn Tyr Pro Asn Asp Cys Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
                180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
                340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser

<210> SEQ ID NO 7
<211> LENGTH: 3050
<212> TYPE: DNA
<213> ORGANISM: Pseudomonas saccharophila

<400> SEQUENCE: 7
gatcggcgta ggtttcgcat tcgttgccca ggcgatattt cgccggtgcg ccagcagcct      60
ggaagcaggc ctggtcgccg ccgccggccg tggcgccgac gcccgaacgc agatagccgt     120
ggaaatcgac cgccagggcc gggccgccga ccagcagggc ggcaagcagg caggcgggtt     180
ttaggacgaa caggggggtgc gcggtgtgct tcatgacgag gtccttgttt ttcttgttaa     240
tgccgaatcg atcacgcctt cgctgcgtgt cgcaggcgc agctcggtgg cgaaagcctc      300
ggggatggct ccgctggcgg catcctcccg accagagatt cgctggcgc agctcgaggg      360 cgtaatcaga tgagtgcgg cgtaatccct ggggtgggc tacgcccggc agggcgcaga      420
tgattgccag gggccttcgg cctggccact acgccgcctg caactgggcg gggaggttg      480

```
gtggtcgggg cgtgcagggg cagcctgcgg gtgccggtcg aagacccggc cggcgttcat    540
cctcgtccgg cggccttgcc gtaggatacc cgaacaagca caagaaccgg agtattgcga    600
tgagccacat cctgcgtgcc gccgtattgg cggcggtcct gctgccgttt ccgcactgg     660
ccgatcaggc cggcaagagc ccggccgggg tgcgctacca cggcggcgac gaaatcatcc    720
tccagggctt ccactggaac gtcgtccgcg aagcgcccaa cgactggtac aacatcctcc    780
gccaacaggc ctcgacgatc gcggccgacg gcttctcggc aatctggatg ccggtgccct    840
ggcgtgactt ctccagctgg accgacggcg caagtccgg cggcggcgaa ggctacttct     900
ggcacgactt caacaagaac ggccgctacg gcagcgacgc ccagctgcgc caggccgccg    960
gcgcactcgg tggcgccggg gtgaaggtgc tctacgatgt ggtgcccaat cacatgaacc   1020
gcggctaccc ggacaaggag atcaacctgc cggccggcca gggcttctgg cgcaacgact   1080
gcgccgaccc gggcaactac cccaacgact gcgacgacgg tgaccgcttc atcggcggcg   1140
agtcggacct gaacaccggc catccgcaga tttacggcat gtttcgcgac gagcttgcca   1200
acctgcgcag cggctacggc gccggcggct tccgcttcga cttcgttcgc ggctatgcgc   1260
ccgagcgggt cgacagctgg atgagcgaca gcgccgacga cagcttctgc gttggcgagc   1320
tgtggaaagg ccccttctga atatccgagct gggactggcg caacacggcg agctggcagc   1380
agatcatcaa ggactggtcc gaccgggcca agtgccggt gttcgacttc gctctcaagg    1440
agcgcatgca gaacggctcg gtcgccgact ggaagcatgg cctcaatggc aaccccgacc   1500
cgcgctggcg cgaggtggcg gtgaccttcg tcgacaacca cgacaccggc tattcgcccg   1560
ggcagaacgg cggccagcac cactgggcgc tgcaggacgg gctgatccgc caggcctacg   1620
cctacatcct caccagcccg ggcacgccgg tggtgtactg gtcgcacatg tacgactggg   1680
gctacggcga cttcatccgc cagctgatcc aggtgcggcg caccgccggc gtgcgcgccg   1740
attcggcgat cagcttccat agcggctaca gcggtctggt cgctaccgtc agcggcagcc   1800
agcagaccct ggtggtggcg ctcaactccg atctggccaa ccccggccag gttgccagcg   1860
gcagcttcag cgaggcggtc aacgccagca acggccaggt gcgcgtctgg cgcagcggta   1920
gcggcgatgg cggcgggaat gacggcggcg agggtggctt ggtcaatgtg aactttcgct   1980
gcgacaacgg cgtgacgcag atgggcgaca gcgtctacgc ggtgggcaac gtcagccagc   2040
tcggcaactg gagcccggcc tccgcggtac ggctgaccga caccagcagc tatccgacct   2100
ggaagggcag catcgccctg cctgacggtc agaacgtgga atggaagtgc ctgatccgca   2160
acgaggcgga cgcgacgctg gtgcgtcagt ggcaatcggg cggcaacaac caggtccagg   2220
ccgccgccgg cgcgagcacc agcggctcgt tctgacgaca tgcccgcccg gcctcggcta   2280
cgcctacgcc gggcggctcc tcccgaccca gggtgggcag ggaggaggcc ggcgacgggc   2340
cgggccgccg atgctggcac gacaaccata aaagccttcg cgctgcgctg tcgtatcagg   2400
agctgttcat gttggcccag acccgctcga ccccctttcc gcttggcttc ctggcccggc   2460
tgtacctgct gatcgccgca ctggtggcct tgctgatgct ggtagccggc accagcctgg   2520
ttgccatcgg ccgcctgcaa ggcaatgccg agcaaatctc gtcgaccgcg tcgcgtctgc   2580
tggtcagcga gagcttcttc ggtacgttgc agagcctgac gcagaacctg tccgacgccc   2640
tggccgagga ccgcctgac cagctcgacg gctatgtcgg ccggcatcgc acgctgcagg    2700
accaggccct cgagctgttc gcccagctgg agcgggtgac gccggcacat gccgagacca   2760
agcaagcctg gcgcgctgt tgccggagct cgaccgccgc agcctggcgc tgatcgatgc    2820
gcacgcgacc tgctcgcgcg tggggcgcaa cgccgtcgcc tgcgcgatct gcagctgcag   2880
```

```
ttctcgcggc tcaagcagga cctgctgcag gcgcagttcg tgacgggcga cgagctggtc    2940
gcctattcca tcaagcagtt catcatcccg ctcgagcagg tcgagcgctg ctgttcgatg    3000
ccatcggcgt gtcttcgatc aaggcactcg atgaagcggg tgcgcagatc              3050
```

<210> SEQ ID NO 8
<211> LENGTH: 21
<212> TYPE: PRT
<213> ORGANISM: Pseudomonas saccharophila

<400> SEQUENCE: 8

```
Met Ser His Ile Leu Arg Ala Ala Val Leu Ala Ala Val Leu Leu Pro
1               5                   10                  15

Phe Pro Ala Leu Ala
            20
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gcgaagcgcc ctacaactgg tacaac                                          26
```

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
ctggacggat ggagataaaa gcggaggcgg c                                    31
```

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
ccaatcacat gaaccgcttc tacccggaca aggag                                35
```

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
ctgccggccg gccagcgctt ctggcg                                          26
```

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cgccagaagc gctggccggc cggcag                                       26

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcaacgact gcgccgaccc ggg                                          23

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatccgggca acggccccaa cgactgcg                                     28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacggtgacc gcttcctggg cggcgagtcg                                   30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgactcgccg cccaggaagc ggtcaccgtc                                   30

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggcggcgag gcggacctga aca                                          23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 19
cgcgacgagt ttaccaacct gcg                                           23

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, g, t, unknown or other

<400> SEQUENCE: 20
ggcgagctgt ggaaagdncc ttctgaatat ccgag                              35

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gccttctgaa tatccgccgt gggactggcg caac                               34

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaaatgaag gacaacataa atggccgctt caagatggcc                         40

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcacctgtgg ccgctgcagg acg                                           23

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtactggccg cacatgtacg actggggcta cggcgaattc atc                     43

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 25
gatgaattcg ccgtagcccc agtcgtacat gtgcggccag tac        43

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggctacggc gacttcatcc gccag        25

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgtcggcgaa ctttggaaag caccgagcga atatccgc        38

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cggcgaactt tggaaaggac cgagcgaata tccg        34

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgtcggcgaa ctttggaaaa gcccgagcga atatccgc        38

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggcgaacttt ggaaaaaacc gagcgaatat ccgcc        35

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
cgtcggcgaa ctttggaaaa tcccgagcga atatccgc                                    38

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgtcggcgaa ctttggaaac tgccgagcga atatccgc                                    38

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggcgaacttt ggaaagtccc gagcgaatat ccgcc                                       35

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgtcggcgaa ctttggaaat tccgagcga atatccgc                                     38

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgtcggcgaa ctttggaaat gcccgagcga atatccgc                                    38

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggcgaacttt ggaaaccgcc gagcgaatat ccgcc                                       35

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
```

```
cgtcggcgaa ctttggaaaa cgccgagcga atatccgc                              38
```

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
cgtcggcgaa ctttggaaat atccgagcga atatccgc                              38
```

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
cgtcggcgaa ctttggaaat ggccgagcga atatccgc                              38
```

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
ggcgaacttt ggaaacagcc gagcgaatat ccgcc                                 35
```

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
ggcgaacttt ggaaaaaccc gagcgaatat ccgcc                                 35
```

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
cggcgaactt tggaaagatc cgagcgaata tccg                                  34
```

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
ggcgaacttt ggaaacatcc gagcgaatat ccgcc                                 35
```

```
<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggcgaacttt ggaaaagacc gagcgaatat ccgcc                                  35

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgtcggcgaa ctttggaaaa tgccgagcga atatccgc                               38
```

US 8,318,451 B2

PROCESS OF OBTAINING ETHANOL WITHOUT GLUCOAMYLASE USING *PSEUDOMONAS SACCHAROPHILA* G4-AMYLASE VARIANTS THEREOF

CROSS REFERENCE TO RELATED APPLICATION

This application claims benefit to U.S. Provisional Application No. 61/006,240 filed Jan. 2, 2008, which is incorporated herein in its entirety.

SEQUENCE LISTING

A Sequence Listing, comprising SEQ ID NOS: 1-45, is attached and is incorporated by reference in its entirety.

FIELD OF THE INVENTION

An α-amylase from *Pseudomonas saccharophila*, thermostable mutations thereof, and nucleic acids encoding the same are useful in a process of liquefaction and saccharification of corn syrup to make ethanol, among other things.

BACKGROUND

The conversion of vegetable starches, especially cornstarch, to ethanol is a rapidly expanding industry. The current process consists of two sequential enzyme-catalyzed steps that result in the production of glucose. Yeast can then be used to ferment the glucose to ethanol.

The first enzyme-catalyzed step is starch liquefaction. Typically, a starch suspension is gelatinized by rapid heating to 85° C. or more. α-Amylases (EC 3.2.1.1) are used to degrade the viscous liquefact to maltodextrins. α-amylases are endohydrolases that catalyze the random cleavage of internal α-1,4-D-glucosidic bonds. As α-amylases break down the starch, the viscosity decreases. Because liquefaction typically is conducted at high temperatures, thermostable α-amylases, such as an α-amylase from *Bacillus* sp., are preferred for this step.

The maltodextrins produced in this manner generally cannot be fermented by yeast to form alcohol. A second enzyme-catalyzed saccharification step thus is required to break down the maltodextrins. Glucoamylases and/or maltogenic α-amylases commonly are used to catalyze the hydrolysis of non-reducing ends of the maltodextrins formed after liquefaction, releasing D-glucose, maltose and isomaltose. Debranching enzymes, such as pullulanases, can be used to aid saccharification. Saccharification typically takes place under acidic conditions at elevated temperatures, e.g., 60° C., pH 4.3.

One of the yeasts used to produce ethanol is *Saccharomyces cerevisiae*. *S. cerevisiae* contains α-glucosidase that has been shown to utilize mono-, di-, and tri-saccharides as substrates. Yoon et al., *Carbohydrate Res.* 338: 1127-32 (2003). The ability of *S. cerevisiae* to utilize tri-saccharides can be improved by $Mg^{2+}$ supplementation and over-expression of AGT1 permease (Stambuck et al., *Lett. Appl. Microbiol.* 43: 370-76 (2006)), over-expression of MTT1 and MTT1alt to increase maltotriose uptake (Dietvorst et al., *Yeast* 22: 775-88 (2005)), or expression of the maltase MAL32 on the cell surface (Dietvorst et al., *Yeast* 24: 27-38 (2007)). The saccharification step could be omitted altogether, if the liquefaction step produced sufficient levels of mono-, di-, or tri-saccharides and *S. cerevisiae* or its genetically modified variants were used for the fermentation step.

*Pseudomonas saccharophila* expresses a maltotetraose-forming maltotetraohydrolase (EC 3.2.1.60; G4-forming amylase; G4-amylase; "Amy3A"; or "PS4" herein). The nucleotide sequence of the *P. saccharophila* gene encoding PS4 has been determined. Zhou et al., "Nucleotide sequence of the maltotetraohydrolase gene from *Pseudomonas saccharophila*," *FEBS Lett.* 255: 37-41 (1989); GenBank Acc. No. X16732. PS4 is expressed as a precursor protein with an N-terminal 21-residue signal peptide. The mature form of PS4, as set forth in SEQ ID NO: 1, contains 530 amino acid residues with a catalytic domain at the N-terminus and a starch binding domain at the C-terminus. PS4 displays both endo- and exo-α-amylase activity. Endo-α-amylase activity is useful for decreasing the viscosity of gelatinized starch, and exo-α-amylase activity is useful for breaking down malto-dextrins to smaller saccharides. The exo-α-amylase activity of PS4, however, has been thought to produce only maltotetraoses, which are not suitable substrates for the *S. cerevisiae* α-glucosidase. For this reason, PS4 has been thought to be unsuitable in a process of liquefaction of corn syrup to produce ethanol.

SUMMARY

Contrary to this notion, and from what is newly discovered as set forth herein, conditions are provided under which *P. saccharophila* G4-forming amylase (PS4) advantageously can be used in an enzyme-catalyzed liquefaction step to produce ethanol from starch, e.g., cornstarch, wheat starch, or barley starch. In the present methods, wild-type PS4 produces significant amounts of maltotrioses, which can be utilized by *S. cerevisiae* in a subsequent fermentation step to produce ethanol. This property of PS4 advantageously allows ethanol to be produced from liquefied starch in the absence of a saccharification step.

Typically, starch liquefaction is performed at ~85° C. The melting temperature ($T_m$) of PS4, however, is 65° C. at pH 5.5. Yet, in one embodiment, PS4 can liquefy cornstarch in a process in which the starch is pre-heated to 70° C., then mixed with PS4 and rapidly heated to 85° C., and held at this temperature for 30 minutes. HPLC analysis of the products of this liquefaction shows that PS4 produces significant amounts of maltotriose in addition to maltotetraose.

In another embodiment, variants of PS4 that are more thermostable than the wild-type PS4 show improved performance in liquefaction, as measured by the viscosity of the liquefact. Particular variants include a truncation of PS4, where the C-terminal starch-binding domain is removed. Other thermostable variants comprise one or more amino acid modifications to the wild-type PS4 enzyme sequence, or modifications to the sequence of the C-terminal truncated PS4 variant.

Compared to wild-type PS4, PS4 variants advantageously may produce more maltotriose than maltotetraose. Further, PS4 variants can produce more glucose and maltose even than currently used amylases, such as SPEZYME™ Xtra (Danisco US Inc., Genencor Division). This results in a higher observed ethanol yield from fermentation, which can exceed 2.5% v/v ethanol in embodiments using yeast that ferment glucose and maltose. It is expected that the ethanol yield can be further increased by fermenting liquefacts produced by PS4 variants with a yeast strain that can metabolize maltotrioses, such as *S. cerevisiae*.

Accordingly, the present disclosure provides a method of processing starch comprising liquefying a starch and/or saccharifying a starch liquefact to form a saccharide syrup by adding a *Pseudomonas saccharophila* amylase (PS4) variant that comprises a sequence having at least 90%, 91%, 92%, 93%, 94%, 95%, 96%, 97%, 98%, or 99% sequence identity to the amino acid sequence of SEQ ID NO: 1, residues 1 to 429 of SEQ ID NO: 1, or SEQ ID NO: 2. The PS4 variant may have an altered thermostability, an altered endo-amylase activity, an altered exo-amylase activity, and/or an altered ratio of exo- to endo amylase activity compared to the amino acid sequence of SEQ ID NO: 1, residues 1-429 of SEQ ID NO: 1, or SEQ ID NO: 2. The PS4 variant may comprise one or more following amino acid substitutions: N33Y, D34N, G70D, K71R, V113I, G121A/D/F, G134R, A141P, N145D, Y146G, I157L, G158T, S161A, L178F, A179T, Y198F, G223A/E/F, S229P, H272Q, V290I, G303E, H307K/L, A309P, S334P, W339E, and/or D343E of SEQ ID NO: 1, 2, 3, 4, 5, or 6. The PS4 variant may comprise the amino acid sequence of SEQ ID NO: 3, 4, 5, or 6. The PS4 variant may comprise one or more amino acid substitutions at following positions: 7, 8, 32, 38, 49, 62, 63, 64, 67, 72, 73, 74, 75, 76, 104, 106, 107, 110, 112, 116, 119, 122, 123, 124, 125, 126, 128, 130, 137, 138, 140, 142, 143, 144, 148, 149, 150, 151, 154, 156, 163, 164, 168, 169, 182, 183, 192, 195, 196, 200, 202, 208, 213, 220, 222, 225, 226, 227, 232, 233, 234, 236, 237, 239, 253, 255, 257, 260, 264, 267, 269, 271, 276, 282, 285, 295, 297, 300, 302, 305, 308, 312, 323, 324, 325, 341, 358, 367, 379, 390, of SEQ ID NO: 1, 2, 3, 4, 5, or 6; one or more following amino acid substitutions: A3T, G9A, H13R, I46F, D68E, G69A/E/H/I/K/M/R/T, G70A/E/L/P/Q/S/V, K71M, G100A/S, G121I/P/R, A131T, G134C, A141S, N145S, Y146D/E, G153A/D, G158C/F/I/L/P/Q/V, S161G/H/K/P/R/T/V, G166N, I170E/K/L/M/N, L178N/Q/W, A179E/N/P/R/S, A179S, G184Q, G188A, A199P, G223C/F/H/M/N/Q/W/Y, S229N, W238E/G/K/P/Q/R, G303L, H307D/E/F/G/K/M/P/Q/R/S/W/Y, A309E/I/M/T/V, S334A/H/K/L/M/Q/R/T, and/or H335M of SEQ ID NO: 1, 2, 3, 4, 5, or 6; and/or one or more amino acid substitutions at positions of 420, 422, and/or 424 of SEQ ID NO: 1. The presently disclosed PS4 variant may comprise one or more following amino acid substitutions: A3T, P7S, A8N, G9A, H13R, P32S, I38M, I46F, D49V, D62N, F63A/D/E/L/V, S64N/T, T67G/H/K/N/Q/R/V, D68E, G69A/E/H/I/K/M/R/T, G70A/E/L/P/Q/S/V, K71M, S72E/K/N/T, G73D/E/L/M/N/S/T, G74S, G75C/E/F/R/S/W/Y, E76V, G100A/S, G104N/R, G106K, V107M, L110F, D112E, N116D, N119E/G/S/Y, G121I/P/R, Y122A/E/Q/W, P123S, D124S, K125A/D/E/G/P/Q/W, E126D/N, N128E, P130S, A131T, G134C, R137C, N138D/E/S, C140A/R, A141S, D142E/G/N, P143T, G144E, N145S, Y146D/E, N148K/S, D149H/L/V, C150A, D151A/V/W, G153A/D, D154E/G/Y, F156Y, G158C/F/I/L/P/Q/V, S161G/H/K/P/R/T/V, L163M, N164R, G166N, P168L, Q169D/E/G/K/N/R/V, I170E/K/L/M/N, L178N/Q/W, A179E/N/P/R/S, R182D/G/H/M/S, S183G, G184Q, G188A, F192M/Y, V195D, R196A/G/K/P/Q/S/T/V/Y, A199P, P200A/G, R202K, S208T, S213N, L220A/T, K222M/Y, G223C/F/H/M/N/Q/W/Y, S225E/G/V, E226C/D/G/W, Y227C/D/G/K/T, S229N, W232F/G/H/I/K/L/N/P/Q/R/S/T/Y, R233H, N234R, A236E, S237D/G, W238E/G/K/P/Q/R, Q239L, V253G, D255V, A257V, E260K/R, N264D, V267I, D269N/S/V, K271A/L/Q, G276R, W282S, V285A, T295C, Y297H, G300E, N302K, G303L, Q305E/L/T, H307D/E/F/G/K/M/P/Q/R/S/W/Y, W308A/C/G/K/N/Q/R/S/T, A309E/I/M/T/V, D312E, W323M, T324A/L/M, S325G, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6; and/or one or more substitutions of S420G, D422N/P/Q, and/or G424D/S of SEQ ID NO: 1. In one aspect, the PS4 variant may comprise one or more amino acid substitutions at following positions: 7, 32, 49, 62, 63, 64, 72, 73, 74, 75, 76, 107, 110, 112, 116, 119, 122, 123, 125, 128, 130, 137, 138, 140, 142, 143, 144, 148, 149, 150, 151, 154, 156, 163, 164, 168, 169, 182, 183, 192, 195, 196, 202, 220, 222, 226, 227, 232, 233, 234, 236, 237, 239, 253, 255, 257, 260, 264, 269, 271, 276, 282, 285, 297, 300, 302, 305, 308, 312, 323, 324, 325, 341, 358, 367, and/or 379 of SEQ ID NO: 1, 2, 3, 4, 5, or 6; one or more following amino acid substitutions: A3T, H13R, I38M, I46F, T67G/H/K/N/Q/R/V, G69A/E/H/I/K/M/R/T, G70E/L/P/Q/V, K71M, G100A/S, G104R, G106K, G121I/P/R, D124S, E126D/N, A131T, G134C, A141S, N145S, Y146D/E, G153A/D, G158C/F/I/L/P/Q/V, S161G/H/K/P/R/T/V, G166N, I170E/K/L/M/N, L178N/Q/W, A179E/N/P/R/S, G188A, A199P, P200A, G223C/F/H/M/N/Q/W/Y, S225E/G/V, W238E/G/K/P/Q/R, T295C, G303L, H307D/G/M/P/S, A309E/I/M/T/V, S334A/H/K/L/M/Q/R/T, H335M, and/or D390E of SEQ ID NO: 1, 2, 3, 4, 5, or 6; one or more amino acid substitutions S420G and/or D422/N/P/Q of SEQ ID NO: 1; and/or an amino acid substitution at position 424 of SEQ ID NO: 1. In another aspect, the PS4 variant may comprise one or more following amino acid substitutions: A3T, P7S, H13R, P32S, I38M, I46F, D49V, D62N, F63A/D/E/L/V, S64N/T, T67G/H/K/N/Q/R/V, G69A/E/H/I/K/M/R/T, G70E/L/P/Q/V, K71M, S72E/K/N/T, G73D/E/L/M/N/S/T, G74S, G75C/E/F/R/S/W/Y, E76V, G100A/S, G104R, G106K, V107M, L110F, D112E, N116D, N119E/G/S/Y, G121I/P/R, Y122A/E/Q/W, P123S, D124S, K125A/D/E/G/P/Q/W, E126D/N, N128E, P130S, A131T, G134C, R137c, N138D/E/S, C140A/R, A141S, D142E/G/N, P143T, G144E, N145S, Y146D/E, N148K/S, D149H/L/V, C150A, D151A/V/W, G153A/D, D154E/G/Y, F156Y, G158C/F/I/L/P/Q/V, S161G/H/K/P/R/T/V, L163M, N164R, G166N, P168L, Q169D/E/G/K/N/R/V, I170E/K/L/M/N, L178N/Q/W, A179E/N/P/R/S, R182D/G/H/M/S, S183G, G188A, F192M/Y, V195D, R196A/G/K/P/Q/S/T/V/Y, A199P, P200A, R202K, L220A/T, K222M/Y, G223C/F/H/M/N/Q/W/Y, S225E/G/V, E226C/D/G/W, Y227C/D/G/K/T, W232F/G/H/I/K/L/N/P/Q/R/S/T/Y, R233H, N234R, A236E, S237D/G, W238E/G/K/P/Q/R, Q239L, V253G, D255V, A257V, E260K/R, N264D, D269N/S/V, K271A/L/Q, G276R, W282S, V285A, T295C, Y297H, G300E, N302K, G303L, Q305E/L/T, H307D/G/M/P/S, W308A/C/G/K/N/Q/R/S/T, A309E/I/M/T/V, D312E, W323M, T324A/L/M, S325G, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6; and/or one or more following amino acid substitutions: S420G, D422N/P/Q, and/or G424D/S of SEQ ID NO: 1. In a further aspect, the PS4 variant may comprise one or more amino acid substitutions at following positions: 49, 62, 63, 64, 72, 73, 74, 75, 76, 107, 112, 116, 119, 122, 123, 125, 128, 130, 137, 140, 143, 144, 148, 149, 150, 151, 154, 156, 163, 164, 168, 169, 182, 183, 192, 195, 196, 202, 257, 282, 285, 297, 300, 305, 308, 312, 323, and/or 325 of SEQ ID NO: 1, 2, 3, 4, 5, or 6; one or more following amino acid substitutions: A3T, P7S, H13R, I38M, I46F, T67G/H/K/N/Q/R/V, G69A/E H/I/K/M/R/T, G70E/L/P/Q/V, K71M, G100A/S, G104R, G106K, L110F, G121I/P/R, D124S, E126D/N, A131T, G134C, N138D/E, D142/E/G/N, N145S, Y146D/E, G153A/D, G158C/F/I/L/P/Q/V, S161G/H/K/P/R/T/V, G166N, I170E/K/L/M, L178N/Q/W, A179E1N/P/R/S, G188A, A199P, P200A, L220T, K222M/Y, G223C/F/H/M/N/Q/W/Y, S225E/V, E226C/D/G/W, Y227C/D/G/K/T, W232F/G/H/I/K/N/P/Q/R/S/T/Y, R233H, N234R, A236E, S237D/G, W238E/G/K/P/Q/R, Q239L, V253G, D255V, E260KR, N264D, D269N/S/V, K271A/L/Q, G276R, T295C, N302K, G303L, H307D/G/M/P/S, A309E/I/M/T/V, T324L/M, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6; and one or more following amino acid substitutions: S420G, D422N/P/Q, and/or G424S of SEQ ID NO: 1. In yet another aspect, the PS4 variant may comprise one or more following amino acid substitutions: A3T, P7S, H13R, I38M, I46F, D49V, D62N, F63A/D/E/L/V, S64N/T, T67G/H/K/N/Q/R/V, G69A/E/I/H/I/K/M/R/T, G70E/L/P/O/V, K71M, S72E/K/N/ T, G73D/E/L/M/N/S/T, G74S, G75C/E/F/R/S/W/Y, E76V, G100A/S, G104R, G106K, V107M, L110F, D112E, N116D, N119E/G/S/Y, G121I/P/R, Y122A/E/Q/W, P123S, D124S, K125A/D/E/G/P/Q/W, E126D/N, N128E, P130S, A131T, G134C, R137C, N138D/E, C140A/R, D142E/G/N, P143T, G144E, N145S, Y146D/E, N148K/S, D149H/L/V, C150A, D151A/V/W, G153A/D, D154E/G/Y, F156Y, G158C/F/I/L/ P/Q/V, S161G/H/K/P/R/T/V, L163M, N164R, G166N, P168L, Q169E/G/K/N/R/V, I170E/K/L/M, L178N/Q/W, A179E/N/P/R/S, R182D/G/H/M/S, S183G, G188A, F192M/ Y, V195D, R196A/G/K/P/Q/S/T/V/Y, A199P, P200A, R202K, L220T, K222M/Y, G223C/F/H/M/N/Q/W/Y, S225E/V, E226C/D/G/W, Y227C/D/G/K/T, W232F/G/H/I/ K/N/P/Q/R/S/T/Y, R233H, N234R, A236E, S237D/G, W238E/G/K/P/Q/R, Q239L, V253G, D255V, A257V, E260K/R, N264D, D269N/S/V, K271A/L/Q, G276R, W282S, V285A, T295C, Y297H, G300E, N302K, G303L, Q305E/L/T, H307D/G/M/P/S, W308A/C/G/K/N/Q/R/S/T, A309E/I/M/T/V, D312E, W323M, T324L/M, S325G, S334A/H/K/L/M/Q/R/T, H335M, Y341C/E, R358A/E/G/L/ N/Q/T/V, S367Q/R, S379G, and/or D390E of SEQ ID NO: 1, 2, 3, 4, 5, or 6, and/or one or more following amino acid substitutions: S420G, D422N/P/Q, and/or G424S of SEQ ID NO: 1. The PS4 variant may have up to 25, 23, 21, 19, 17, 15, 13, or 11 amino acid deletions, additions, insertions, or substitutions compared to the amino acid sequence of SEQ ID NO: 1, 2, 3, 4, 5, or 6.

The present disclosure contemplates a PS4 variant that may comprise additional one or more amino acid substitutions at the following positions: N33, D34, G70, G121, G134, A141, Y146, I157, S161, L178, A179, G223, S229, H307, A309, and/or S334 of SEQ ID NO: 1 or 2. In one aspect, the PS4 variant comprises one or more following amino acid substitutions: N33Y, D34N, G70D, G121F, G134R, A141P, Y146G, I157L, S161A, L178F, A179T, G223E, S229P, H307K, A309P, and/or S334P of SEQ ID NO: 1 or 2.

The present disclosure also contemplates a PS4 variant that may have an altered thermostability compared to the amino acid sequence of SEQ ID NO: 1, residues 1 to 429 of SEQ ID NO: 1, or SEQ ID NO: 2. The PS4 variant may be more thermostable than the amino acid sequence of SEQ ID NO: 1, residues 1 to 429 of SEQ ID NO: 1, or SEQ ID NO: 2. In one aspect, the PS4 variant that is more thermostable may comprise one or more following amino acid substitutions: A3T, I38M, G70L, Q169K/R, R182G/H, P200G, G223N, S237D, D269V, K271A/Q, S367Q/R, S379G, and/or S420G of SEQ ID NO: 1 or 2. In another aspect, the PS4 variant that is more thermostable may comprise additional one or more amino acid substitutions at following positions: G134, A141, I157, G223, H307, S334, and/or D343 of SEQ ID NO: 1 or 2. In a further aspect, the PS4 variant that is more thermostable may comprise one or more following amino acid substitutions: G134R, A141P, I157L, G223A, H307L, S334P, and/or D343E of SEQ ID NO: 1 or 2. In yet another aspect, the PS4 variant may further comprise one or more amino acid substitutions at following positions: N33, D34, K71, L178, and/or A179 of SEQ ID NO: 1 or 2. The PS4 variant may comprises one or more amino acid substitutions: N33Y, D34N, K71R, L178F, and/or A179T of SEQ ID NO: 1 or 2.

The present disclosure further contemplates a PS4 variant that may have an altered endo-amylase activity, an altered exo-amylase activity, and/or an altered ratio of exo- to endo-amylase activity compared to the amino acid sequence of SEQ ID NO: 1, residues 1 to 429 of SEQ ID NO: 1, or SEQ ID NO: 2. The PS4 variant may comprise one or more following amino acid substitutions: A3T, G69K, G70E, K71M, G73D/ E, G75C/E, Y122A, C140A, G144E, Y146D/E, N148K, C150A, D151A/V/W, G153A, G158I/P, S161G/H/K/P/R, Q169D/E/G/N/R, R196Q/S/T, R202K, S208T, S213N, K222M, G223C/F/H/M/Q/W/Y, E226D, Y227D/G/K/T, S229N, W232Q/S/T, T295C, Q305T, W308A/C/G/Q/R/S/T, A309I/V, W323M, T324L/M, S334A/H/M/Q, and/or R358E/ L/N/Q/T/V of SEQ ID NO: 1 or 2. The PS4 variant may comprise additional one or more amino acid substitutions at following positions: W66, I157, E160, S161, R196, W221, K222, E226, D254, Q305, H307, and/or W308 of SEQ ID NO: 1 or 2. The PS4 variant may comprise one or more following amino acid substitutions: W66S, E160F/G/L/P/R/ S, S161A, R196H/P/V, W221A, K222T, Q305T/L, H307L, and/or W308A/L/S of SEQ ID NO: 1 or 2.

In one aspect the PS4 variant may have an increased endo-amylase activity or a decreased ratio of exo- to endo-amylase activity compared to the amino acid sequence of SEQ ID NO: 1, residues 1 to 429 of SEQ ID NO: 1, or SEQ ID NO: 2. The PS4 variant may comprise one or more following amino acid substitutions: G69K, G73D/E, Y122A, C140A, C150A, G153A, G158I/P, S161G/H/K/P/R, Q169R, S208T, S229N, T295C, Q305T, and/or R358E/L/Q/T/V of SEQ ID NO: 1 or 2. The PS4 variant may comprise additional one or more amino acid substitutions at following positions: substitutions: W66S, R196H/P/V, W221A, K222T, H307L, and/or W308 of SEQ ID NO: 1 or 2.

In another aspect, the PS4 variant may have an increased exo-amylase activity or an increased ratio of exo- to endo-amylase activity compared to the amino acid sequence of SEQ ID NO: 1, residues 1 to 429 of SEQ ID NO: 1, or SEQ ID NO: 2. The PS4 variant may comprise one or more following amino acid substitutions: A3T, G70E, K71M, G75C/E, G144E, Y146D/E, 1N148K, D151A/V/W, Q169D/E/G/N, R196Q/S/T, R202K, S213N, K222M, G223C/F/H/M/Q/W/ Y, E226D, Y227D/G/K/T, W232Q/S/T, W308A/C/G/Q/R/S/ T, A309I/V, W323M, T324L/M, S334A/H/M/Q, and/or R358N of SEQ ID NO: 1 or 2. The PS4 variant may comprise additional one or more following amino acid substitutions: E160F/G/L/P/R/S, S161A, and/or Q305T/L of SEQ ID NO: 1 or 2.

In a further aspect, the starch processing method may further comprise adding a debranching enzyme, an isoamylase, a pullulanase, a protease, a cellulase, a hemicellulase, a lipase, a cutinase, or any combination of said enzymes, to the starch liquefact. The starch processing method may be suitable for starch from corns, cobs, wheat, barley, rye, milo, sago, cassava, tapioca, sorghum, rice, peas, bean, banana, or potatoes.

In yet another aspect, the disclosed starch processing method may comprise fermenting the saccharide syrup to produce ethanol. The disclosed method may further comprise recovering the ethanol. The ethanol may be obtained by distilling the starch, wherein the fermenting and the distilling are carried out simultaneously, separately, or sequentially.

BRIEF DESCRIPTION OF THE DRAWINGS

The accompanying drawings are incorporated in and constitute a part of this specification and illustrate various embodiments. In the drawings below, "PS4" is replaced with the abbreviation "SAS." The abbreviations refer to the same protein and are interchangeable.

DETAILED DESCRIPTION

Figure 1:
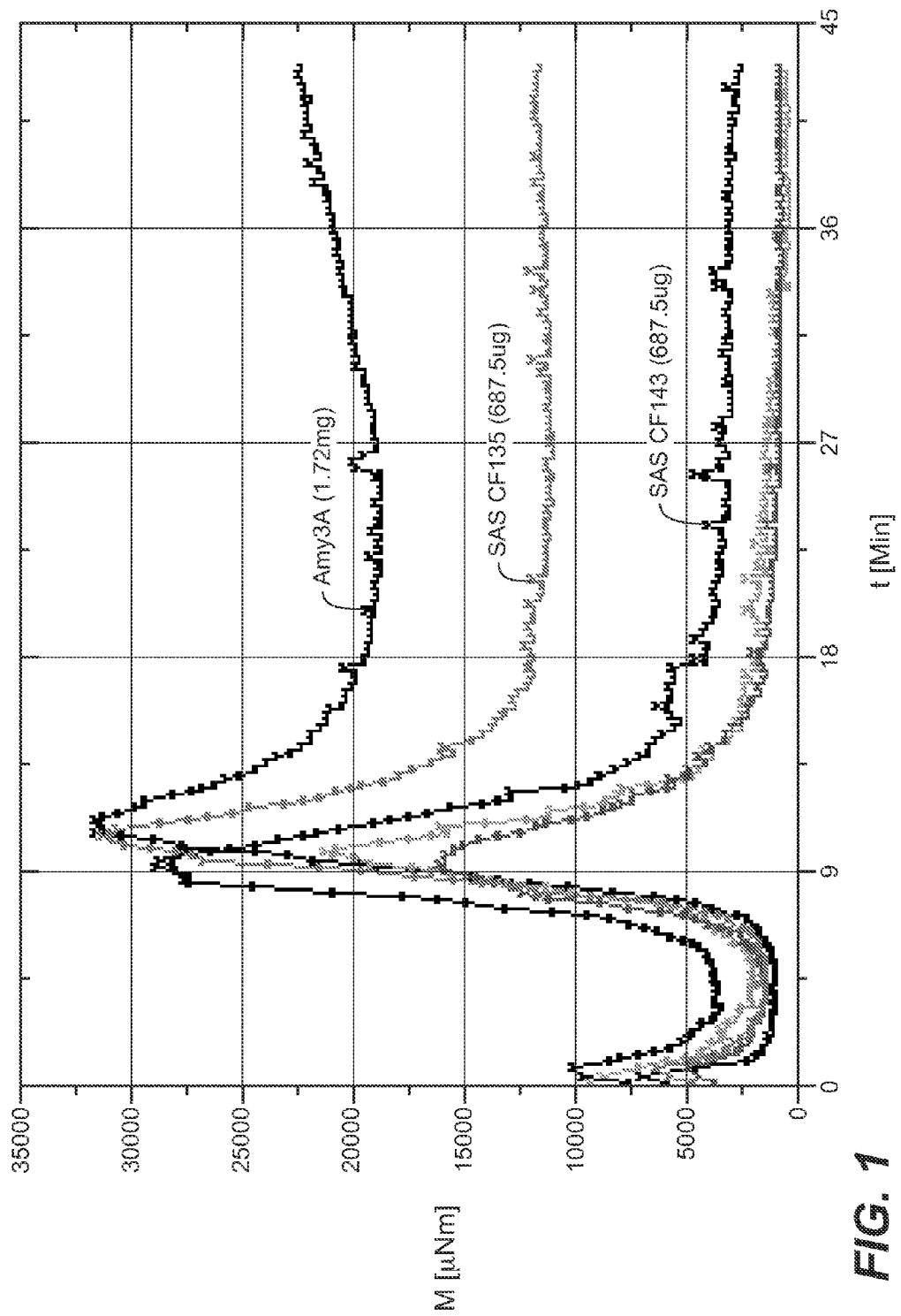
FIG. 1 depicts the liquefaction performance, measured in viscosity (μNm) as a function of time (min), using wild-type Amy3A G4-amylase (SEQ ID NO: 1) or thermostable PS4 variants CF135 (SEQ ID NO: 3 with residues 419-429 of SEQ ID NO: 1 fused at the C-terminus) and CF143 (SEQ ID NO: 4 with residues 419-429 of SEQ ID NO:1 fused at the C-terminus).

PS4, a C-terminal truncated variant thereof, and thermostable variants thereof, are provided. The PS4 and variants thereof are useful in processing starch that advantageously produces significant amounts of maltotrioses, which can be utilized by *S. cerevisiae* or a genetically engineered variant thereof in a subsequent fermentation step to produce ethanol. The process of producing ethanol advantageously does not require the use of glucoamylases and/or maltogenic α-amylases in a saccharification step to convert maltodextrins to mono-, di-, and tri-saccharides. PS4 may occasionally be referred to as SAS in the specification and figures. "PS4" and "SAS" are synonymous.

1. DEFINITIONS AND ABBREVIATIONS

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. Definitions

"Amylase" means an enzyme that is, among other things, capable of catalyzing the degradation of starch. An endo-acting amylase activity cleaves α-D-(1→4) O-glycosidic linkages within the starch molecule in a random fashion. In contrast, an exo-acting amylolytic activity cleaves a starch molecule from the non-reducing end of the substrate. "Endo-acting amylase activity," "endo-activity," "endo-specific activity," and "endo-specificity" are synonymous, when the terms refer to PS4. The same is true for the corresponding terms for exo-activity.

A "variant" or "variants" refers to either polypeptides or nucleic acids. The term "variant" may be used interchangeably with the term "mutant." Variants include insertions, substitutions, transversions, truncations, and/or inversions at one or more locations in the amino acid or nucleotide sequence, respectively. The phrases "variant polypeptide" and "variant enzyme" mean a PS4 protein that has an amino acid sequence that has been modified from the amino acid sequence of a wild-type PS4. The variant polypeptides include a polypeptide having a certain percent, e.g., 80%, 85%, 90%, 91%, 92%, 93%, 94%, 95%, 96%, 97%, 98%, or 99%, of sequence identity with the parent enzyme. As used herein, "parent enzymes," "parent sequence," "parent polypeptide," "wild-type PS4," and "parent polypeptides" mean enzymes and polypeptides from which the variant polypeptides are based, e.g., the PS4 of SEQ ID NO: 1. A "parent nucleic acid" means a nucleic acid sequence encoding the parent polypeptide. A "wild-type" PS4 occurs naturally and includes naturally occurring allelic variants of the PS4 of SEQ ID NO: 1. The signal sequence of a "variant" may be the same (SEQ ID NO: 8) or may differ from the wild-type PS4. A variant may be expressed as a fusion protein containing a heterologous polypeptide. For example, the variant can comprise a signal peptide of another protein or a sequence designed to aid identification or purification of the expressed fusion protein, such as a His-Tag sequence.

To describe the various PS4 variants that are contemplated to be encompassed by the present disclosure, the following nomenclature will be adopted for ease of reference. Where the substitution includes a number and a letter, e.g., 141P, then this refers to {position according to the numbering system/substituted amino acid}. Accordingly, for example, the substitution of an amino acid to proline in position 141 is designated as 141P. Where the substitution includes a letter, a number, and a letter, e.g., A 141P, then this refers to {original amino acid/position according to the numbering system/substituted amino acid}. Accordingly, for example, the substitution of alanine with proline in position 141 is designated as A141P.

Where two or more substitutions are possible at a particular position, this will be designated by contiguous letters, which may optionally be separated by slash marks "/", e.g., G303ED or G303E/D.

Sequence identity is determined using standard techniques known in the art (see e.g., Smith and Waterman, *Adv. Appl. Math.* 2: 482 (1981); Needleman and Wunsch, *J. Mol. Biol.* 48: 443 (1970); Pearson and Lipman, *Proc. Natl. Acad. Sci. USA* 85: 2444 (1988); programs such as GAP, BESTHT, FASTA, and TFASTA in the Wisconsin Genetics Software Package (Genetics Computer Group, Madison, Wis.); and Devereux et al., *Nucleic Acid Res.*, 12: 387-395 (1984)).

The "percent (%) nucleic acid sequence identity" or "percent (%) amino acid sequence identity" is defined as the percentage of nucleotide residues or amino acid residues in a candidate sequence that are identical with the nucleotide residues or amino acid residues of the starting sequence (e.g., PS4). The sequence identity can be measured over the entire length of the starting sequence.

"Sequence identity" is determined herein by the method of sequence alignment. For the purpose of the present disclosure, the alignment method is BLAST described by Altschul et al., (Altschul et al., *J. Mol. Biol.* 215: 403-410 (1990); and Karlin et al, *Proc. Natl. Acad. Sci. USA* 90: 5873-5787 (1993)). A particularly useful BLAST program is the WU-BLAST-2 program (see Altschul et al, *Meth. Enzymol.* 266: 460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

"Variant nucleic acids" can include sequences that are complementary to sequences that are capable of hybridizing to the nucleotide sequences presented herein. For example, a variant sequence is complementary to sequences capable of hybridizing under stringent conditions, e.g., 50° C. and 0.2× SSC (1×SSC=0.15 M NaCl, 0.015 M sodium citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein. The melting point (Tm) of a variant nucleic acid may be about 1, 2, or 3° C. lower than the Tm of the wild-type nucleic acid. The variant nucleic acids include a polynucleotide having a certain percent, e.g., 80%, 85%, 90%, 95%, or 99%, of sequence identity with the nucleic acid encoding the parent enzyme.

As used herein, the term "expression" refers to the process by which a polypeptide is produced based on the nucleic acid sequence of a gene. The process includes both transcription and translation.

"Isolated" means that the sequence is at least substantially free from at least one other component that the sequence is naturally associated and found in nature, e.g., genomic sequences.

"Purified" means that the material is in a relatively pure state, e.g., at least about 90% pure, at least about 95% pure, or at least about 98% pure.

"Thermostable" means the enzyme retains activity after exposure to elevated temperatures. The thermostability of an enzyme is measured by its half-life ($t_{1/2}$), where half of the enzyme activity is lost by the half-life. The half-life value is calculated under defined conditions by measuring the residual amylase activity. To determine the half-life of the enzyme, the sample is heated to the test temperature for 1-10 min, and activity is measured using a standard assay for PS4 activity, such as the Betamyl® assay (Megazyme, Ireland).

As used herein, "optimum pH" means the pH at which PS4 or a PS4 variant displays the activity in a standard assay for PS4 activity, measured over a range of pH's.

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of identity or "homology" with the subject amino acid sequences and the subject nucleotide sequences. A "homologous sequence" includes a polynucleotide or a polypeptide having a certain percent, e.g., 80%, 85%, 90%, 95%, or 99%, of sequence identity with another sequence. Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following removal of a signal sequence, for example. Typically, homologues will comprise the same active site residues as the subject amino acid sequence. Homologues also retain amylase activity, although the homologue may have different enzymatic properties than the wild-type PS4.

As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, "biologically active" refers to a sequence having a similar structural, regulatory or biochemical function as the naturally occurring sequence, although not necessarily to the same degree.

As used herein the term "starch" refers to any material comprised of the complex polysaccharide carbohydrates of plants, such as corn, comprised of amylose and amylopectin with the formula $(C_6H_{10}O_5)_x$, where X can be any number. The term "granular starch" refers to raw, i.e., uncooked starch, e.g., starch that has not been subject to gelatinization.

The term "liquefaction" refers to the stage in starch conversion in which gelatinized starch is hydrolyzed to give low molecular weight soluble dextrins. As used herein the term "saccharification" refers to enzymatic conversion of starch to glucose. The term "degree of polymerization" (DP) refers to the number (n) of anhydroglucopyranose units in a given saccharide. Examples of DP1 are the monosaccharides glucose and fructose. Examples of DP2 are the disaccharides maltose and sucrose.

As used herein the term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanol producing microorganism and at least one enzyme, such as PS4 or a variant thereof, are present during the same process step. SSF refers to the contemporaneous hydrolysis of granular starch substrates to saccharides and the fermentation of the saccharides into alcohol, for example, in the same reactor vessel.

As used herein "ethanologenic microorganism" refers to a microorganism with the ability to convert a sugar or oligosaccharide to ethanol.

1.2. Abbreviations

The following abbreviations apply unless indicated otherwise:
ADA azodicarbonamide
Amy3A a wild-type *P. saccharophila* G4-forming amylase
cDNA complementary DNA
CGTase cyclodextrin glucanotransferase
DEAE diethylamino ethanol
$dH_2O$ deionized water
DNA deoxyribonucleic acid
DP-n degree of polymerization with n subunits
ds dry solid
ds-DNA double-stranded DNA
EC enzyme commission for enzyme classification
FGSC Fungal Genetics Stock Center
G121F glycine (G) residue at position 121 of SEQ ID NO: 2 is replaced with a phenylalanine (F) residue, where amino acids are designated by single letter abbreviations commonly known in the art
HPLC High Performance Liquid Chromatography
LU Lipase Units, a measure of phospholipase activity per unit mass of enzyme
mRNA messenger ribonucleic acid
PCR polymerase chain reaction
PDB Protein Database Base
PEG polyethyleneglycol
ppm parts per million
PS4 *P. saccharophila* G4-forming amylase
RT-PCR reverse transcriptase polymerase chain reaction
SAS *P. saccharophila* G4-forming amylase
SDS-PAGE sodium dodecyl sulfate-polyacrylamide gel electrophoresis
1×SSC 0.15 M NaCl, 0.015 M sodium citrate, pH 7.0
SSF simultaneous saccharification and fermentation
$t_{1/2}$ half life
Tm melting temperature (° C.) at which 50% of the subject protein is melted
ΔTm ° C. increase in the Tm
w/v weight/volume
w/w weight/weight

2. *PSEUDOMONAS SACCHAROPHILA* α-AMYLASE (PS4) AND VARIANTS THEREOF

An isolated and/or purified polypeptide comprising a PS4 or variant thereof is provided. In one embodiment, the PS4 is a mature form of the polypeptide (SEQ ID NO: 1), wherein the 21 amino acid leader sequence is cleaved, so that the N-terminus of the polypeptide begins at the aspartic acid (D) residue. Variants of PS4 include a PS4 in which the C-terminal starch binding domain is removed. A representative amino acid sequence of a mature PS4 variant in which the starch binding domain is removed is the one having an amino acid sequence of residues. 1 to 429 of SEQ ID NO: 1, or SEQ ID NO: 2 with residues 419-429 of SEQ ID NO:1 fused at the C-terminus. Other PS4 variants include variants wherein between one and about 25 amino acid residues have been added or deleted with respect to wild-type PS4 or the PS4 having an amino acid sequence of residues 1 to 429 of SEQ ID NO: 1, or SEQ ID NO: 2 with residues 419-429 of SEQ ID NO:1 fused at the C-terminus. In one aspect, the PS4 variant has the amino acid sequence of residues 1 to 429 of SEQ ID NO: 1, wherein any number between one and about 25 amino acids have been substituted. Representative embodiments of these variants include CF135 (SEQ ID NO: 3 with residues 419-429 of SEQ ID NO:1 fused at the C-terminus), CF143 (SEQ ID NO: 4 with residues 419-429 of SEQ ID NO:1 fused at the C-terminus), CF149 (SEQ ID NO: 5 with residues 419-429 of SEQ ID NO:1 fused at the C-terminus), and CF154 (SEQ ID NO: 6 with residues 419-429 of SEQ ID NO: 1 fused at the C-terminus).

In another aspect, the PS4 variant has the sequence of wild-type PS4, wherein any number between one and about 25 amino acids have been substituted. Representative examples of PS4 variants having single amino acid substitutions are shown in TABLE 3. Examples of PS4 variants having combinations of amino acid substitutions are shown in TABLES 4 and 7. TABLE 4 depicts various amino acids that have been modified to form a core variant sequence, which is additionally modified as indicated for the PS4 variants listed in TABLE 7. TABLE 7 further summarizes the effect of various mutations on endo- or exo-amylase activity, as well as the ratio of exo- to endo-amylase activity. In addition to the amino acid residue modifications listed in TABLES 3-4, additional specific PS4 residues that may be modified include A3, S44, A93, G103, V109, G172, A211, G265, N302, G313, and G342. PS4 variants may have various combinations of the amino acid substitutions disclosed herein. A process of using a PS4 variant may comprise the use of a single PS4 variant or a combination, or blend, of PS4 variants.

PS4 variants advantageously may produce more maltotriose than maltotetraose. Further, the PS4 variants can produce more glucose and maltose than currently used amylases, such as SPEZYME™ Xtra (Danisco US Inc., Genencor Division). This results in a higher observed ethanol yield from fermentation, which can exceed 2.5% (v/v) ethanol in embodiments using yeast that ferment glucose and maltose. PS4 variants are provided that have substantial endo-amylase activity, compared to wild-type PS4, and/or have a lower ratio of exo- to endo-amylase activity compared to wild-type PS4. Such PS4 variants may be particularly useful in a liquefaction process, when used alone or combination with other PS4 variants, where internal cleavage of complex branching saccharides lowers the viscosity of the substrate.

Representative examples of amino acid substitutions that maintain or increase thermostability include the substitutions made to the variants CF135, CF143, CF149, and CF154. The PS4 variant CF135 has an amino acid sequence of SEQ ID NO: 3 with residues 419-429 of SEQ ID NO: 1 fused at the C-terminus. This variant contains the amino acid substitution A141P. The variant CF143, having an amino acid sequence of SEQ ID NO: 4 with residues 419-429 of SEQ ID NO: 1 fused at the C-terminus, has the additional substitution G223A. The variant CF149, having an amino acid sequence of SEQ ID NO: 5 with residues 419-429 of SEQ ID NO: 1 fused at the C-terminus, has seven substitutions: G134R, A141P, G223A, I157L, H307L, S334P, and D343E. The variant CF154, having an amino acid sequence of SEQ ID NO: 6 with residues 419-429 of SEQ ID NO: 1 fused at the C-terminus, has the same seven substitutions as CF149, plus the substitutions N33Y, D34N, K71R, L178F, and A179T.

Figure 9:
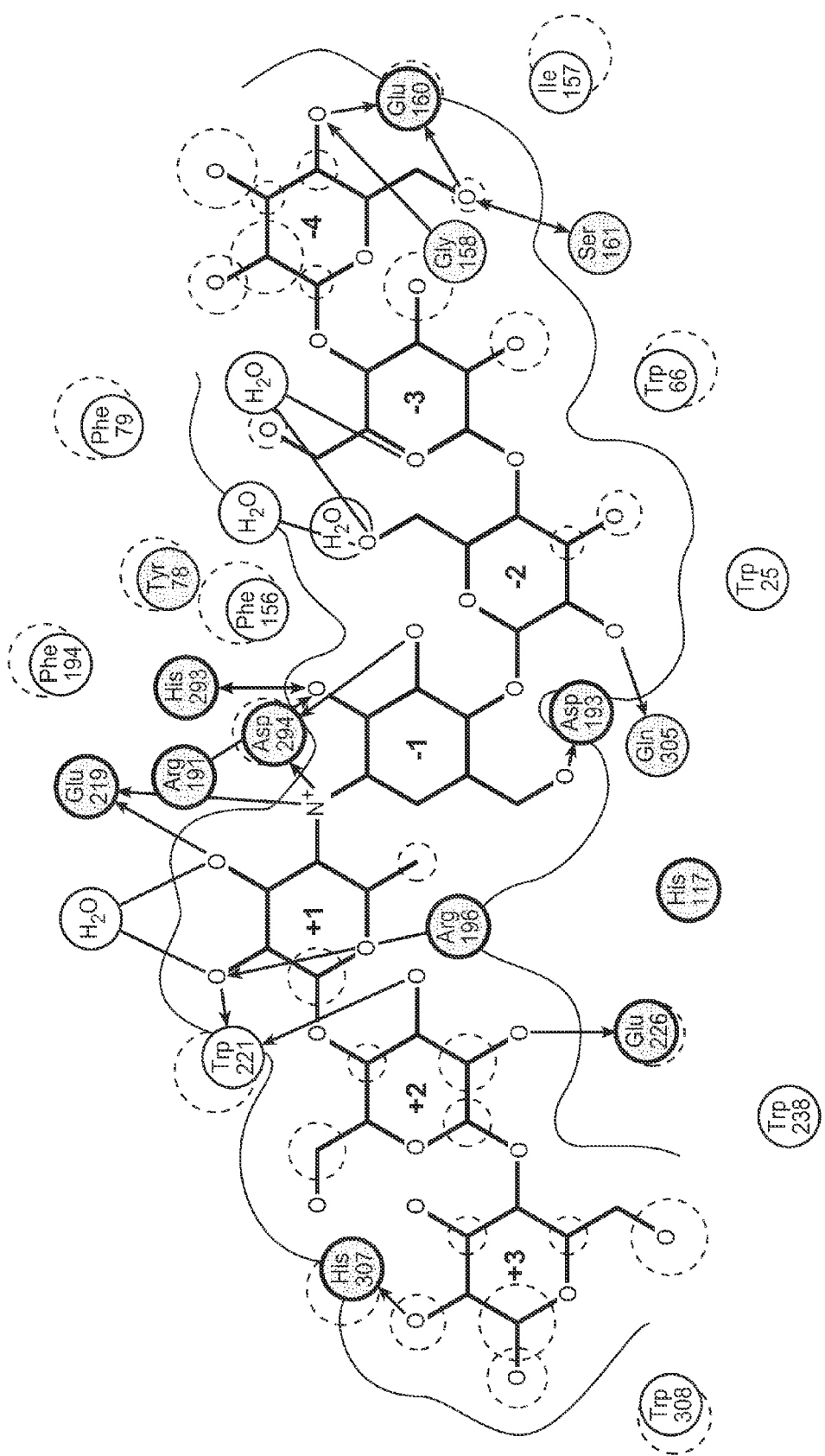
FIG. 9 depicts the interaction between PS4 and acarbose bound to the active site cleft. Sugar positions +3 through −3 of acarbose are shown.

Other particularly useful variants include those in which residues affecting substrate binding are substituted. PS4 residues involved in substrate binding include those depicted in FIG. 9. Specific residues include W66, I157, E160, S161, R196, W221, K222, H307, and W308. Substitutions of residues that affect substrate binding may affect the relative degree of endo- or exo-activity of the PS4 variant. A substitution that increases exo-activity, for example, advantageously promotes the formation of DP3 saccharides, which can be metabolized by S. cerevisiae in a process of fermentation of cornstarch to make ethanol. Representative examples of mutations affecting substrate binding include E160G, E160P, E160F, E160R, E160S, E160L, W66S, R196V, R196H, R196P, H307L, W221A, W308A, W308S, W308L, W308S, and K222T. Mutations to residues D254, R196, and E226, which are involved in an ion-pair network with K222, also are expected to be useful, since these mutations indirectly will affect the interaction of K222 with the substrate. Specific PS4 variants are provided that affect the −4, −3, −2, +2, and +3 sugar binding sites. Variants include those that affect subsets of these sites, particularly the −3, −2, +2, or +3 sites. Processes comprising the use of combinations of mutations affecting different sugar binding sites are contemplated. Specific mutations that affect the sugar binding sites are disclosed in the Examples.

The PS4 variant may comprises a sequence having at least 80%, 85%, 90%, 91%, 92%, 93%, 94%, 95%, 96%, 97%, 98%, or 99% sequence identity to the amino acid sequence of SEQ ID NO: 1, residues 1 to 429 of SEQ ID NO: 1, or SEQ ID NO: 2. The PS4 variant may have an altered thermostability, an altered endo-amylase activity, an altered exo-amylase activity, and/or an altered ratio of exo- to endo amylase activity compared to the amino acid sequence of SEQ ID NO: 1, residues 1-429 of SEQ ID NO: 1, or SEQ ID NO: 2. The PS4 variant may comprise one or more following amino acid substitutions: N33Y, D34N, G70D, K71R, V113I, G12.1A/D/F, G134R, A141P, N145D, Y146G, I157L, G158T, S161A, L178F, A179T, Y198F, G223A/E/F, S229P, H272Q, V2901, G303E, H307K/L, A309P, S334P, W339E, and/or D343E of SEQ ID NO: 1, 2, 3, 4, 5, or 6. The PS4 variant may comprise the amino acid sequence of SEQ ID NO: 3, 4, 5, or 6.

In some embodiments, the PS4 variant may comprise one or more amino acid substitutions at following positions: 7, 8, 32, 38, 49, 62, 63, 64, 67, 72, 73, 74, 75, 76, 104, 106, 107, 110, 112, 116, 119, 122, 123, 124, 125, 126, 128, 130, 137, 138, 140, 142, 143, 144, 148, 149, 150, 151, 154, 156, 163, 164, 168, 169, 182, 183, 192, 195, 196, 200, 202, 208, 213, 220, 222, 225, 226, 227, 232, 233, 234, 236, 237, 239, 253, 255, 257, 260, 264, 267, 269, 271, 276, 282, 285, 295, 297, 300, 302, 305, 308, 312, 323, 324, 325, 341, 358, 367, 379, 390, of SEQ ID NO: 1, 2, 3, 4, 5, or 6; one or more following amino acid substitutions: A3T, G9A, H13R, I46F, D68E, G69A/E/H/I/K/M/R/T, G70A/E/L/P/Q/S/V, K71M, G100A/S, G121I/P/R, A131T, G134C, A141S, N145S, Y146D/E, G153A/D, G158C/F/I/L/P/Q/V, S161G/H/K/P/R/T/V, G166N, I170E/K/L/M/N, L178N/Q/W, A179E/N/P/R/S, A179S, G184Q, G188A, A199P, G223C/F/H/M/N/Q/W/Y, S229N, W238E/G/K/P/Q/R, G303L, H307D/E/F/G/K/M/P/Q/R/S/W/Y, A309E/I/M/T/V, S334A/H/K/L/M/Q/R/T, and/or H335M of SEQ ID NO: 1, 2, 3, 4, 5, or 6; and/or one or more amino acid substitutions at positions of 420, 422, and/or 424 of SEQ ID NO: 1. Representative substitutions may include: A3T, P7S, A8N, G9A, H13R, P32S, I38M, I46F, D49V, D62N, F63A/D/E/L/V, S64N/T, T67G/H/K/N/Q/R/V, D68E, G69A/E/H/I/K/M/R/T, G70A/E/L/P/Q/S/V, K71M, S72E/K/N/T, G73D/E/L/M/N/S/T, G74S, G75C/E/F/R/S/W/Y, E76V, G100A/S, G104N/R, G106K, V107M, L110F, D112E, N116D, N119E/G/S/Y, G121I/P/R, Y122A/E/Q/W, P123S, D124S, K125A/D/E/G/P/Q/W, E126D/N, N128E, P130S, A131T, G134C, R137C, N138D/E/S, C140A/R, A141S, D142E/G/N, P143T, G144E, N145S, Y146D/E, N148K/S, D149H/L/V, C150A, D151A/V/W, G153A/D, D154E/G/Y, F156Y, G158C/F/I/L/P/Q/V, S161G/H/K/P/R/T/V, L163M, N164R, G166N, P168L, Q169D/E/G/K/N/R/V, I170E/K/L/M/N, L178N/Q/W, A179E/N/P/R/S, R182D/G/H/M/S, S183G, G184Q, G188A, F192M/Y, V195D, R196A/G/K/P/Q/S/T/V/Y, A199P, P200A/G, R202K, S208T, S213N, L220A/T, K222M/Y, G223C/F/H/M/N/Q/W/Y, S225E/G/V, E226C/D/G/W, Y227C/D/G/K/T, S229N, W232F/G/H/I/K/L/N/P/Q/R/S/T/Y, R233H, N234R, A236E, S237D/G, W238E/G/K/P/Q/R, Q239L, V253G, D255V, A257V, E260K/R, N264D, V267I, D269N/S/V, K271A/L/Q, G276R, W282S, V285A, T295C, Y297H, G300E, N302K, G303L, Q305E/L/T, H307D/E/F/G/K/M/P/Q/R/S/W/Y, W308A/C/G/K/N/Q/R/S/T, A309E/I/M/T/V, D312E, W323M, T324A/L/M, S325G, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6, and/or one or more substitutions of S420G, D422N/P/Q, and/or G424D/S of SEQ ID NO: 1.

In some embodiments, the PS4 variant may comprise one or more amino acid substitutions at following positions: 7, 32, 49, 62, 63, 64, 72, 73, 74, 75, 76, 107, 110, 112, 116, 119, 122, 123, 125, 128, 130, 137, 138, 140, 142, 143, 144, 148, 149, 150, 151, 154, 156, 163, 164, 168, 169, 182, 183, 192, 195, 196, 202, 220, 222, 226, 227, 232, 233, 234, 236, 237, 239, 253, 255, 257, 260, 264, 269, 271, 276, 282, 285, 297, 300, 302, 305, 308, 312, 323, 324, 325, 341, 358, 367, and/or 379 of SEQ ID NO: 1, 2, 3, 4, 5, or 6; one or more following amino acid substitutions: A3T, H13R, I38M, I46F, T67G/H/K/N/Q/R/V, G69A/E/H/I/K/M/R/T, G70E/L/P/Q/V, K71M, G100A/S, G104R, G106K, G121I/P/R, D124S, E126D/N, A131T, G134C, A141S, N145S, Y146D/E, G153A/D, G158C/F/I/L/P/Q/V, S161G/H/K/P/R/T/V, G166N, I170E/K/L/M/N, L178N/Q/W, A179E/N/P/R/S, G188A, A199P, P200A, G223C/F/H/M/N/Q/W/Y, S225E/G/V, W238E/G/K/P/Q/R, T295C, G303L, H307D/G/M/P/S, A309E/I/M/T/V, 334A/H/K/L/M/Q/R/T, H335M, and/or D390E of SEQ ID NO: 1, 2, 3, 4, 5, or 6; one or more amino acid substitutions S420G and/or D422N/P/Q of SEQ ID NO: 1; and/or an amino acid substitution at position 424 of SEQ ID NO: 1. Representative substitutions may include: A3T, P7S, H13R, P32S, I38M, I46F, D49V, D62N, F63A/D/E/L/V, S64N/T, T67G/H/K/N/Q/R/V, G69A/E/H/I/K/M/R/T, G70E/L/P/Q/V, K71M, S72E/K/N/T, G73D/E/L/M/N/S/T, G74S, G75C/E/F/R/S/W/Y, E76V, G100A/S, G104R, G106K, V107M, L110F, D112E, N116D, N119E/G/S/Y, G121I/P/R, Y122A/E/Q/W, P123S, D124S, K125A/D/E/G/P/Q/W, E126D/N, N128E, P130S, A131T, G134C, R137C, N138D/E/S, C140A/R, A141S, D142E/G/N, P143T, G144E, N145S, Y146D/E, N148K/S, D149H/L/V, C150A, D151A/V/W, G153A/D, D154E/G/Y, F156Y, G158C/F/I/L/P/Q/V, S161G/H/K/P/R/T/V, L163M, N164R, G166N, P168L, Q169D/E/G/K/N/R/V, I170E/K/L/M/N, L178N/Q/W, A179E/N/P/R/S, R182D/G/H/M/S, S183G, G188A, F192M/Y, V195D, R196A/G/K/P/Q/S/T/V/Y, A199P, P200A, R202K, L220A/T, K222M/Y, G223C/F/H/M/N/Q/W/Y, S225E/G/V, E226C/D/G/W, Y227C/D/G/K/T, W232F/G/H/I/I/K/L/N/P/Q/R/S/T/Y, R233H, N234R, A236E, S237D/G, W238E/G/K/P/Q/R, Q239L, V253G, D255V, A257V, E260K/R, N264D, D269N/S/V, K271A/L/Q, G276R, W282S, V285A, T295C, Y297H, G300E, N302K, G303L, Q305E/L/T, H307D/G/M/P/S, W308A/C/G/K/N/Q/R/S/T, A309E/I/M/T/V, D312E, W323M, T324L/M, S325G, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6, and/or one or more following amino acid substitutions: S420G, D422N/P/Q, and/or G424D/S of SEQ ID NO: 1.

In other embodiments, the PS4 variant may comprise one or more amino acid substitutions at following positions: 49, 62, 63, 64, 72, 73, 74, 75, 76, 107, 112, 116, 119, 122, 123, 125, 128, 130, 137, 140, 143, 144, 148, 149, 150, 151, 154, 156, 163, 164, 168, 169, 182, 183, 192, 195, 196, 202, 257, 282, 285, 297, 300, 305, 308, 312, 323, and/or 325 of SEQ ID NO: 1, 2, 3, 4, 5, or 6; one or more following amino acid substitutions: A3T, P7S, H13R, I38M, I46F, T67G/H/K/N/Q/R/V, G69A/E/H/I/K/M/R/T, G70E/L/P/Q/V, K71M, G100A/S, G104R, G106K, L110F, G121I/P/R, D124S, E126D/N, A131T, G134C, N138D/E, D142/E/G/N, N145S, Y146D/E, G153A/D, G158C/F/I/L/P/Q/V, S161G/H/K/P/R/T/V, G166N, I170E/K/L/M, L178N/Q/W, A179E/N/P/R/S, G188A, A199P, P200A, L220T, K222M/Y, G223C/F/H/M/N/Q/W/Y, S225E/V, E226C/D/G/W, Y227C/D/G/K/T, W232F/G/H/I/K/N/P/Q/R/S/T/Y, R233H, N234R, A236E, S237D/G, W238E/G/K/P/Q/R, Q239L, V253G, D255V, E260K/R, N264D, D269N/S/V, K271A/L/Q, G276R, T295C, N302K, G303L, H307D/G/M/P/S, A309E/I/M/T/V, T324L/M, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6; and one or more following amino acid substitutions: S420G, D422N/P/Q, and/or G424S of SEQ ID NO: 1. Representative substitutions may include: A3T, P7S, H13R, I38M, I46F, D49V, D62N, F63A/D/E/L/V, S64N/T, T67G/H/K/N/Q/R/V, G69A/E/H/I/K/M/R/T, G70E/L/P/Q/V, K71M, S72E/K/N/T, G73D/E/L/M/N/S/T, G74S, G75C/E/F/R/S/W/Y, E76V, G100A/S, G104R, G106K, V107M, L110F, D112E, N116D, N119E/G/S/Y, G121I/P/R, Y122A/E/Q/W, P123S, D124S, K125A/D/E/G/P/Q/W, E126D/N, N128E, P130S, A131T, G134C, R137C, N138D/E, C140A/R, D142E/G/N, P143T, G144E, N145S, Y146D/E, N148K/S, D149H/L/V, C150A, D151A/V/W, G153A/D, D154E/G/Y, F156Y, G158C/F/I/L/P/Q/V, S161G/H/K/P/R/T/V, L163M, N164R, G166N, P168L, Q169E/G/K/N/R/V, I170E/K/L/M, L178N/Q/W, A179E/N/P/R/S, R182D/G/H/M/S, S183G, G188A, F192M/Y, V195D, R196A/G/K/P/Q/S/T/V/Y, A199P, P200A, R202K, L220T, K222M/Y, G223C/F/H/M/N/Q/W/Y, S225E/V, E226C/D/G/W, Y227C/D/G/K/T, W232F/G/H/I/K/N/P/Q/R/S/T/Y, R233H, N234R, A236E, S237D/G, W238E/G/K/P/Q/R, Q239L, V253G, D255V, A257V, E260K/R, N264D, D269N/S/V, K271A/L/Q, G276R, W282S, V285A, T295C, Y297H, G300E, N302K, G303L, Q305E/L/T, H307D/G/M/P/S, W308A/C/G/K/N/Q/R/S/T, A309E/I/M/T/V, D312E, W323M, T324L/M, S325G, S334A/H/K/L/M/Q/R/T, H335M, Y341C/E, R358A/E/G/L/N/Q/T/V, S367Q/R, S379G, and/or D390E of SEQ ID NO: 1, 2, 3, 4, 5, or 6, and/or one or more following amino acid substitutions: S420G, D422N/P/Q, and/or G424S of SEQ ID NO: 1.

The PS4 variant may have up to 25, 23, 21, 19, 17, 15, 13, or 11 amino acid deletions, additions, insertions, or substitutions compared to the amino acid sequence of SEQ ID NO: 1, 2, 3, 4, 5, or 6.

The PS4 variant may comprise additional one or more amino acid substitutions at the following positions: N33, D34, G70, G121, G134, A141, Y146, I157, S161, L178, A179, G223, S229, H307, A309, and/or S334 of SEQ ID NO: 1 or 2. Representative substitutions may include: N33Y, D34N, G70D, G121F, G134R, A141P, Y146G, I157L, S161A, L178F, A179T, G223E, S229P, H307K, A309P, and/or S334P of SEQ ID NO: 1 or 2.

In other embodiments, the PS4 variant may have an altered thermostability compared to the amino acid sequence of SEQ ID NO: 1, residues 1 to 429 of SEQ ID NO: 1, or SEQ ID NO: 2. The altered thermostability may be elevated thermostability compared to the amino acid sequence of SEQ ID NO: 1, residues 1 to 429 of SEQ ID NO: 1, or SEQ ID NO: 2. The PS4 variant that is more thermostable may comprise one or more following amino acid substitutions: A3T, I38M, G70L, Q169K/R, R182G/H, P200G, G223N, S237D, D269V, K271A/Q, S367Q/R, S379G, and/or S420G of SEQ ID NO: 1 or 2. Moreover, the PS4 variant may comprise additional one or more amino acid substitutions at following positions: G134, A141, I157, G223, H307, S334, and/or D343 of SEQ ID NO: 1 or 2. Representative substitutions may include: G134R, A141P, I157L, G223A, H307L, S334P, and/or D343E of SEQ ID NO: 1 or 2. The PS4 variant may further comprise one or more amino acid substitutions at following positions: N33, D34, K71, L178, and/or A179 of SEQ ID NO: 1 or 2. Representative substitutions may include: N33Y, D34N, K71R, L178F, and/or A179T of SEQ ID NO: 1 or 2.

In yet other embodiments, the PS4 variant that may have an altered endo-amylase activity, an altered exo-amylase activity, and/or an altered ratio of exo- to endo-amylase activity compared to the amino acid sequence of SEQ ID NO: 1, residues 1 to 429 of SEQ ID NO: 1, or SEQ ID NO: 2. The PS4 variant may comprise one or more following amino acid substitutions: A3T, G69K, G70E, K71M, G73D/E, G75C/E, Y122A, C140A, G144E, Y146D/E, N148K, C150A, D151A/V/W, G153A, G158I/P, S161G/H/K/P/R, Q169D/E/G/N/R, R196Q/S/T, R202K, S208T, S213N, K222M, G223C/F/H/M/Q/W/Y, E226D, Y227D/G/K/T, S229N, W232Q/S/T, T295C, Q305T, W308A/C/G/Q/R/S/T, A309I/V, W323M, T324L/M, S334A/H/M/Q, and/or R358E/L/N/Q/T/V of SEQ ID NO: 1 or 2. Moreover, the PS4 variant may comprise additional one or more amino acid substitutions at following positions: W66, I157, E160, S161, R196, W221, K222, E226, D254, Q305, H307, and/or W308 of SEQ ID NO: 1 or 2. Representative substitutions may include: W66S, E160F/G/L/P/R/S, S161A, R196H/P/V, W221A, K222T, Q305T/L, H307L, and/or W308A/L/S of SEQ ID NO: 1 or 2.

The present disclosure also relates to each and every core variant sequence or backbone as shown in TABLE 4 comprising the substitution patterns as shown for each variant in TABLE 7. The disclosure further relates to the exact recited variants as shown in TABLE 4 with the substitutions as recited in TABLE 7, i.e., the core variant sequence containing only the recited mutations or substitution patterns as shown in TABLE 7. The disclosure further relates to PS4 variants comprising the amino acid sequence of SEQ ID NO: 1, residues 1 to 429 of SEQ ID NO: 1, or SEQ ID NO: 2, and comprising the substitution patterns as shown in TABLE 7. Furthermore, the disclosure relates to PS4 variants comprising the amino acid sequence of SEQ ID NO: 1, residues 1 to 429 of SEQ ID NO: 1, or SEQ ID NO: 2, and containing only the substitution patterns as shown in TABLE 7.

Nucleic acids encoding the polypeptides above also are provided. In one embodiment, a nucleic acid encoding a PS4 variant is a cDNA encoding the protein comprising an amino acid sequence of residues 1-429 of SEQ ID NO: 1. For example, the cDNA may have the corresponding sequence of the native mRNA, set forth in SEQ ID NO: 7. See GenBank Acc. No. X16732. As is well understood by one skilled in the art, the genetic code is degenerate, meaning that multiple codons in some cases may encode the same amino acid. Nucleic acids include genomic DNA, mRNA, and cDNA that encodes a PS4 variant.

2.1. PS4 Variant Characterization

Enzyme variants can be characterized by their nucleic acid and primary polypeptide sequences, by three dimensional structural modeling, and/or by their specific activity. Additional characteristics of the PS4 variant include stability, pH range, oxidation stability, and thermostability, for example. Levels of expression and enzyme activity can be assessed using standard assays known to the artisan skilled in this field. In another aspect, variants demonstrate improved performance characteristics relative to the wild-type enzyme, such as improved stability at high temperatures, e.g., 65-85° C. PS4 variants are advantageous for use in liquefaction or other processes that require elevated temperatures, such as baking. For example, a thermostable PS4 variant can degrade starch at temperatures of about 55° C. to about 85° C. or more.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

A nucleic acid complementary to a nucleic acid encoding any of the PS4 variants set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast.

3. PRODUCTION OF PS4 VARIANTS

The PS4 variants provided herein may be produced synthetically or through recombinant expression in a host cell, according to procedures well known in the art. The expressed PS4 variant optionally is isolated prior to use. In another embodiment, the PS4 variant is purified following expression. Methods of genetic modification and recombinant production of PS4 variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including PS4-encoding polynucleotide sequences, primers, vectors, selection methods, host cells, purification and reconstitution of expressed PS4 variants, and characterization of PS4 variants, including useful buffers, pH ranges, $Ca^{2+}$ concentrations, substrate concentrations and enzyme concentrations for enzymatic assays, are herein incorporated by reference.

In another embodiment, suitable host cells include a Gram positive bacterium selected from the group consisting of *Bacillus subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. thuringiensis*, *Streptomyces lividans*, or *S. murinus*; or a Gram negative bacterium, wherein said Gram negative bacterium is *Escherichia coli* or a *Pseudomonas* species. In one embodiment, the host cell is *B. subtilis*, and the expressed protein is engineered to comprise a *B. subtilis* signal sequence, as set forth in further detail below.

In some embodiments, a host cell is genetically engineered to express an PS4 variant with an amino acid sequence having at least about 80%, 85%, 90%, 91%, 92%, 93%, 94%, 95%, 96%, 97%, 98% or 99% identity with the wild-type PS4. In some embodiments, the polynucleotide encoding a PS4 variant will have a nucleic acid sequence encoding the protein of SEQ ID NO: 1 or 2 or a nucleic acid sequence having at least about 80%, 85%, 90%, 95%, 96%, 97%, 98% or 99% sequence identity with a nucleic acid encoding the protein of SEQ ID NO: 1 or 2. In one embodiment, the nucleic acid sequence has at least about 80%, 85%, 90%, 95%, 96%, 97%, 98% or 99% sequence identity to the nucleic acid of SEQ ID NO: 7.

3.1. Vectors

In some embodiments, a DNA construct comprising a nucleic acid encoding a PS4 variant is transferred to a host cell in an expression vector that comprises regulatory sequences operably linked to a PS4 encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., MOLECULAR CLONING: A LABORATORY MANUAL, $3^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™ 201, pDONR™ 221, pENTR™, pGEM® 3Z and pGEM®84Z. Exemplary for use in bacterial cells include pBR322 and pUC19, which permit replication in *E. coli*, and pE194, for example, which permits replication in *Bacillus*.

In some embodiments, a nucleic acid encoding a PS4 variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when *P. saccharophila* is the host, the promoter is a native *P. saccharophila* promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. A representative signal peptide is SEQ ID NO: 8, which is the native signal sequence of the PS4 precursor. In other embodiments, the DNA encoding the signal sequence is replaced with a nucleotide sequence encoding a signal sequence from a species other than *P. saccharophila*. In this embodiment, the polynucleotide that encodes the signal sequence is immediately upstream and in-frame of the polynucleotide that encodes the polypeptide. The signal sequence may be selected from the same species as the host cell. In one non-limiting example, the signal sequence is a cyclodextrin glucanotransferase (CGTase; EC 2.4.1.19) signal sequence from *Bacillus* sp., and the PS4 variant is expressed in a *B. subtilis* host cell. A methionine residue may be added to the N-terminus of the signal sequence.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an *A. nidulans* amdS gene as a selective marker is described in Kelley et al., *EMBO J.* 4: 475-479 (1985) and Penttila et al., *Gene* 61: 155-164 (1987).

A suitable expression vector comprising a DNA construct with a polynucleotide encoding a PS4 variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, PS4 coding region, and terminator all originate from the gene to be expressed. In some embodiments, gene truncation is obtained by deleting undesired DNA sequences, e.g., DNA encoding the C-terminal starch-binding domain, to leave the domain to be expressed under control of its own transcriptional and translational regulatory sequences. The second type of expression vector is preassembled and contains sequences required for high-level transcription and a selectable marker. In some embodiments, the coding region for a PS4 gene or part thereof is inserted into this general-purpose expression vector, such that it is under the transcriptional control of the expression construct promoter and terminator sequences. In some embodiments, genes or part thereof are inserted downstream of the strong cbh1 promoter.

3.2. Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., *Curr. Genet.* 16: 53-56 (1989). The expression of heterologous protein in *Trichoderma* is described, for example, in U.S. Pat. No. 6,022,725; U.S. Pat. No. 6,268,328; Harkki et al., *Enzyme Microb. Technol.* 13: 227-233 (1991); Harkki et al., *BioTechnol.* 7: 596-603 (1989); EP 244,234; and EP 215,594. In one embodiment, genetically stable transformants are constructed with vector systems whereby the nucleic acid encoding a PS4 variant is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

3.3. Identification of PS4 Activity

To evaluate the expression of a PS4 variant in a host cell, assays can measure the expressed protein, corresponding mRNA, or α-amylase activity. For example, suitable assays include Northern and Southern blotting, RT-PCR (reverse transcriptase polymerase chain reaction), and in situ hybridization, using an appropriately labeled hybridizing probe. Suitable assays also include measuring PS4 activity in a sample. Suitable assays of the exo-activity of the PS4 variant include, but are not limited to, the Betamyl® assay (Megazyme, Ireland). Suitable assays of the endo-activity of the PS4 variant include, but are not limited to, the Phadebas blue assay (Pharmacia and Upjohn Diagnostics AB). Assays also include HPLC analysis of liquefact prepared in the presence of the PS4 variant. HPLC can be used to measure amylase activity by separating DP-3 and DP-4 saccharides from other components of the assay.

3.4. Methods for Purifying PS4

In general, a PS4 variant produced in cell culture is secreted into the medium and may be purified or isolated, e.g., by removing unwanted components from the cell culture medium. In some cases, a PS4 variant may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example.

4. COMPOSITIONS AND USES OF PS4 VARIANTS

A PS4 variant produced and purified by the methods described above is useful for a variety of industrial applications. In one embodiment, the PS4 variant is useful in a starch conversion process, particularly in a liquefaction process of a starch, e.g., cornstarch, wheat starch, or barley starch. The desired end-product may be any product that may be produced by the enzymatic conversion of the starch substrate. For example, the desired product may be a syrup rich in saccharides useful for fermentation, particularly maltotriose, glucose, and/or maltose. The end product then can be used directly in a fermentation process to produce alcohol for fuel or drinking (i.e., potable alcohol). The skilled artisan is aware of various fermentation conditions that may be used in the production of ethanol or other fermentation end-products. A microbial organism capable of fermenting maltotrioses and/or less complex sugars, such as S. cerevisiae or a genetically modified variant thereof, is particularly useful. Suitable genetically altered variants of S. cerevisiae particularly useful for fermenting maltotrioses include variants that express AGT1 permease (Stambuck et al., Lett. Appl. Microbiol. 43: 370-76 (2006)), MTT1 and MTT1 alt (Dietvorst et al., Yeast 22: 775-88 (2005)), or MAL32 (Dietvorst et al., Yeast 24: 27-38 (2007)). PS4 variants also are useful in compositions and methods of food preparation, where enzymes that express amylase activity at high temperatures are desired.

The desirability of using a particular PS4 variant will depend on the overall properties displayed by the PS4 variant relative to the requirements of a particular application. As a general matter, PS4 variants useful for a starch conversion process have substantial endo-amylase activity compared to wild-type PS4, and/or have a lower exo- to endo-amylase activity compared to wild-type PS4. Such PS4 variants may be particularly useful in a liquefaction process, when used alone or combination with other PS4 variants, where internal cleavage of complex branching saccharides lowers the viscosity of the substrate. Some PS4 variants useful for liquefaction, however, are expected to have an endo-amylase activity comparable or even lower than wild-type PS4. Useful PS4 variants include those with more or less exo-amylase activity than the wild-type PS4, depending on the application. Compositions may include one or a combination of PS4 variants, each of which may display a different set of properties.

4.1. Preparation of Starch Substrates

Those of skill in the art are well aware of available methods that may be used to prepare starch substrates for use in the processes disclosed herein. For example, a useful starch substrate may be obtained from tubers, roots, stems, legumes, cereals or whole grain. More specifically, the granular starch comes from plants that produce high amounts of starch. For example, granular starch may be obtained from corns, cobs, wheat, barley, rye, milo, sago, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are cornstarch, wheat starch, and barley starch. The starch from a grain may be ground or whole and includes corn solids, such as kernels, bran and/or cobs. The starch may be highly refined raw starch or feedstock from starch refinery processes. Various starches also are commercially available. For example, cornstarch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling, whole kernels are ground into a fine powder and processed without fractionating the grain into its component parts. Dry milled grain thus will comprise significant amounts of non-starch carbohydrate compounds, in addition to starch. Most ethanol comes from dry milling. Alternatively, the starch to be processed may be a highly refined starch quality, for example, at least about 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. This process involves gelatinization of starch simultaneously with or followed by the addition of a PS4 variant. A thermostable PS4 variant is preferably used for this application. Additional liquefaction-inducing enzymes optionally may be added.

In some embodiments, the starch substrate prepared as described above is slurried with water. The starch slurry may contain starch as a weight percent of dry solids of about 10-55%, about 20-45%, about 30-45%, about 30-40%, or about 30-35%. The α-amylase is usually supplied, for example, at about 1500 units per kg dry matter of starch. To optimize α-amylase stability and activity, the pH of the slurry may be adjusted to the optimal pH for the PS4 variant. Other α-amylases may be added and may require different optimal conditions. Bacterial α-amylase remaining in the slurry following liquefaction may be deactivated by lowering pH in a subsequent reaction step or by removing calcium from the slurry.

The slurry of starch plus the PS4 variant may be pumped continuously through a jet cooker, which is steam heated from about 85° C. to up to 105° C. Gelatinization occurs very rapidly under these conditions, and the enzymatic activity, combined with the significant shear forces, begins the hydrolysis of the starch substrate. The residence time in the jet cooker is very brief. The partly gelatinized starch may be passed into a series of holding tubes maintained at about 85-105° C. and held for about 5 min. to complete the gelatinization process. These tanks may contain baffles to discourage back mixing. As used herein, the term "secondary liquefaction" refers the liquefaction step subsequent to primary liquefaction, when the slurry is allowed to cool to room temperature. This cooling step can be about 30 minutes to about 180 minutes, e.g. about 90 minutes to 120 minutes.

4.3. Processes of Fermentation

Yeast typically from Saccharomyces spp. is added to the mash and the fermentation is ongoing for 24-96 hours, such as typically 35-60 hours. The temperature is between about 26-34° C., typically at about 32° C., and the pH is from about pH 3-6, typically around about pH 4-5.

In one embodiment, a batch fermentation process is used in a closed system, where the composition of the medium is set at the beginning of the fermentation and is not altered during the fermentation. At the beginning of the fermentation, the medium is inoculated with the desired microbial organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Following the fermentation, the mash is distilled to extract the ethanol. The ethanol obtained according to the process of the disclosure may be used as, e.g., fuel ethanol; drinking ethanol, i.e., potable neutral spirits or industrial ethanol. Left over from the fermentation is the grain, which is typically used for animal feed, either in liquid form or dried. Further details on how to carry out liquefaction, saccharification, fermentation, distillation, and recovery of ethanol are well known to the skilled person. According to the process of the disclosure, the saccharification and fermentation may be carried out simultaneously or separately.

5. TEXTILE DESIZING COMPOSITIONS AND USE

Also contemplated are compositions and methods of treating fabrics (e.g., to desize a textile) using PS4 variant. Fabric-treating methods are well known in the art (see, e.g., U.S. Pat. No. 6,077,316). For example, in one aspect, the feel and appearance of a fabric is improved by a method comprising contacting the fabric with a PS4 variant in a solution. In one aspect, the fabric is treated with the solution under pressure.

In one aspect, a PS4 variant is applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A PS4 variant can be applied during or after the weaving to remove these sizing starch or starch derivatives. After weaving, a PS4 variant can be used to remove the size coating before further processing the fabric to ensure a homogeneous and washproof result.

A PS4 variant can be used alone or with other desizing chemical reagents and/or desizing enzymes to desize fabrics, including cotton-containing fabrics, as detergent additives, e.g., in aqueous compositions. A PS4 variant also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. A PS4 variant can be used in methods of finishing denim garments (e.g., a "bio-stoning process"), enzymatic desizing and providing softness to fabrics, and/or finishing process.

EXAMPLES

Example 1

Determination of Thermal Melting Points

Differential scanning calorimetry was used to characterize the thermal unfolding midpoint (Tm) of wild-type PS4 and the PS4 variants: CF135 (SEQ ID NO: 3 with residues 419-429 of SEQ ID NO:1 fused at the C-terminus), CF143 (SEQ ID NO: 4 with residues 419-429 of SEQ ID NO:1 fused at the C-terminus), CF149 (SEQ ID NO: 5 with residues 419-429 of SEQ ID NO:1 fused at the C-terminus), and CF154 (SEQ ID NO: 6 with residues 419-429 of SEQ ID NO: 1 fused at the C-terminus). The Tm was used as an indicator of the thermal stability of the various enzymes. Excess heat capacity curves were measured using an ultrasensitive scanning high-throughput microcalorimeter, VP-Cap DSC (MicroCal, Inc., Northampton, Mass.). Approximately 500 μL of 500 ppm of protein was needed per DSC run, and the samples were scanned over a 30-120° C. temperature range using a scan rate of 200° C./hr. The same sample was then rescanned to check the reversibility of the process. For the wild-type and variant proteins, the thermal unfolding process was irreversible. The buffer was 10 mM sodium acetate, pH 5.5, with 0.002% Tween-20. Tm values for the wild-type PS4 and PS4 variants, as well as the increase in the Tm due to the mutations (ΔTm), are shown in TABLE 1.

TABLE 1

| | Tm (° C.) | ΔTm (° C.) increase relative to wild type PS4 |
|---|---|---|
| PS4 wild-type | 66.5 | |
| PS4 CF135 | 72.6 | +6.1 |
| PS4 CF143 | 73.3 | +6.9 |
| PS4 CF149 | 79.7 | +13.3 |
| PS4 CF154 | 85.9 | +19.5 |

All the PS4 variants showed an increase in the thermal unfolding midpoint relative to the wild-type PS4. The Tm for the wild-type PS4 relative to the mutations was wild-type PS4<PS4 CF135<PS4 CF143<PS4 CF149<PS4 CF154.

Measurement of Thermostability.

Alternatively, the thermostability of a given PS4 variant was evaluated by measuring its half-life under an elevated temperature, because heat inactivation follows a 1st order reaction. For this, the residual amylase activity of a given variant was measured after it was incubated for 1-30 minutes at 72° C., 75° C., 80° C., or 85° C. in (1) 50 mM sodium citrate, 5 mM calcium chloride, pH 6.5, (2) 50 mM sodium citrate, 0.5 M sodium chloride, 5 mM calcium chloride, pH 6.5, or (3) 50 mM sodium acetate, 0.5 M sodium chloride, 2 mM calcium chloride, pH 5.0. The Betamyl® assay (Megazyme, Ireland) was used to determine the residual amylase activity. The assay mix contains 50 µL of 50 mM sodium citrate, 5 mM calcium chloride, pH 6.5, with 25 µL enzyme sample and 25 µL Betamyl substrate (paranitrophenol(PNP)-coupled maltopentaose (Glc5) and alpha-glucosidase). One Betamyl unit is defined as activity degrading 0.0351 mole/min of PNP-coupled maltopentaose. The assay contained 50 µL of 50 mM sodium citrate, 5 mM calcium chloride, pH 6.5, and 25 µL of Betamyl substrate. The assay mixture was incubated for 30 min at 40° C., then stopped by the addition of 150 µL of 4% Tris. Absorbance at 420 nm was measured using an ELISA-reader, and the Betamyl activity was calculated according to the formula Activity=A420×d in Betamyl units/ml of enzyme sample assayed, with "d" being the dilution factor of the enzyme sample. The half-lives of various PS4 variants are shown in TABLE 7.

Example 2

Determination of Starch Liquefaction Performance

Starch liquefaction performance was measured for the wild-type PS4 and thermostable PS4 variants by the rate of reduction in viscosity of a starch liquefact. A Thermo VT550 viscometer was used to determine viscosity. A slurry comprising starch substrate and an appropriate amount of enzyme was poured into the viscometer vessel. The temperature and viscosity were recorded during heating to 85° C., and incubation was continued for additional 60 to 120 minutes. Viscosity was measured as µNm as a function of time.

Wild-type PS4 liquefied starch at high temperature, e.g., 70-85° C. This result was significant, in view of the melting temperature of the wild-type PS4 of 66.5° C. The relatively high final viscosity obtained with the wild-type PS4, however, suggests that the wild-type PS4 has limited performance at these temperatures.

Liquefaction performance was compared between the full length, wild-type PS4 ("Amy3A") and the PS4 variants CF135 and CF143. As shown in FIG. 1, the PS4 variants liquefied cornstarch at a rate comparable to Amy3A. Further, the final viscosity of the liquefact was lower using CF135 and CF143, indicating that these PS4 variants exhibited a superior performance to Amy3A in this assay.

Starch Liquefaction with CF149 and CF154 Versus SPEZYME™ Xtra.

To test the ability of yeast to produce ethanol from corn liquefact generated using PS4 as an alpha-amylase, the thermostable PS4 variants CF135, CF143, CF149, and CF154 were compared to SPEZYME™ Xtra (Danisco US Inc., Genencor Division) in a conventional ethanol fermentation process run on liquefacts generated in a viscometer. A solution of Xtra at 4.86 mg/mL was added to 2.0 µg/g dry solids. PS4 variant CF149 (purified, 32.7 mg/mL) was added to 46.7 µg/g dry solids, and PS4 variant CF154 (purified, 15.9 mg/ml) was added to 46.7 µg/g dry solids. The starch solution was 30% dry solids corn flour (15 g total dry solids), pH 5.8, where the pH was adjusted with $H_2SO_4$ or $NH_4OH$, as necessary. The starch solution was preincubation for 10 min at 70° C. before the enzyme was added. The viscometer holding the reaction was held 1 min at 70° C., 100 rpm rotation. The temperature was ramped to 85° C. over 12 min, with 75 rpm rotation. The reaction then proceeded at 85° C. for 20 min at 75 rpm rotation.

Fermentation Using the CF149, CF154, or SPEZYME™ Xtra Liquefacts.

Two viscometer runs were performed for each enzyme in order to generate enough liquefact for one 50 g fermentation. After each viscometer run, liquefact was collected; liquefact from each pair of viscometer runs was pooled. Fermentations were run in duplicate in 125 mL Erlenmeyer flasks. Replicate fermentations were started on separate days due to timing constraints.

For each individual 50 g fermentation, the pH was adjusted to pH 4.3. The % dry solids was left unadjusted. Urea was added at 400 ppm final concentration. Red Star Ethanol Red yeast were added at a ratio of 0.33% (w/w); the yeast were prehydrated as a 33% (w/v) slurry before aliquoting 500 µL into flasks.

Flasks were incubated at 32° C. with stirring at 400 rpm for 48 h fermentation. The PS4 liquefact fermentations slowed slow stirring, whereas the Xtra liquefact fermentations did not stir at all. Samples were taken at t=0, 14 h, 23 h, 39 h, and 48 h and analyzed by HPLC.

Results.

Figure 2:
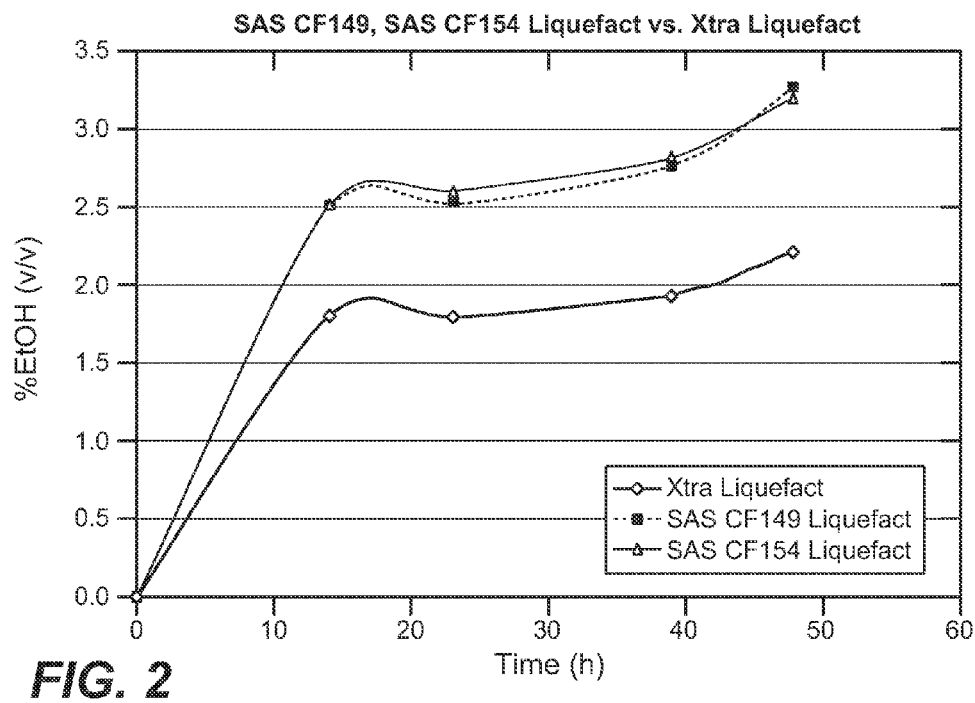
FIG. 2 depicts the production of ethanol (% v/v) as a function of time (h), using thermostable PS4 variants CF149 (SEQ ID NO: 5 with residues 419-429 of SEQ ID NO:1 fused at the C-terminus) and CF154 (SEQ ID NO: 6 with residues 419-429 of SEQ ID NO: 1 fused at the C-terminus), compared to liquefact produced with SPEZYME™ Xtra (Danisco US Inc., Genencor Division).
Figure 3:
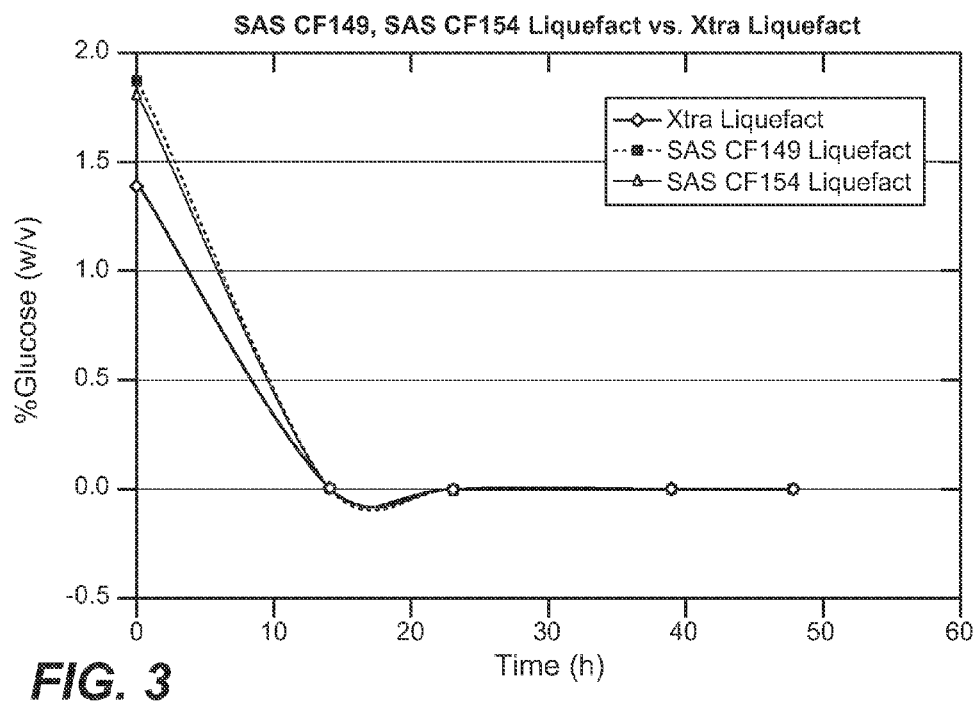
FIG. 3 depicts the utilization of glucose (% w/v) as a function of time (h) under the same conditions as used in FIG. 2.

Final ethanol yields from the fermentations using PS4 liquefacts averaged 3.2% and 3.3% (v/v), whereas the final ethanol yields from the fermentations using Xtra liquefact averaged 2.2% (v/v). See FIG. 2, TABLE 2. Ethanol levels were higher throughout the fermentations for the PS4 liquefacts than for the Xtra liquefact. Fermentations on the PS4 liquefacts appeared to start with both more glucose and maltose, both of which diminished by 14 hours as ethanol levels increased, as apparent from a comparison of FIG. 2 and FIG. 3.

TABLE 2

| Sample | Final EtOH (v/v)% |
|---|---|
| Xtra liquefact | 2.20 |
| PS4 CF149 liquefact | 3.26 |
| PS4 CF154 liquefact | 3.19 |

Figure 4:
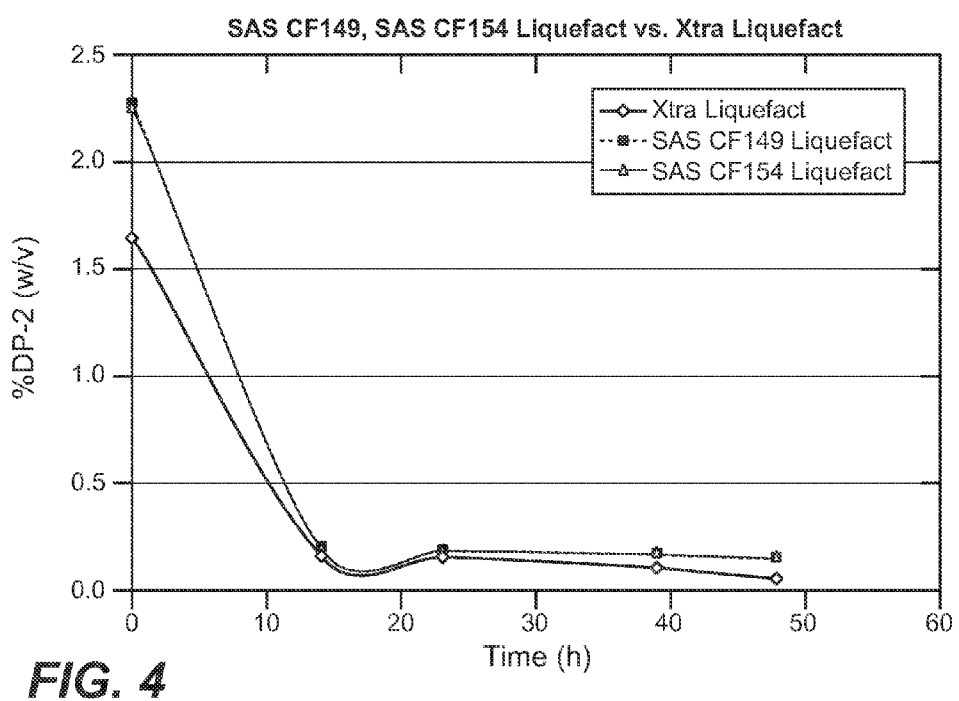
FIG. 4 depicts the change in the % w/v of di-saccharides (DP-2) as a function of time (h) under the same conditions as used in FIG. 2.
Figure 5:
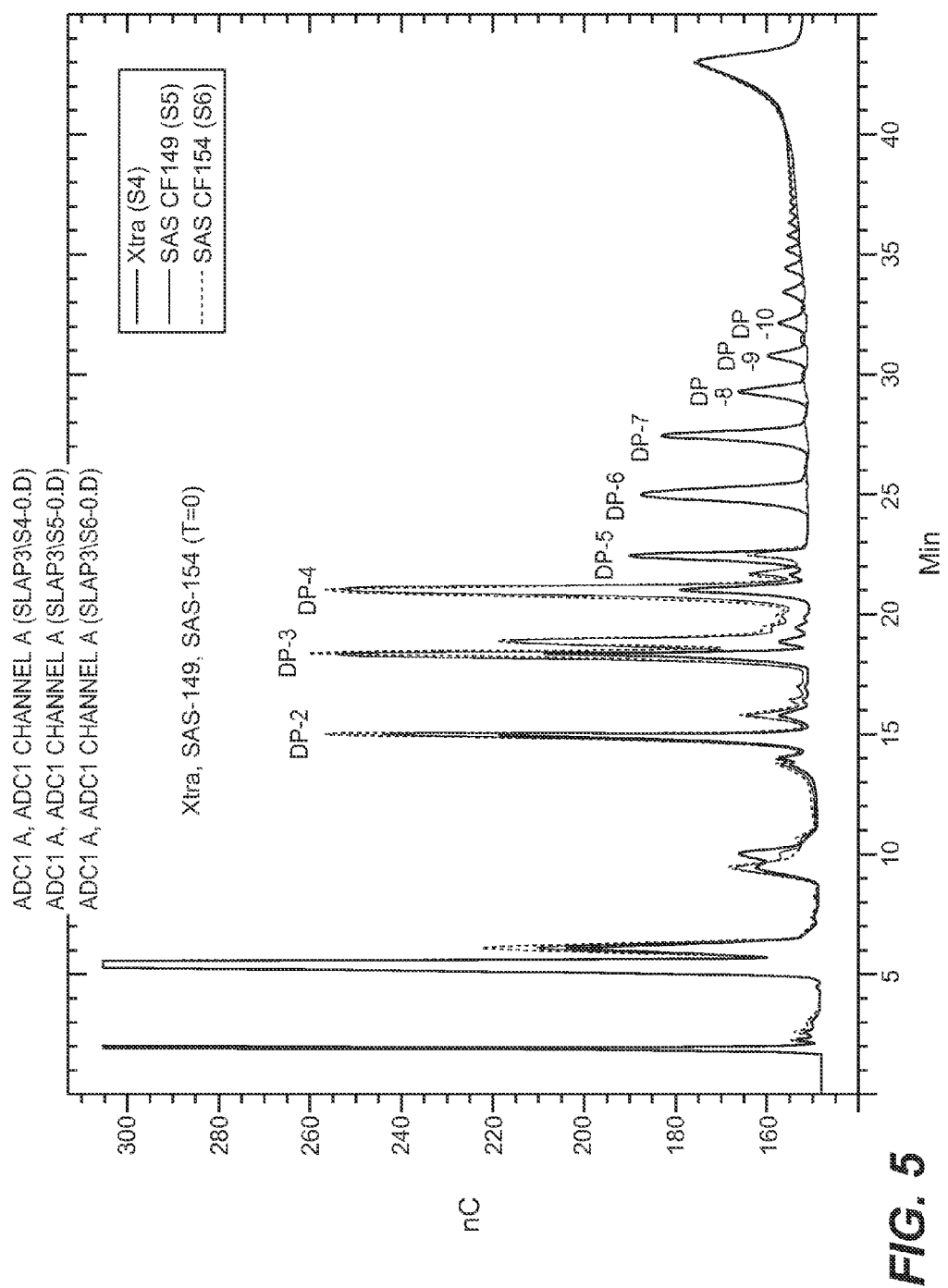
FIG. 5 depicts the rate of ethanol accumulation (% v/v) in a reaction catalyzed by CF149 (SEQ ID NO: 5 with residues 419-429 of SEQ ID NO:1 fused at the C-terminus), CF154 (SEQ ID NO: 6 with residues 419-429 of SEQ ID NO: 1 fused at the C-terminus), or Xtra.
Figure 6:
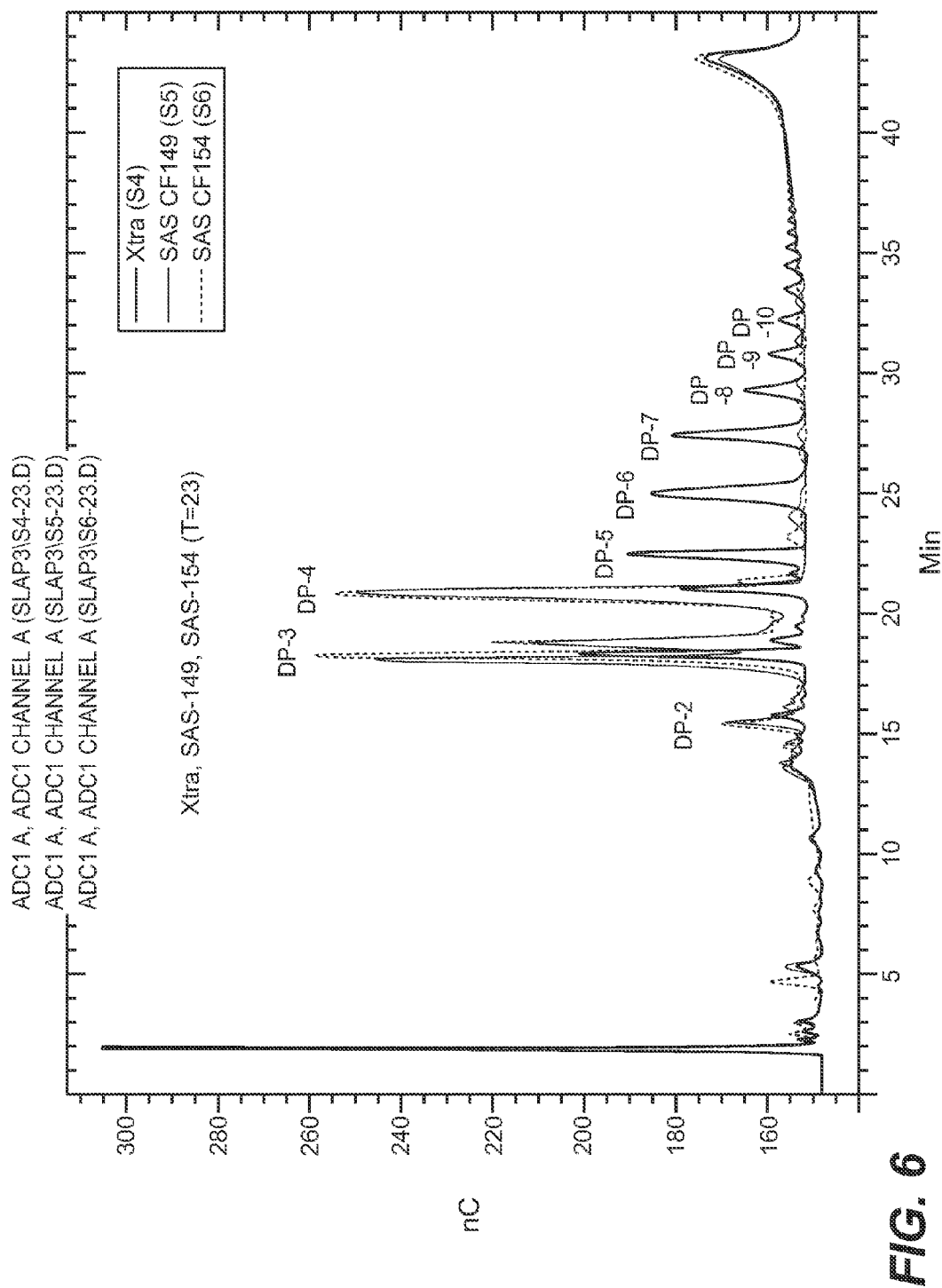
FIG. 6 depicts the rate of glucose utilization (% w/v) in a reaction catalyzed by CF149 (SEQ ID NO: 5 with residues 419-429 of SEQ ID NO:1 fused at the C-terminus), CF154 (SEQ ID NO: 6 [with residues 419-429 of SEQ ID NO: 1 fused at the C-terminus), or Xtra.
Figure 7:
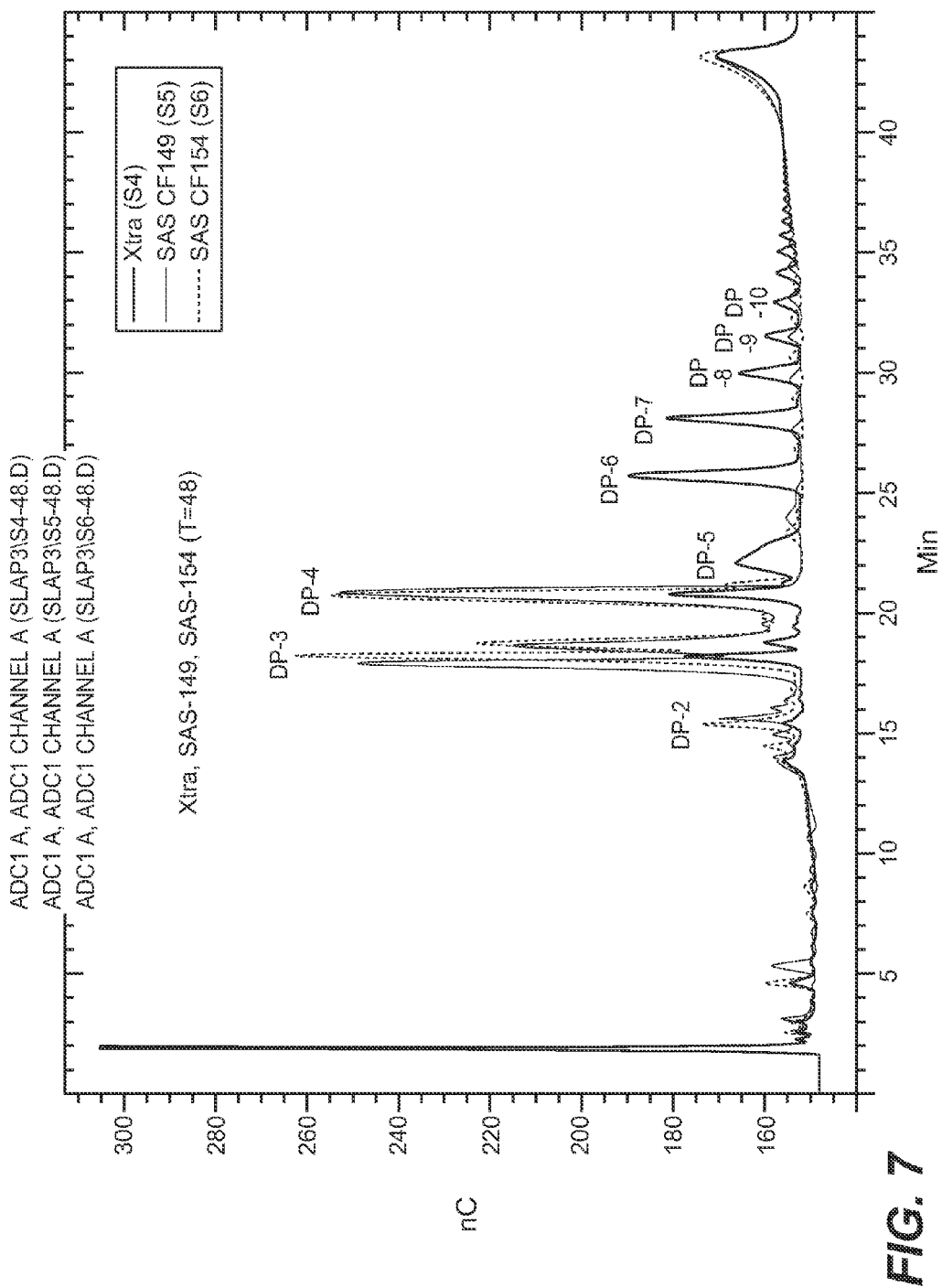
FIG. 7 depicts the rate of DP-2 utilization (% w/v) in a reaction catalyzed by CF149 (SEQ ID NO:5 with residues 419-429 of SEQ ID NO:1 fused at the C-terminus), CF154 (SEQ ID NO: 6 with residues 419-429 of SEQ ID NO: 1 fused at the C-terminus), or Xtra.

HPLC analysis of the liquefaction reaction was used to determine levels of high-DP sugars. FIG. 4 depicts the decrease in concentration of DP-2 sugars over time. FIGS. 5-7 show the full range of DP-n sugars produced over time (hours) from the initiation of the reaction. PS4 variant liquefacts started with significantly lower amounts of DP-4 sugars than the Xtra liquefact, and relatively higher amounts of DP-2, DP-3, and DP-4 sugars. DP-3 levels remained fairly constant for the PS4 liquefacts throughout the fermentations, and appeared to drop slightly for the Xtra liquefact. DP-4 peaks also remained fairly constant for all three liquefacts. The major carbohydrate produced by the PS4 variants was maltotriose (DP-3).

Example 3

Crystallization and Structure Determination of Native PS4

Crystals were obtained for the wild-type PS4 catalytic core using the Hampton PEG6000 screen. Large single crystals were obtained in 10-30% PEG6000, over the pH range 6-8. Crystals with similar morphology also were obtained by storing the protein stock solution at 4° C. without precipitant.

Data were collected at room temperature with an R-AXIS IV using CuK$\alpha$ radiation from an RU200 generator, and processed with d*TREK (MSC, The Woodland, Tex.). The cell dimensions were almost identical to those of crystal form II of the *P. stutzeri* G4-amylase. See Yoshioka et al., *J. Mol. Biol.* 271: 619-28 (1997); Hasegawa et al., *Protein Eng.* 12: 819-24 (1999). Molecular replacement calculations thus were not necessary, and rigid body refinement was used to begin structure refinement. The G4-amylase structure from RCSB Protein Database Base (PDB) Accession No. 1JDC was used with the ligand deleted. The amino acid differences between each homologue were readily apparent in 2Fo-Fc difference maps, and the correct *P. saccharophila* structure was built manually using COOT. The structure was subsequently refined using REFMAC5, included in the Collaborative Computational Project, Number 4 (CCP4) suite of programs. See CCP4, "The CCP4 Suite: Programs for Protein Crystallography,"*Acta Cryst.* D50: 760-63 (1994). Water molecules were identified using COOT, and refinement was completed with REFMAC5. Ligand atom labels and the geometry file for REFMAC5 were generated using PRODRG, available at the Dundee PRODRG2 Server.

Example 4

Overall Structure of PS4

The native structure of the PS4 catalytic core consists of 418 amino acids, 2 calcium atoms and 115 water molecules. The structure of native PS4 with acarbose, a pseudo-tetra-saccharide, consists of 418 amino acids, 2 calcium atoms, 76 water molecules, and an acarbose derived inhibitor with 7 sugar residues. The catalytic core of PS4 has a conserved 3 domain structure common to GH13 enzymes. Domain A consists of a ($\beta/\alpha$)8 barrel. Domain B is an insertion into this barrel, between $\beta$-sheet 3 and $\alpha$-helix 3, which is relatively unstructured in this enzyme, and which contains the conserved calcium ion. Domain C is a five-stranded anti-parallel $\beta$-sheet in a Greek key motif. Domain C packs against the C-terminus of Domain A. In common with *P. stutzeri* MO-19 G4-amylase, there is a second calcium ion bound at the N-terminal region.

Example 5

Preparation of Inhibitor-Bound PS4

Acarbose was added to the mother liquor of crystals grown in storage buffer, and the liquor was left to incubate at 4° C. for 24 hours. Data were collected at room temperature and processed as described above. The ligand was fitted manually into the observed difference density, and the protein ligand complex was refined with REFMAC5. See FIG. 8.

Example 6

Analysis of Enzyme Inhibitor Interactions

Figure 8:
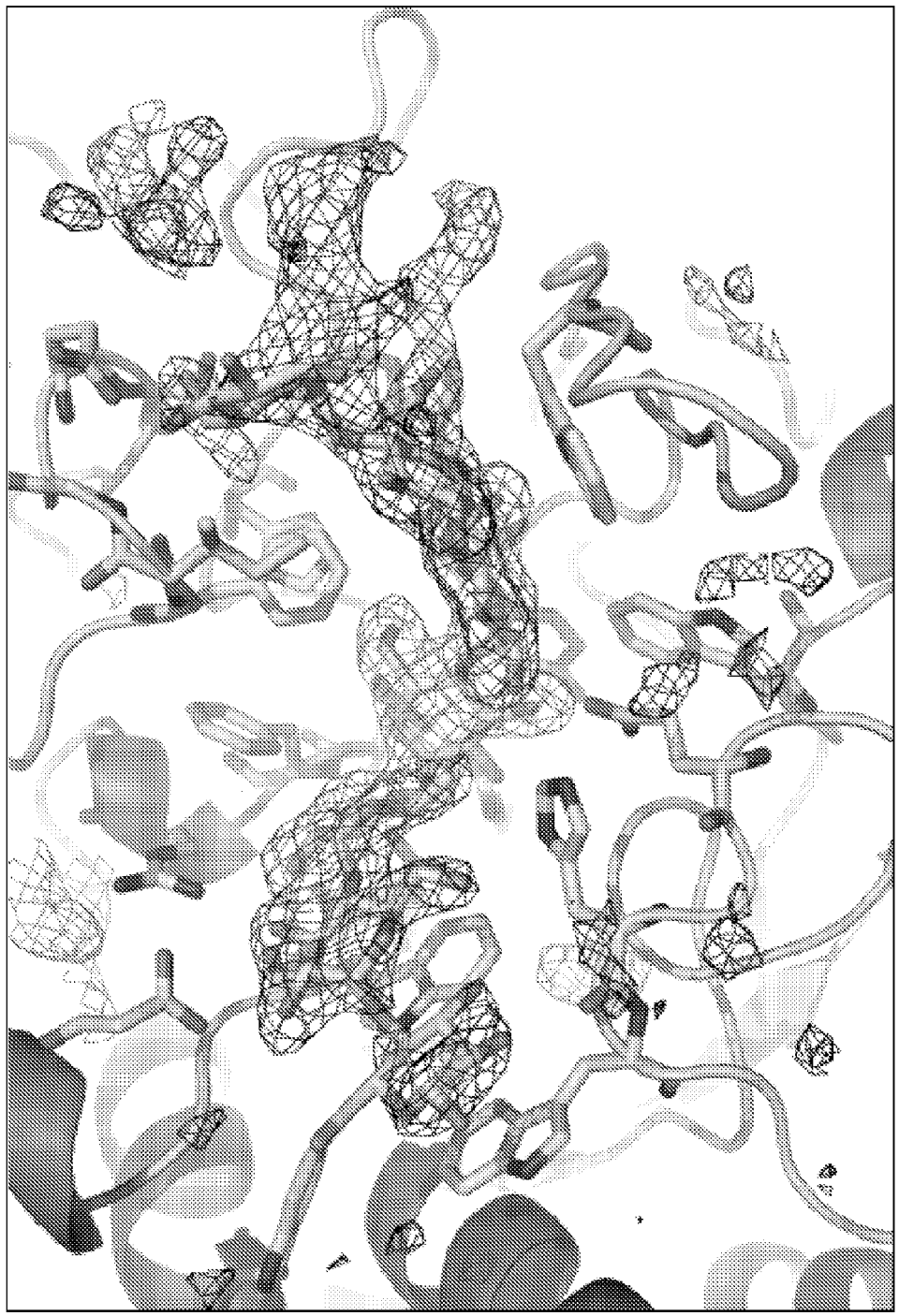
FIG. 8 depicts the crystal structure of PS4 with acarbose bound.

Enzyme-inhibitor interactions were analyzed and characterized using the Chemical Computing Group (Montreal, Canada) Molecular Operating Environment (MOE) program, according to the parameters and instructions supplied with the program. Inhibitor binding to PS4 is depicted at FIG. 8. The nomenclature for sugar binding sub-sites of the enzyme is that of Davies et al. *Biochem J.* 321: 661-72 (1997) and is superimposed on the depiction of the bound inhibitor in FIG. 9. The inhibitor was found in a deep cleft in the surface of the molecule, at the C-terminal end of the ($\beta/\alpha$)8 barrel. Inspection of difference Fourier maps of data collected from native crystals of PS4 and crystals soaked for 24 hours with acarbose revealed a very clear and continuous difference density for at least seven sugar residues bound to the −4 to +3 sugar sub-sites in the enzyme active-site. This indicates that crystalline PS4 reacts with acarbose, resulting in a transglycosylation product that binds across the active-site of the enzyme. The nature of the transglycosylated inhibitor was deduced by the presence or absence of difference density for O6 atoms and the conformation of the sugar rings. The difference density for an O6 atom was evident at the +3, +2, −1, −2, −3, and 4 sugars, but not at the +1 sugar. Additionally, the sugars at +3, +2, −2, −3, and −4 had the chair conformation, indicating that glucose residues were bound at these sugar sub-sites. At the −1 sugar sub-site, the sugar was in a boat conformation, indicating that it is the cyclitol sugar. At the +1 sugar sub-site, the chair conformation and lack of a difference density for an O6 atom indicated that this sugar is the dideoxy sugar. The boat conformation of the cyclitol sugar resulted in a distinct bend in the inhibitor. The only clear differences in the structure of the protein with and without bound inhibitor were changes in the conformation of Glu 219 and Asp 294 and displacement of water molecules upon inhibitor binding.

Example 7

Conformation of the Inhibitor at the Non-Reducing End

A bifurcation in the positive difference density in the Fo-Fc difference map was seen when the data obtained for PS4 without inhibitor was refined to the data obtained with the bound inhibitor. In the −4 sugar conformation, there was a positive density corresponding to the C1, O1, C3, O3, and O6 atoms, but not the C2, O2, C4, O5, and C6 atoms. See FIG. 9. This information revealed that there were apparently two conformations of the −4 sugar. The first conformation corresponded to exo-specificity, as seen in the *P. stutzeri* enzyme. See Hasegawa et al., *Protein Eng.* 12: 819-24 (1999). The second conformation appeared to correspond to endo-specificity, as no recognition of the reducing end of the inhibitor was seen.

Example 8

Enzyme/Inhibitor Interactions

The types of interactions between the PS4 enzyme and the inhibitor can be divided into hydrogen bonding, hydrophobic interactions, and water-mediated interactions. There were 20 hydrogen bonds between the protein and the inhibitor. The conserved GH13 catalytic residues, D193, E219, and D294, were found clustered around the −1 and +1 sugars. See FIG. 9 The side-chain positions of E219 and D294 were slightly different from the native structure, and likely are due to small conformational changes induced by inhibitor binding. The OE2 of E219 was 2.7 Å from the nitrogen atom of the inhibitor, which mimicked the oxygen atom of the glycosidic bond. The OD2 of D194 formed a hydrogen bond to the O6 of the −1 sugar. The third invariant acidic amino-acid, D294, hydrogen bonded to the O2 and O3 hydroxyls of the −1 sugar in a bidentate interaction.

Enzyme recognition of the −4 sugar at the non-reducing end of the inhibitor occurred via hydrogen bonding between (1) the side chain carboxylate oxygen OE1 of E160 and the O1 and O6 of the −4 sugar residue, (2) the O6 of S161 and the O6, and (3) the main-chain nitrogen of G 58 to O1 of the same sugar residue. Other key hydrogen bond interactions were hydrogen bonds between the backbone carbonyl oxygen of H307 and the O3 oxygen of the +3 sugar, OE2 of E226 and O1 of +2 sugar, NH1 of R196 and O3 of the −1 sugar, OE1 of E219 and O2 of the −1 sugar, NE2 of H293 to O3 of the −1 sugar, and OE1 of Q305 to O2 of the −2 sugar. See FIG. 9.

Five water molecules mediated further hydrogen bonds from the protein to the inhibitor. In the crystal structure, $H_2O$ number 456 hydrogen bonded to the $O_2$ and O3 of the +1 sugar, the backbone carbonyl oxygen atom of E219, and the backbone nitrogen atom of W221. $H_2O$ number 464 hydrogen bonded to the O5 and O6 of the −3 sugar, the O6 of the −2 sugar, and the O6 of 564. $H_2O$ number 472 hydrogen bonded to the O6 of the −2 sugar, the NE1 of W66, and OE1 of E76. $H_2O$ number 516 hydrogen bonded to the O6 of the −2 sugar, the OD2 of D62, and the OE1 of E76. See FIG. 9.

There were nine significant hydrophobic interactions. Of these, four were co-planar stacking interactions between sugar residues +3, +2, −1, and −3 with W308, W221, Y78 and W66, respectively. There were four additional non-planar interactions of the inhibitor with W25, F79, F156, I157, and F194. Notably, F156 and I157 formed a hydrophobic peninsula around which the inhibitor wraps, allowing its non-reducing end to hydrogen bond to the protein. See FIG. 9.

Example 9

Altering the Exo- and Endo-Activity of PS4 by Protein Engineering

Enzymes with exo-activity generally have an active-site cleft that is blocked at one end, only allowing substrate binding at the ends of macromolecular chains. In PS4, the non-reducing end of the active-site was restricted by the large loop between S64 and G75, but it was not completely blocked. There was indeed sufficient space for an amylose chain to pass between this loop and the loop formed by residues 155-163. In PS4, the exo-amylase activity appeared to be driven by hydrogen bonding of the non-reducing end of the amylose chain to G158, E160, and S161, which was very similar to that seen in the *P. stutzeri* G4-amylase. Given the total number of interactions between the substrate, as mimicked by the enzyme inhibitor complex, the energy involved in recognition of the non-reducing end of the amylase chain appeared small compared to the total energy involved in binding, amounting to only four hydrogen bonds out of a total of 23, as well as four coplanar stacking interactions. The F(acarbose)–F(native) difference map showed two conformations for the inhibitor at the non-reducing end. Together this suggested that the hydrogen bonding to the non-reducing end of the amylose chain was insufficiently strong to provide for 100% exo-specificity, which was reported in the enzymological characterization of the enzyme. Thus, the crystal structure of an inhibitor complex of PS4 provided additional evidence for mixed exo- and endo-cleavage of starch by this enzyme. This further suggested that protein engineering can be used to alter the exo- and endo-activity of the enzyme, and thus the products of the reaction.

Example 10

Site-Directed Mutagenesis

Site-directed mutagenesis was used to produce PS4 variants. Representative examples of PS4 variants having single amino acid substitutions are shown in TABLE 3. Mutations were introduced into a nucleic acid encoding the PS4 enzyme, using the Quick Change™ method (Stratagene, Calif.), according to instructions supplied with the kit with some modifications. Briefly, a single colony was picked and inoculated in 3 ml LB (22 g/l Lennox L Broth Base, Sigma) supplemented with 50 µg/ml kanamycin (Sigma) in a 10 ml Falcon tube. After overnight incubation at 37° C. at 200 rpm, the culture was spin down at 5000 rpm for 5 min. The medium was removed and the double-stranded DNA template was prepared using QIAGEN columns (QIAGEN). Primers were designed according to the manufacturers' protocol. For example, TABLE 5 lists primers that were used to generate backbone pMS382 based on the sequence of PS4 as shown in SEQ ID NO: 1 or 2; and TABLE 6 lists primers that were used to generate variants of pMS382 at position E223.

Next, PCR was performed to synthesize the mutant strand. The PCP reaction mix contained the following:

| | |
|---|---|
| 2.5 µl | 10 X QuickChange Multi reaction buffer |
| 0.75 µl | QuickSolution |
| X µl | primers (10 pmol for primers of 28-35 nt; 7 pmol for primers of 24-27 nt; or 5 pmol for primers of 20-23 nt) |
| 1 µl | dNTP mix |
| X µl | ds-DNA template (200 ng) |
| 1 µl | QuickChange Multi enzyme blend (2.5 U/µl) (PfuTurbo DNA polymerase) |
| X µl | $dH_2O$ (to a final volume of 25 µl) |

The PCR reaction was performed in an Eppendorf thermal cycler for 35 cycles of denaturation (96° C. for 1 min), primer annealing (62.8° C. for 1 min), and elongation (65° C. for 15 min), and then hold at 4° C. For each amplification reaction, 2 µl of DpnI restriction enzyme (10 U/µl) was added, and the mixture was incubated at 37° C. for ~3 hr.

The DpnI-treated DNA was then used to transform XL10-Gold® Ultracompetent cells (Stratagene). XL10-Gold® cells were thawed on ice. For each mutagenesis reaction, 45 µl cells were added to a pre-chilled Falcon tube. Subsequently, 2 µl of beta-mercaptoethanol mix was added to each tube. The mixture was incubated on ice for 10 min with swirling every 2 min. Then, 1.5 µl DpnI-treated DNA was added to each aliquot of cells, and the mixture was incubated on ice for 30 min. The sample was subject to a heat-pulse of 30 sec at 42° C., and was placed on ice for another 2 min. 0.5 ml of preheated $NZY^+$ broth was added to each sample, and incubation was carried at 37° C. for 1 hr with shaking at 225-250 rpm. 200 µl of each transformation reaction were plated on LB plates (33.6 g/l Lennox L Agar, Sigma) supplemented with 1% starch and 50 µg/ml kanamycin. The plates were incubated overnight at 37° C. Individual colonies harboring the desired mutations were identified by DNA sequencing and subjected to plasmid preps to harvest plasmids with the desired mutations.

Transformation into *Bacillus subtilis*.

*Bacillus subtilis* (strain DB104A; Smith et al., *Gene* 70, 351-361 (1988)) is transformed with the mutated plasmid DNA according to the following protocol.

A. Media for Protoplasting and Transformation

| 2 x SMM | per liter: 342 g sucrose (1M); 4.72 g sodium maleate (0.04M); 8.12 g $MgCl_2 \cdot 6H_2O$ (0.04M); pH 6.5 with concentrated NaOH. Distribute in 50-ml portions and autoclave for 10 min. |
|---|---|
| 4 x YT(½ NaCl) | 2 g Yeast extract + 3.2 g Tryptone + 0.5 g NaCl per 100 ml. |
| SMMP | mix equal volumes of 2 x SMM and 4 x YT. |
| PEG | 10 g polyethyleneglycol 6000 (BDH) or 8000 (Sigma) in 25 ml 1 x SMM (autoclave for 10 min.). |

B. Media for Plating/Regeneration

| agar | 4% Difco minimal agar. Autoclave for 15 min. |
|---|---|
| sodium succinate | 270 g/l (1M), pH 7.3 with HCl. Autoclave for 15 min. |
| phosphate buffer | 3.5 g $K_2HPO_4$ + 1.5 g $KH_2PO_4$ per 100 ml. Autoclave for 15 min. |
| $MgCl_2$ | 20.3 g $MgCl_2 \cdot 6H_2O$ per 100 ml (1M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |

DM3 regeneration medium: mix at 60° C. (water bath; 500-ml bottle):

250 ml sodium succinate
50 ml casamino acids
25 ml yeast extract
50 ml phosphate buffer
15 ml glucose
10 ml $MgCl_2$
100 ml molten agar Add appropriate antibiotics: chloramphenicol and tetracycline, 5 μg/ml; erythromycin, 1 μg/ml. Selection on kanamycin is problematic in DM3 medium: concentrations of 250 μg/ml may be required.

C. Preparation of Protoplasts

Use detergent-free plastic or glassware throughout.

Inoculate 10 ml of 2×YT medium in a 100-ml flask from a single colony. Grow an overnight culture at 25-30° C. in a shaker (200 rev/min).

Dilute the overnight culture 20 fold into 100 ml of fresh 2×YT medium (250-ml flask) and grow until $OD_{600}=0.4\text{-}0.5$ (approx. 2 h) at 37° C. in a shaker (200-250 rev/min).

Harvest the cells by centrifugation (9000 g, 20 min, 4C).

Remove the supernatant with pipette and resuspend the cells in 5 ml of SMMP+5 mg lysozyme, sterile filtered.

Incubate at 37° C. in a waterbath shaker (100 rpm).

After 30 min and thereafter at 15 min intervals, examine 25 μl samples by microscopy. Continue incubation until 99% of the cells are protoplasted (globular appearance). Harvest the protoplasts by centrifugation (4000 g, 20 min, RT) and pipet off the supernatant. Resuspend the pellet gently in 1-2 ml of SMMP.

The protoplasts are now ready for use. Portions (e.g. 0.15 ml) can be frozen at −80° C. for future use (glycerol addition is not required). Although this may result in some reduction of transformability, 106 transformants per ug of DNA can be obtained with frozen protoplasts).

D. Transformation

Transfer 450 μl of PEG to a microtube.

Mix 1-10 μl of DNA (0.2 μg) with 150 μl of protoplasts and add the mixture to the microtube with PEG. Mix immediately, but gently.

Leave for 2 min at room temperature, and then add 1.5 ml of SMMP and mix.

Harvest protoplasts by microfuging (10 min, 13,000 rpm (10,000-12,000 g)) and pour off the supernatant. Remove the remaining droplets with a tissue.

Add 300 μl of SMMP (do not vortex) and incubate for 60-90 min at 37° C. in a waterbath shaker (100 rpm) to allow for expression of antibiotic resistance markers. (The protoplasts become sufficiently resuspended through the shaking action of the waterbath.) Make appropriate dilutions in 1×SSM and plate 0.1 ml on DM3 plates Fermentation of PS4 Variants in Shake Flasks.

The shake flask substrate is prepared by dissolving the following in water:

| Yeast extract | 2% (w/v) |
|---|---|
| Soy Flour | 2% (w/v) |
| NaCl | 0.5% (w/v) |
| Dipotassium phosphate | 0.5% (w/v) |
| Antifoam agent | 0.05% (w/v). |

The substrate is adjusted to pH 6.8 with 4 N sulfuric acid or sodium hydroxide before autoclaving. 100 ml of substrate is placed in a 500 ml flask with one baffle and autoclaved for 30 minutes. Subsequently, 6 ml of sterile dextrose syrup is added. The dextrose syrup is prepared by mixing one volume of 50% w/v dextrose with one volume of water followed by autoclaving for 20 minutes.

The shake flasks are inoculated with the variants and incubated for 24 hours at 35° C. and 180 rpm in an incubator. After incubation cells are separated from broth by centrifugation (10.000 g in 10 minutes) and finally, the supernatant is made cell free by microfiltration at 0.2 μm. The cell free supernatant is used for assays and application tests.

Enzymatic Characterization of PS4 Variants.

Exo-amylase activity of PS4 variants produced by mutagenesis was assayed using the Betamyl® assay (Megazyme, Ireland). One Betamyl unit is defined as activity degrading 0.0351 mole/min of PNP-coupled maltopentaose. The assay contained 50 μL of 50 mM sodium citrate, 5 mM calcium chloride, pH 6.5, and 25 μL of Betamyl substrate. The assay mixture was incubated for 30 min at 40° C., then stopped by the addition of 150 μL of 4% Tris. Absorbance at 420 nm was measured using an ELISA-reader, and the Betamyl activity was calculated according to the formula Activity=A420×d in Betamyl units/ml of enzyme sample assayed, with "d" being the dilution factor of the enzyme sample. Endo-amylase activity was determined using the Phadebas blue assay (Pharmacia and Upjohn Diagnostics AB), performed according to the manufacturer's instructions. The exo-activity index is the ratio of Betamyl activity to Phadebas activity. The wild-type PS4 had a Betamyl/Phadebas activity ratio of 50. Variants with ratios lower than 50 are more endo-specific than the wild-type. Those with a ratio greater than 50 are more exo-specific. The Betamyl and Phadebas activity measured for the PS4 variants and their ratios of Betamyl to Phadebas activity are listed in TABLE 7.

The mutations in the above TABLE 7 are listed with reference to the sequence of the respective backbone that is noted at the upper left corner of each table. "Na-Acet." stands for sodium acetate; "Na-citr." stands for sodium citrate; 72, 75, 80, or 85 indicates the temperature in ° C. at which the half-lives have been determined as described in Example 1; "Beta" stands for the Betamyl activity as described in Example 10; "Phad" stands for the Phadebas activity as described in Example 10; and "B/P" stands for the ratio of Betamyl activity to Phadebas activity.

Example 11

Protein Engineering of PS4

Active site residues close to the hydrolyzed glycosidic bond between the +1 and −1 residues were not mutated, as changes to these residues would be expected to affect the catalytic reaction itself, rather than the degree of exo-specificity. See FIG. 9. The residues W66, I157, E160, S161, R196, W221, K222, H307, and W308, were targeted for mutagenesis and characterization, based on the enzyme inhibitor complex information disclosed above. K222 is part of a salt-bridge network that includes R196 and E226, which interact with the substrate. These residues were chosen for mutagenesis, as changes to these residues may alter substrate binding. Mutant libraries of the whole PS4 protein also were prepared, using error-prone PCR libraries of the gene, made according to procedures well known in the art.

Mutations to the −4 Binding-Site.

An analysis of the mutant E160D revealed no effect on the Betamyl/Phadebas activity ratio. To test if exo-activity required non-reducing sugar recognition by residue 160, the mutant E160G also was made. In this case, the Betamyl/Phadebas ratio was 12, representing a significant increase in endo-activity. Confirmation that an E or D at residue 160 was critical for exo-specificity was confirmed by the mutations of E160 to P, F, R, S, and L, which significantly increased endo-specificity. This clearly demonstrated the requirement of recognition of the non-reducing end sugar by E/D160 for exo-specificity. The mutation S161A likewise had a significant effect on endo-activity, with a Betamyl/Phadebas ratio of 18.

Mutations to the −3 Binding-Site.

Five mutations of W66 were obtained. The conservative mutations to L, V, F, and M had little effect on exo-specificity. The mutation W66S, however, increased exo-specificity and exhibited a lower expressed activity.

Mutations to the −2 Binding Site.

Three mutations to Q305 were made. Mutations Q305T and Q305L reduced exo-specificity significantly. By contrast, Q305E had no appreciable effect on exo-specificity.

Mutations to the +2 Binding-Site.

Three mutations at R196 exhibited a large increase in exo-specificity. R196V had greatest exo-specificity, followed by R196H and R196P. The mutant H307L had a similar exo-specificity to these R196 mutants.

Mutations to the +3 Binding-Site.

Mutations to W221 had very low expressed activity. Only W221A had sufficient expressed activity for characterization, and it had modestly increased exo-activity. Four mutations to W308, W308A, W308S, W308L and W308S, had significant expressed activity. All four mutations showed significant improvement in exo-specificity, the best being W308S.

The mutation K222T exhibited the most exo-activity. The side-chain of K222 did not interact directly with the substrate, yet mutation of this residue gave the largest positive increase in exo-specificity. The increase in exo-activity was not likely an effect on the neighboring W221, as mutation of W221 had only a modest effect on specificity. An analysis of the region around K222 revealed that it was part of an ion-pair network. K222 ion-paired with D254, which also ion-paired with R196. R196 in turn ion-paired with E226. R196 was positioned to hydrogen bond with the O2 and O3 of the +2 sugar. E226 hydrogen bonded to the +2 sugar. Accordingly, the large increase in exo-specificity of the K222T mutation may be due to a simultaneous reorientation of R196 and E226, which weakens substrate binding to the +2 sugar.

In summary, mutations to the − binding sub-sites increased the endo-specificity of the enzyme. The data also revealed that mutations to the + binding sub-sites could greatly increase exo-specificity. Strong interactions between the substrate binding-site and the amylose chain end promoted exospecificity. Similarly, weakening these interactions increased the endo-specificity of the enzyme. The effect of mutations to the "+" binding sub-sites revealed a delicate balancing of interactions throughout the substrate binding-site. Further, the relative strength of substrate interactions in the − binding sub-sites versus the strength of interactions in the + binding sub-sites determined the degree of exo-specificity of the enzyme. Changes that decrease the affinity of the "−" binding sub-sites relative to the + binding sub-sites increased endo-specificity. Conversely, changes that decrease the affinity of the + binding sub-sites relative to the − binding sub-sites increased exo-specificity.

It will be apparent to those skilled in the art that various modifications and variation can be made to the compositions and methods of using the same without departing from the spirit or scope of the intended use. Thus, it is the modifications and variations provided they come within the scope of the appended claims and their equivalents.

TABLE 3

Single amino acid substitutions in representative PS4 variants.

| A3S | G70D | V113I | G134C | G158T | A179N | G223P | W232P | G303L | R316P |
|---|---|---|---|---|---|---|---|---|---|
| A3T | G70K | N116D | R137C | G158F | A179R | G223I | W232Q | G303E | R316K |
| P7S | G70E | N119S | N138D | G158P | A179E | G223L | W232R | G303D | W323M |
| A8N | G70S | N119G | N138E | G158I | A179T | G223V | W232S | Q305E | T324L |
| G9A | G70Q | N119Y | N138S | G158A | R182S | G223C | W232Y | Q305T | T324M |
| H13R | G70A | N119E | C140R | G158V | R182H | G223T | W232T | Q305L | T324A |
| N26E | G70V | G121W | C140A | G158L | R182M | G223S | R233H | H307D | S325G |
| N26D | G70L | G121A | A141S | G158Q | R182D | G223Y | N234R | H307L | S334R |
| P32S | G70P | G121F | A141P | G158C | R182G | G223W | A236E | H307R | S334Q |
| N33Y | K71R | G121L | D142N | E160D | S183G | G223Q | S237G | H307K | S334H |
| D34N | K71M | G121T | D142G | S161V | G184Q | G223N | S237D | H307G | S334A |
| I38M | S72E | G121S | D142E | S161A | G188A | G223D | W238Q | H307P | S334M |
| I46F | S72K | G121E | P143T | S161T | G188H | G223H | W238G | H307I | S334L |
| D49V | S72N | G121K | G144E | S161K | G188T | G223K | W238K | H307S | S334P |
| D62N | S72T | G121R | N145D | S161P | G188S | G223R | W238R | H307M | H335M |

TABLE 3-continued

Single amino acid substitutions in representative PS4 variants.

| | | | | | | | | | |
|---|---|---|---|---|---|---|---|---|---|
| F63L | G73M | G121H | N145S | S161G | F192Y | G223M | W238P | H307Q | W339E |
| F63A | G73S | G121M | Y146G | S161R | F192F | G223A | W238E | H307V | W339A |
| F63D | G73T | G121V | Y146E | S161H | F192M | G223E | Q239L | H307W | Y341E |
| F63E | G73N | G121P | Y146D | L163M | V195D | G223F | V253G | H307Y | Y341C |
| F63V | G73L | G121I | N148S | N164R | R196P | D255V | A257V | H307C | D343E |
| S64T | G73E | G121D | N148K | G166N | R196Q | S225G | E260R | H307F | R353T |
| S64N | G73D | Y122W | D149V | P168L | R196T | S225V | E260K | H307E | R358A |
| T67V | G74S | Y122A | D149L | Q169R | R196K | E226W | N264D | W308C | R358T |
| T67K | G75C | Y122Q | D149H | Q169K | R196Y | E226C | V267I | W308T | R358L |
| T67Q | G75S | Y122E | C150A | Q169V | R196S | E226D | D269V | W308K | R358V |
| T67H | G75R | P123S | D151W | Q169G | R196G | E226G | D269S | W308N | R358Q |
| T67R | G75Y | D124S | D151A | Q169E | R196A | Y227G | D269N | W308R | R358E |
| T67G | G75F | K125E | D151V | Q169N | R196V | Y227T | K271L | W308S | R358N |
| T67N | G75W | K125G | G153D | Q169D | Y198W | Y227D | K271Q | W308G | R358G |
| D68C | G75G | K125A | S334T | I170M | Y198F | Y227K | W308Q | S367R |
| D68E | E76V | K125W | S334T | I170E | A199P | Y227C | K271L | W308A | S367Q |
| G69M | G100A | K125D | G153A | I170L | P200G | S229N | H272Q | A309T | S379G |
| G69I | G100S | K125Q | D154G | I170K | P200A | S229P | G276R | A309E | D390E |
| G69H | G104R | K125P | D154E | I170N | R202K | W232F | W282S | A309M | S399P |
| G69E | G104N | E126N | D154Y | L178W | S208T | W232G | V285A | A309V | S420G |
| G69A | G106K | E126D | F156Y | L178W | S213N | W232H | V290I | A309I | D422N |
| G69R | V107M | N128E | I157L | L178Q | L220A | W232I | T295C | A309P | D422Q |
| G69F | L110F | P130S | I157V | L178F | L220T | W232K | Y297H | D312E | D422P |
| G69T | D112E | A131T | I157M | A179P | K222Y | W232L | G300E | R316Q | G424S |
| G69K | | G134R | G158S | A179S | K222M | W232N | N302K | R316S | G424D |

TABLE 4

| Backbone | Mutations |
|---|---|
| J2 | V113I, G134R, A141P, I157L, Y198F, G223A, V290I, H307L, S334P, D343E |
| d3 | N33Y, D34N, K71R, G134R, A141P, I157L, L178F, A179T, G223A, H307L, S334P, D343E |
| pMD3 | N33Y, D34N, G121D, G134R, A141P, I157L, L178F, A179T, G223A, H307L, S334P |
| pMD55 | N33Y, D34N, G121F, G134R, A141P, I157L, L178F, A179T, G223A, H307L, S334P |
| pMD74 | N33Y, D34N, G121A, G134R, A141P, I157L, L178F, A179T, G223A, H307L, S334P |
| pMD85 | N33Y, D34N, G121F, G134R, A141P, I157L, L178F, A179T, G223E, H307L, S334P |
| pMD86 | N33Y, D34N, G121A, G134R, A141P, I157L, L178F, A179T, G223E, H307L, S334P |
| pMD96 | N33Y, D34N, G121F, G134R, A141P, I157L, S161A, L178F, A179T, G223E, H307L, S334P |
| pMD153 | N33Y, D34N, G121F, G134R, A141P, Y146G, I157L, G158T, S161A, L178F, A179T, G223E, S229P, H307L, A309P, S334P |
| pMD153d1 | N33Y, D34N, G121F, G134R, A141P, Y146G, I157L, G158T, S161A, L178F, A179T, G223E, S229P, H307L, A309P, S334P |
| pMD172 | N33Y, D34N, G121F, G134R, A141P, Y146G, I157L, S161A, L178F, A179T, G223E, S229P, G303E, H307L, A309P, S334P |
| pMD212 | N33Y, D34N, G70D, G121F, G134R, A141P, N145D, Y146G, I157L, G158T, S161A, L178F, A179T, G223E, S229P, H307L, A309P, S334P, W339E |
| pMD230 | N33Y, D34N, G121F, G134R, A141P, N145D, Y146G, I157L, S161A, L178F, A179T, G223E, S229P, H272Q, G303E, H307L, A309P, S334P |
| pMD248 | N33Y, D34N, G121F, G134R, A141P, N145D, Y146G, I157L, L178F, A179T, G223E, S229P, H272Q, G303E, H307L, S334P |
| pMD253 | N33Y, D34N, G121D, G134R, A141P, Y146G, I157L, L178F, A179T, G223E, S229P, H272Q, G303E, H307L, A309P, S334P |
| pMS281 | N33Y, G121F, G134R, A141P, N145D, Y146G, I157L, S161A, L178F, A179T, G223F, S229P, H272Q, H307L, A309P, S334P |
| pMS284 | N33Y, D34N, G121F, G134R, A141P, Y146G, I157L, S161A, L178F, A179T, G223E, S229P, H272Q, G303E, H307L, A309P, S334P |
| pMS292 | N33Y, D34N, G121F, G134R, A141P, N145D, Y146G, I157L, S161A, L178F, A179T, G223F, S229P, H272Q, H307L, A309P, S334P |
| pMS382 | N33Y, D34N, G70D, G121F, G134R, A141P, Y146G, I157L, S161A, L178F, A179T, G223E, S229P, H307K, A309P, S334P |
| pMS382d1 | N33Y, D34N, G70D, G121F, G134R, A141P, Y146G, I157L, S161A, L178F, A179T, G223E, S229P, H307K, A309P, S334P |

TABLE 5

Primers used for pMS382 backbone.

| SEQ ID NO: | Mutation | 5' Oligo Sequence 3' | modification | Strand | Purpose |
|---|---|---|---|---|---|
| 9 | N33Y, D34N | GCGAAGCGCCCTACAACTGGTACAAC | 5' phosphate | (+) | MSDM |
| 10 | G70K | CTGGACGGATGGAgatAAAAGCGGAGGCGGC | 5' phosphate | (+) | MSDM |
| 11 | G121F | CCAATCACATGAACCGCttcTACCCGGACAAGGAG | 5' phosphate | (+) | MSDM |

TABLE 5-continued

Primers used for pMS382 backbone.

| SEQ ID NO: | Mutation | 5' Oligo Sequence 3' | modification | Strand | Purpose |
|---|---|---|---|---|---|
| 12 | G134R | CTGCCGGCCGGCCAGcGCTTCTGGCG | | (+) | SDM |
| 13 | G134R- | cgccagaagcgctggccggccggcag | | (−) | SDM |
| 14 | A141P | CGCAACGACTGCGCCGACCCGGG | 5' phosphate | (+) | MSDM |
| 15 | Y146G | GATCCGGGCAACggcCCCAACGACTGCG | 5' phosphate | (+) | MSDM |
| 16 | I157L | GACGGTGACCGCTTCcTgGGCGGCGAGTCG | | (+) | SDM |
| 17 | I157L- | cgactcgccgcccaggaagcggtcaccgtc | | (−) | SDM |
| 18 | S161A | GGGCGGCGAGgcgGACCTGAACA | 5' phosphate | (+) | MSDM |
| 19 | L178F, A179T | CGCGACGAGTTTACCAACCTGCG | 5' phosphate | (+) | MSDM |
| 20 | G223E (gag) | GGCGAGCTGTGGAAAGDNCCTTCTGAATATCCGAG | 5' phosphate | (+) | MSDM |
| 21 | S229P | GCCTTCTGAATATCCGccgTGGGACTGGCGCAAC | 5' phosphate | (+) | MSDM |
| 22 | L307K | CAAAATGAAGGACAACATaaaTGGCCGCTTCAAGATGGCC | 5' phosphate | (+) | MSDM |
| 23 | A309P | GCACCTGTGGccgCTGCAGGACG | 5' phosphate | (+) | MSDM |
| 24 | S334P, D343E | GTACTGGccgCACATGTACGACTGGGGCTACGGCgaaTTCATC | | (+) | SDM |
| 25 | S334P, D343E- | gatgaattcgccgtagccccagtcgtacatgtgcggccagtac | | (−) | SDM |
| 26 | E343D | GGGCTACGGCGACTTCATCCGCCAG | 5' phosphate | (+) | MSDM |

TABLE 6

Primers used to generate PS4 variants of pMS382 at position E223.

| SEQ ID NO: | Mutation | 5' Oligo Sequence 3' | modification | Strand | Purpose |
|---|---|---|---|---|---|
| 27 | E223A | CGTCGGCGAACTTTGGAAAgcaCCGAGCGAATATCCGC | 5' phosphate | (+) | MSDM |
| 28 | E223G | CGGCGAACTTTGGAAAggaCCGAGCGAATATCCG | 5' phosphate | (+) | MSDM |
| 29 | E223S | CGTCGGCGAACTTTGGAAAagcCCGAGCGAATATCCGC | 5' phosphate | (+) | MSDM |
| 30 | E223K | GGCGAACTTTGGAAAaaaCCGAGCGAATATCCGCC | 5' phosphate | (+) | MSDM |
| 31 | E223I | CGTCGGCGAACTTTGGAAAatcCCGAGCGAATATCCGC | 5' phosphate | (+) | MSDM |
| 32 | E223L | CGTCGGCGAACTTTGGAAActgCCGAGCGAATATCCGC | 5' phosphate | (+) | MSDM |
| 33 | E223V | GGCGAACTTTGGAAAgtcCCGAGCGAATATCCGCC | 5' phosphate | (+) | MSDM |
| 34 | E223F | CGTCGGCGAACTTTGGAAAtttCCGAGCGAATATCCGC | 5' phosphate | (+) | MSDM |

TABLE 6-continued

Primers used to generate PS4 variants of pMS382 at position E223.

| SEQ ID NO: | Mutation | 5' Oligo Sequence 3' | modification | Strand | Purpose |
|---|---|---|---|---|---|
| 35 | E223C | CGTCGGCGAACTTTGGAAAtgcCCGAGCGAATATCCGC | 5' phosphate | (+) | MSDM |
| 36 | E223P | GGCGAACTTTGGAAAccgCCGAGCGAATATCCGCC | 5' phosphate | (+) | MSDM |
| 37 | E223T | CGTCGGCGAACTTTGGAAAacgCCGAGCGAATATCCGC | 5' phosphate | (+) | MSDM |
| 38 | E223Y | CGTCGGCGAACTTTGGAAAtatCCGAGCGAATATCCGC | 5' phosphate | (+) | MSDM |
| 39 | E223W | CGTCGGCGAACTTTGGAAAtggCCGAGCGAATATCCGC | 5' phosphate | (+) | MSDM |
| 40 | E223Q | GGCGAACTTTGGAAAcagCCGAGCGAATATCCGCC | 5' phosphate | (+) | MSDM |
| 41 | E223N | GGCGAACTTTGGAAAaacCCGAGCGAATATCCGCC | 5' phosphate | (+) | MSDM |
| 42 | E223D | CGGCGAACTITGGAAAgatCCGAGCGAATATCCG | 5' phosphate | (+) | MSDM |
| 43 | E223H | GGCGAACTTTGGAAAcatCCGAGCGAATATCCGCC | 5' phosphate | (+) | MSDM |
| 44 | E223R | GGCGAACTTTGGAAAagaCCGAGCGAATATCCGCC | 5' phosphate | (+) | MSDM |
| 45 | E223M | CGTCGGCGAACTTTGGAAAatgCCGAGCGAATATCCGC | 5' phosphate | (+) | MSDM |

TABLE 7

| J2 | Mutation | | | | Na-citr. pH 6.5 | | | | |
|---|---|---|---|---|---|---|---|---|---|
| ID | 1 | 2 | 3 | 4 | 72 | 75 | Betamyl | Phad | B/P |
| J2 avg. | | | | | 4.2 | 1.1 | | | |
| S304 | D34N | G188A | | | | | 144 | ND | ND |
| SSM93 A12 | K71R | D269S | | | 5.3 | 1.6 | 108 | 3.16 | 34 |
| SSM59 E4 | N234R | V285A | S420G | | 5.9 | 1.9 | 107 | 3.00 | 36 |
| SSM91 E10 | D269V | | | | 4.4 | 1.5 | 105 | 2.97 | 35 |
| SSM84 G4 | K271L | S325G | S420G | G424S | | 2.2 | 40 | 0.73 | 55 |
| SSM83 H7 | K271Q | | | | 5.6 | 2.1 | 116 | 2.60 | 45 |
| SSM85 A8 | K271A | | | | 4.4 | 2.6 | 114 | 2.26 | 50 |
| SSM52 G11 | S379G | | | | 5.0 | 1.5 | 94 | 2.77 | 34 |
| SSM90 C11 | S420G | | | | 5.0 | 1.7 | 149 | 3.54 | 42 |

| d3 | Mutation | | | | Na-citr. pH 6.5 | | | | | |
|---|---|---|---|---|---|---|---|---|---|---|
| ID | 1 | 2 | 3 | 4 | 72 | 75 | 80 | Betamyl | Phad | B/P |
| d3 avg | | | | | 24.8 | 8.9 | 2.9 | 336 | 10 | 35 |
| SSM144 G2 | D49V | G121R | Q169R | A374V | | | | 27 | 0.41 | 67 |
| MG044 | G106K | | | | | | 3.0 | 339 | 7.57 | 45 |
| SSM134 C10 | V107M | G121S | | | | 9.1 | 3.0 | 103 | 1.38 | 75 |
| MG042 | G121W | D112E | | | | | | 27 | 0.17 | 157 |
| SSM142 E7 | 121S | P130S | D142N | | | | 0.9 | 41 | 0.48 | 85 |
| SSM142 E10 | G121A | P141S | | | | | 0.6 | 60 | 0.37 | 164 |
| SSM142 E10 | G121A | P141S | | | | 1.6 | 0.7 | 63 | 0.36 | 175 |
| SSM142 C9 | G121F | | | | 12.6 | 4.6 | | 136 | 2.34 | 58 |
| SSM142 C9 | G121F | | | | | | | 220 | 3.75 | 59 |
| MG041 | G121L | | | | | | 2.4 | 195 | 3.47 | 56 |
| SSM142 E4 | G121T | | | | | | 0.0 | 22 | 0.10 | 220 |
| SSM142 C9 | G121F | | | | | | | 164 | 3.17 | 52 |
| SSM144 C4 | G121S | | | | | | 2.7 | 188 | 2.72 | 69 |
| SSM144 D1 | G121E | | | | | | 2.4 | 268 | 4.42 | 61 |

TABLE 7-continued

| ID | Mutation 1 | Mutation 2 | Mutation 3 | 75 | 80 | 75 | 80 | Betamyl | Phad | B/P |
|---|---|---|---|---|---|---|---|---|---|---|
| SSM144 D3 | G121K | | | | 2.2 | | | ND | ND | ND |
| SSM144 D3 | G121K | | | | 2.0 | | | 243 | 3.97 | 61 |
| MG047 | A131T | G303L | | | 2.1 | | | 291 | 4.89 | 59 |
| MG045 | G166N | A257V | | | 0.0 | | | 280 | 6.40 | 44 |
| SSM122 B9 | G188H | | | 8.6 | 3.3 | | | 246 | 6.67 | 37 |
| MG046 | G188T | | | | 2.1 | | | 200 | 4.09 | 49 |

| pMD3 ID | Mutation 1 | Mutation 2 | Mutation 3 | Na-citr. pH 6.5 75 | Na-citr. pH 6.5 80 | Na-citr. pH 6.5 + NaCl 75 | Na-citr. pH 6.5 + NaCl 80 | Betamyl | Phad | B/P |
|---|---|---|---|---|---|---|---|---|---|---|
| pMD3 avg | | | | 8.0 | 2.7 | | 0.8 | 355 | 5.54 | 63 |
| pMD4 | H13R | G424D | | | 2.6 | | | 305 | 4.58 | 67 |
| pMD5 | H13R | | | | 2.5 | | | 250 | 3.35 | 75 |
| pMD51 a | D62N | | | | | | | 10 | 0.32 | 32 |
| pMD51 b | D62N | | | | | | | 35 | 1.25 | 28 |
| S388 | F63L | N145D | | | 0.9 | | | 212 | 2.27 | 93 |
| pMD50 a | S64T | | | | 1.2 | | | 237 | 3.75 | 63 |
| pMD47 a | S64N | | | | 1.6 | | | 113 | 1.96 | 57 |
| pMD47 b | S64N | | | | | | | 301 | 4.45 | 68 |
| PMD38 b | G100A | | | | 2.2 | | | 434 | 7.50 | 58 |
| QCSS1 A5 | N119S | | | | 0.3 | | | 684 | 9.97 | 69 |
| QCSS1 A12 | N119G | | | | 0.0 | | | 707 | 6.02 | 117 |
| QCSS1 B5 | N119N | | | | | | | 874 | 10.33 | 85 |
| QCSS1 C11 | N119N | | | | | | | 982 | 13.57 | 72 |
| QCSS1 G5 | N119N | | | | | | | 830 | 10.93 | 76 |
| QCSS1 H12 | N119N | | | | | | | 792 | 10.01 | 79 |
| QCSS3 A1 | N119N | | | | 2.7 | | | 685 | 11.97 | 57 |
| QCSS3 A3 | N119N | | | | | | | 701 | 11.01 | 64 |
| QCSS3 A7 | N119N | | | | 2.7 | | | 641 | 10.72 | 60 |
| QCSS3 C3 | N119Y | | | | 2.3 | | | 714 | 10.20 | 70 |
| QCSS3 D8 | N119N | | | | | | | 697 | 10.52 | 66 |
| QCSS3 E10 | N119N | | | | | | | 728 | 12.05 | 60 |
| QCSS3 F8 | N119N | | | | 3.2 | | | 897 | 16.64 | 54 |
| QCSS3 G11 | N119N | | | | | | | 672 | 9.87 | 68 |
| pMD61 a | D121F | D269S | D422N | | 4.1 | | | 411 | 8.90 | 46 |
| pMD64 a | D121F | D269S | | | 4.7 | | | 405 | 7.68 | 53 |
| pMD42 a | D121T | | | | 2.4 | | | 313 | 3.11 | 101 |
| pMD42 b | D121T | | | | 2.6 | | | 294 | 3.03 | 97 |
| pMD55 a | D121F | | | | 5.2 | | | 284 | 5.01 | 57 |
| pMD55 b | D121F | | | | 6.8 | 5.1 | 1.6 | 246 | 4.76 | 52 |
| pMD44 a | D121W | | | | 5.2 | 3.7 | | 420 | 9.14 | 46 |
| pMD44 b | D121W | | | | 4.4 | | | 390 | 8.33 | 47 |
| pMD43 a | D121H | | | | 3.7 | | | 221 | 5.50 | 40 |
| pMD41 a | D121M | | | | 3.3 | | | 334 | 5.27 | 63 |
| PMD74 a | D121A | | | | | | | 260 | 2.99 | 87 |
| PMD74 a | D121A | | | | 3.3 | 2.8 | | 282 | 2.69 | 105 |
| PMD74 b | D121A | | | | | | | 319 | 3.40 | 94 |
| SSM167 H7 | D121V | | | | 1.8 | | | 199 | 4.74 | 42 |
| PMD74 a | D121A | | | | | | | 633 | 6.91 | 92 |
| PMD55 a | D121F | | | | | | | 575 | 9.96 | 58 |
| PMD55 a | D121F | | | | | | | 525 | 10.57 | 50 |
| PMD55 a | D121F | | | | 4.8 | 4.8 | 1.5 | 467 | 8.48 | 55 |
| S389 | K125E | Y297H | | | 0.5 | | | 183 | 1.63 | 112 |
| pMD70 a | A131T | | | | 1.7 | | | 304 | 4.55 | 67 |
| SSM175 E3 | G134R | | | | | | | 258 | 3.46 | 75 |
| SSM177 C3 | R134R | | | | | | | 534 | 6.26 | 85 |
| SSM177 C11 | R134R | | | | | | | 470 | 8.87 | 53 |
| pMD32 a | P141A | | | 2.0 | 0.9 | 1.2 | | 315 | 4.75 | 66 |
| pMD32 b | P141A | | | | | | | 274 | 4.27 | 64 |
| pMD48 a | F156Y | | | | | | | 25 | 1.35 | 19 |
| pMD48 b | F156Y | | | | | | | 10 | 1.05 | 10 |
| pMD31 a | L157I | | | | 1.1 | 0.8 | | 306 | 3.06 | 100 |
| pMD31 b | L157I | | | | | | | 276 | 2.83 | 98 |
| pMD68 a | G158S | | | | 2.8 | | | 400 | 10.24 | 39 |
| pMD68 b | G158S | | | | 3.0 | | | 361 | 8.37 | 43 |
| PMD69 | S161V | | | | 1.2 | | | 324 | 6.00 | 54 |
| pMD71 a | I170M | | | | 0.9 | | | 301 | 4.66 | 65 |
| SSM267 M1 | F178N | | | | 0.4 | | | 139 | 3.74 | 37 |
| SSM267 O17 | F178W | | | | 1.8 | | | 275 | 4.02 | 68 |
| SSM267 P22 | F178Q | | | | 0.8 | | | 309 | 4.18 | 74 |
| SSM181 B12 | T179P | | | | 0.7 | | | 303 | 3.79 | 80 |
| SSM181 G3 | T179S | | | | 2.2 | | | 436 | 5.91 | 74 |
| SSM182 E2 | T179N | | | | | | | 645 | 8.94 | 72 |
| SSM182 H11 | T179R | | | | 2.7 | | | 688 | 10.21 | 67 |
| SSM269 B3 | T179P | | | | 0.8 | | | 198 | 2.57 | 77 |
| SSM269 E15 | T179E | | | | 2.6 | | | 342 | 4.89 | 70 |
| SSM211 D12 | R196P | K222Y | | | | | | 60 | 0.15 | 414 |
| SSM211 B9 | R196Q | | | 7.9 | | | | 217 | 1.35 | 161 |

TABLE 7-continued

| | | | | | | | | | | | |
|---|---|---|---|---|---|---|---|---|---|---|---|
| SSM211B9 | R196Q | | | 7.9 | 2.0 | | | | 181 | 1.48 | 123 |
| SSM212A8 | R196T | | | 1.9 | | | | | 176 | 1.86 | 95 |
| SSM213 H7 | R196Q | | | | | | | | 69 | 0.36 | 193 |
| SSM211 B9 | R196Q | | | | | | | | 256 | 1.79 | 143 |
| SSM213 H7 | R196Q | | | | | | | | 74 | 0.39 | 190 |
| pMD49 a | A223V | | | 2.4 | 0.6 | | | | 301 | 2.62 | 115 |
| SSM171 G11 | A223E | | | 10.5 | 3.0 | | | | 574 | 5.52 | 104 |
| SSM171 G11 | A223E | | | | | | | | 684 | 5.59 | 122 |
| SSM171 G11 | A223E | | | | 2.7 | | | | 364 | 3.54 | 103 |
| SSM171 G11 | A223E | | | | 2.5 | | | | ND | ND | ND |
| SSM158 D10 | E226W | | | | 0.7 | | | | 196 | 1.35 | 145 |
| pMD52 c | D255V | | | | 2.5 | | | | 279 | 4.24 | 66 |
| pMD54 b | D269N | | | | 1.9 | | | | 247 | 4.26 | 58 |
| pMD60 a | D269S | | | | 2.2 | | | | 440 | 6.45 | 68 |
| SSM180 G6 | P334R | | | | | | | | 131 | 1.27 | 103 |
| SSM180 G6 | P334R | | | | | | | | 125 | 1.31 | 96 |
| SSM180 H10 | P334R | | | | 0.3 | | | | 86 | 1.07 | 80 |
| SSM179 D11 | P334K | | | | | | | | 113 | 1.50 | 75 |
| SSM280 K4 | P334T | | | | 0.4 | | | | 379 | 4.48 | 85 |
| SSM280 M11 | P334S | | | | 0.6 | | | | 382 | 4.82 | 79 |
| pMD46 a | S399P | | | | 2.4 | | | | 215 | 3.12 | 69 |
| pMD46 b | S399P | | | | | | | | 388 | 6.35 | 61 |
| pMD59 a | D422N | | | | 3.0 | | | | 523 | 6.58 | 79 |
| pMD34 a | G424S | | | | 2.3 | | | | 411 | 6.03 | 68 |

| pMD55 ID | Mutation | | | | Na-citr. pH 6.5 | | Na-citr. pH 6.5 + NaCl | | | Betamyl | Phad | B/P |
|---|---|---|---|---|---|---|---|---|---|---|---|---|
| | 1 | 2 | 3 | 4 | 80 | 85 | 75 | 80 | 85 | | | |
| pMD55 avg | | | | | 5.6 | 1.5 | 4.9 | 1.5 | 0.6 | 419 | 7.76 | 54 |
| S427 | P7S | N26D | | | 3.2 | | | | | 235 | 2.87 | 82 |
| PMD77 | A8N | | | | 5.8 | | | | | 174 | 2.45 | 71 |
| PMD78 | G9A | | | | 5.2 | | | | | 173 | 2.56 | 68 |
| SSM220 C6 | N26E | | | | 6.1 | 1.5 | | 1.5 | 0.5 | 295 | 3.54 | 83 |
| SSM220 G11 | N26E | | | | 5.0 | | | | | 483 | 6.96 | 69 |
| SSM222 D5 | N26E | | | | 4.7 | | | | | 521 | 7.03 | 74 |
| SSM219 B3 | N26E | | | | | | | | | 147 | 1.57 | 94 |
| SSM222 H4 | N26E | | | | 5.6 | | | | | 332 | 3.93 | 85 |
| S428 | P32S | G153D | | | 0.1 | | | | | 196 | 2.16 | 91 |
| SSM228 C7 | F63A | | | | | | | | | 327 | 5.10 | 64 |
| SSM228 E11 | F63D | | | | 4.6 | 0.9 | 4.2 | 1.5 | 0.6 | 389 | 6.43 | 61 |
| SSM229 D9 | F63E | | | | 3.8 | | | | | 436 | 6.60 | 66 |
| SSM229 E10 | F63D | | | | | | | | | 381 | 6.34 | 60 |
| SSM230 C9 | F63D | | | | | | | | | 431 | 7.24 | 60 |
| SSM230 D7 | F63V | | | | | | | | | 277 | 4.41 | 63 |
| S424 | T67V | Q239L | | | 2.0 | | | | | 276 | 4.11 | 67 |
| SSM217 A4 | D68C | | | | 5.6 | | | 1.7 | 0.6 | 182 | 2.96 | 61 |
| SSM217 B5 | D68E | | | | 5.2 | | | | | 335 | 7.49 | 45 |
| PMD81 | G100S | | | | 5.1 | | | | | 191 | 2.85 | 67 |
| SSM249 L12 | N119E | | | | 0.8 | | | | | 136 | 2.27 | 60 |
| SSM249 M13 | N119E | | | | 0.7 | | | | | 244 | 4.79 | 51 |
| SSM249 B20 | N119E | | | | 0.9 | | | | | 315 | 5.72 | 55 |
| SSM249 E9 | N119E | | | | 0.5 | | | | | 334 | 5.90 | 57 |
| SSM249 J13 | N119E | | | | 0.3 | | | | | 310 | 8.27 | 37 |
| SSM249 O14 | N119E | | | | 0.3 | | | | | 331 | 7.55 | 44 |
| PMD93 | F121P | | | | 0.7 | | | | | 620 | 6.70 | 93 |
| S426 | F121I | | | | 0.7 | | | | | 299 | 2.25 | 133 |
| SSM234 C9 | Y122W | | | | 3.0 | | | | | 396 | 4.04 | 98 |
| S423 | P123S | N138S | C140R | P143T | 0.0 | | | | | 236 | 2.11 | 112 |
| SSM225 B5 | K125G | | | | 1.6 | | | | | 104 | 1.30 | 80 |
| SSM226 D6 | K125G | | | | 1.5 | | | | | 468 | 6.60 | 71 |
| SSM225 F4 | K125A | | | | 2.2 | | | | | 474 | 6.80 | 70 |
| SSM233 B17 | K125W | | | | | | | | | 329 | 5.62 | 59 |
| SSM233 D13 | K125G | | | | | | | | | 449 | 6.69 | 67 |
| SSM233 H14 | K125W | | | | | | | | | 346 | 4.62 | 75 |
| SSM233 N10 | K125W | | | | 0.8 | | | | | 393 | 5.64 | 70 |
| SSM233 P15 | K125D | | | | | | | | | 452 | 7.99 | 57 |
| SSM304 B17 | R134C | | | | | 0.4 | | | | 307 | 2.54 | 121 |
| S425 | R137C | P334S | | | 0.0 | | | | | 205 | 2.63 | 78 |
| S430 | N138D | N145S | G300E | | 0.1 | | | | | 231 | 2.29 | 101 |
| SSM246 H24 | N138E | | | | 0.4 | | | | | 389 | 6.35 | 61 |
| PMD76 | D142G | | | | 0.2 | | | | | 187 | 12.76 | 15 |
| S431 | N148S | | | | 0.4 | | | | | 255 | 3.55 | 72 |
| SSM238 A14 | D154G | | | | 1.0 | | | | | 222 | 2.68 | 83 |
| SSM238 H15 | D154G | | | | 0.8 | | | | | 220 | 2.72 | 81 |
| SSM239 C17 | D154E | | | | 0.8 | | | | | 233 | 2.78 | 84 |
| SSM239 D18 | D154Y | | | | 0.7 | | | | | 109 | 0.81 | 135 |
| SSM288 K2 | L157V | L307D | | | | 1.4 | | | | 526 | 3.99 | 132 |
| SSM299 K9 | L157V | L307L | | | | 0.5 | | | | 311 | 3.62 | 86 |

TABLE 7-continued

| ID | Mutation 1 | | | | | | | | | |
|---|---|---|---|---|---|---|---|---|---|---|
| SSM279 B1 | L157M | | 6.2 | 1.3 | 6.2 | 1.9 | | 449 | 7.34 | 61 |
| SSM237 P2 | G158T | | 7.7 | 1.7 | 5.8 | 2.0 | 0.7 | 309 | 7.89 | 39 |
| SSM243 I3 | E160D | S161A | 3.8 | | | | | 346 | 2.93 | 118 |
| SSM243 A14 | E160D | S161A | 3.7 | | | | | 366 | 3.09 | 118 |
| SSM243 C23 | E160D | S161A | 3.5 | | | | | 465 | 4.39 | 106 |
| SSM235 C8 | S161A | | 5.5 | | | | | 446 | 4.56 | 98 |
| SSM235 E20 | S161A | | 5.5 | | | | | 467 | 4.12 | 113 |
| SSM235 G8 | S161T | | 5.2 | | | | | 375 | 6.44 | 58 |
| SSM235 P6 | S161A | | 5.4 | | | | | 307 | 2.74 | 112 |
| SSM235 P12 | S161A | | 6.2 | | 4.1 | 1.4 | 0.7 | 371 | 3.15 | 118 |
| SSM235 P12 | S161A | | | | | | | 261 | 2.29 | 114 |
| SSM276 A2 | I170E | | 1.1 | | | | | 299 | 4.99 | 60 |
| SSM276 A3 | I170L | | 2.9 | | | | | 397 | 7.47 | 53 |
| SSM276 A4 | I170K | | | | | | | 44 | 2.53 | 17 |
| SSM276 A5 | I170N | | 2.9 | | | | | 346 | 4.10 | 84 |
| S433 | S183G | E226G | 0.5 | | | | | 161 | 0.63 | 255 |
| PMD79 | G184Q | | 5.3 | | | | | 155 | 2.23 | 70 |
| SSM201 E9 | R196K | | 1.3 | | | | | 321 | 6.61 | 49 |
| SSM202 A11 | R196Y | | | | | | | 186 | 1.91 | 97 |
| PMD80 | S213N | | 6.3 | | | | | 155 | 2.10 | 74 |
| SSM244 I17 | L220A | | 0.5 | | | | | 321 | 5.35 | 60 |
| SSM244 P7 | L220T | | 0.6 | | | | | 204 | 4.41 | 46 |
| pMD85 | A223E | | 5.1 | 1.5 | | 1.5 | 0.5 | 452 | 4.29 | 105 |
| PMD85 | A223E | | | | | | | 572 | 5.06 | 113 |
| SSM302 D15 | E226C | L157L | L307L | | | | | 66 | 0.59 | 113 |
| SSM281 A18 | E226D | | | 0.7 | | | | 179 | 0.68 | 261 |
| SSM281 C6 | E226D | | 2.7 | 0.4 | | | | 26 | 0.12 | 217 |
| SSM281 H14 | E226D | | | 0.6 | | | | 187 | 0.70 | 267 |
| SSM240 N17 | A236E | | 0.5 | | | | | 234 | 3.37 | 70 |
| SSM240 K4 | A236E | | 0.5 | | | | | 215 | 3.13 | 69 |
| SSM236 H18 | W238Q | | | | | | | 289 | 4.27 | 68 |
| SSM236 B15 | W238G | | 0.7 | | | | | 266 | 3.37 | 79 |
| SSM236 E9 | W238G | | 0.6 | | | | | 211 | 2.57 | 82 |
| SSM236 G8 | W238K | | 0.7 | | | | | 239 | 3.48 | 69 |
| SSM268 B3 | W238R | | 3.3 | | | | | 207 | 3.59 | 58 |
| SSM268 D10 | W238P | | 1.7 | | | | | 189 | 3.92 | 48 |
| SSM268 E4 | W238E | | 2.2 | | | | | 203 | 3.44 | 59 |
| SSM268 L10 | W238Q | | 2.0 | | | | | 235 | 4.34 | 54 |
| SSM245 A12 | V253G | | 1.6 | | | | | 367 | 5.21 | 70 |
| SSM204E10 | E260R | | 1.5 | | | | | 221 | 3.99 | 55 |
| SSM205G1 | E260K | | | | | | | 110 | 1.44 | 76 |
| SSM206D2 | E260K | | | | | | | 94 | 1.25 | 75 |
| S429 | N264D | | 3.9 | | | | | 256 | 4.22 | 61 |
| PMD82 | T295C | W308C | 0.5 | | | | | 103 | 2.71 | 38 |
| PMD83 | T295C | | 0.4 | | | | | 93 | 4.79 | 19 |
| SSM247 C10 | Q305E | | 1.6 | | | | | 299 | 5.22 | 57 |
| SSM247 E3 | Q305T | | 2.2 | | | | | 211 | 5.61 | 38 |
| SSM207F2 | W308C | | 1.9 | | | | | | | ND |
| SSM207F2 | W308C | | 1.5 | | | | | 197 | 1.54 | 128 |
| SSM208B5 | W308C | | 1.6 | | | | | 229 | 1.86 | 123 |
| PMD84 | W308C | | 1.9 | | | | | 294 | 1.88 | 156 |
| SSM210 G5 | W308T | | 0.4 | | | | | 158 | 1.71 | 92 |

| pMD74 ID | Mutation 1 | Na-citr. pH 6.5 80 | Betamyl | Phad | B/P |
|---|---|---|---|---|---|
| pMD74 avg | | 3.3 | 287 | 3.03 | 95 |
| SSM253 F23 | F63E | | 62 | 0.64 | 98 |
| SSM253 J9 | F63D | | 53 | 0.55 | 97 |
| SSM253 O8 | F63E | 2.2 | 71 | 0.65 | 109 |
| SSM253 F23 | F63E | 1.9 | 394 | 3.43 | 115 |
| SSM253 J9 | F63D | 2.4 | 364 | 2.97 | 123 |
| SSM253 O8 | F63E | | 383 | 3.19 | 120 |
| SSM263 C11 | Y122A | 1.1 | 633 | 16.26 | 39 |
| SSM263 O21 | Y122Q | 0.7 | 651 | 9.81 | 66 |
| SSM264 H20 | Y122E | 0.2 | 743 | 7.44 | 100 |
| SSM264 K20 | Y122E | 0.3 | 728 | 6.93 | 105 |
| SSM265 C10 | K125D | 0.0 | 328 | 3.65 | 90 |
| SSM265 E3 | K125Q | 0.1 | 452 | 4.23 | 107 |
| SSM265 I13 | K125W | 0.0 | 354 | 3.35 | 106 |
| SSM265 K17 | K125P | 0.1 | 339 | 3.12 | 109 |
| SSM265 M16 | K125P | 0.0 | 471 | 5.26 | 90 |
| SSM256 F18 | R196S | 0.4 | 162 | 1.04 | 156 |
| SSM256 C9 | R196G | 0.4 | 213 | 1.65 | 129 |
| SSM256 D3 | R196A | 0.4 | 103 | 0.83 | 124 |
| SSM256 M11 | R196G | 0.5 | 187 | 1.25 | 149 |
| SSM256 O22 | R196A | | 87 | 0.59 | 146 |
| SSM256 P11 | R196G | 0.5 | 195 | 0.92 | 212 |
| SSM256 O16 | R196V | 0.4 | 268 | 1.61 | 167 |

TABLE 7-continued

| | | | | | | | |
|---|---|---|---|---|---|---|---|
| SSM252 F14 | K222M | 0.0 | | 37 | 0.16 | 231 | |
| SSM252 F14 | K222M | 0.0 | | 266 | 1.93 | 138 | |
| PMD86 | A223E | 3.6 | | 112 | 0.70 | 160 | |
| PMD86 | A223E | | | 297 | 1.92 | 154 | |
| SSM255 A8 | A223D | 2.9 | | 90 | 0.65 | 139 | |
| SSM255 D21 | A223P | 2.5 | | 59 | 0.16 | 369 | |
| SSM255 N20 | A223D | | | 61 | 0.30 | 204 | |
| SSM255P11 | A223K | | | 70 | 0.39 | 180 | |
| SSM255 P21 | A223V | | | 64 | 0.31 | 207 | |
| SSM255 A8 | A223D | | | 441 | 3.11 | 142 | |
| SSM255D21 | A223P | 1.9 | | 353 | 1.59 | 222 | |
| SSM255 N20 | A223D | 2.1 | | 339 | 2.50 | 135 | |
| SSM255 P11 | A223K | 2.5 | | 439 | 2.93 | 150 | |
| SSM255 P21 | A223V | 0.8 | | 299 | 3.08 | 97 | |
| SSM257 E17 | Y227G | 0.0 | | 183 | 0.40 | 462 | |
| SSM257 K22 | Y227T | 0.0 | | 316 | 1.08 | 294 | |
| SSM257 O18 | Y227D | 0.0 | | 139 | 0.53 | 261 | |
| SSM257 P4 | Y227K | 0.0 | | 113 | 0.10 | 1130 | |

| pMD85 | Mutation | | | | Na-citr. pH 6.5 | Na-acet. + NaCl | | | |
|---|---|---|---|---|---|---|---|---|---|
| ID | 1 | 2 | 3 | 4 | 80 | 80 | Betamyl | Phad | B/P |
| pMD85 avg | | | | | 5.1 | 0.5 | 512 | 4.68 | 109 |
| PMD94 | N26E | D68C | S161A | | 6.1 | 0.7 | 81 | 0.26 | 312 |
| PMD110 | N26E | D68C | S161A | R196Q | 4.5 | | 62 | 0.21 | 295 |
| PMD98 | N26E | S161A | R196Q | | 3.2 | | 168 | 0.43 | 391 |
| PMD98 | N26E | S161A | R196Q | | 3.9 | | 219 | 0.58 | 377 |
| PMD98 | N26E | S161A | R196Q | | 3.3 | | 244 | 0.84 | 291 |
| pMD98 | N26E | S161A | R196Q | | 3.8 | | 220 | 0.68 | 324 |
| PMD100 | N26E | S161A | | | 5.8 | | 253 | 0.86 | 294 |
| PMD100 | N26E | S161A | | | 5.5 | | 376 | 1.30 | 290 |
| PMD99 | N26E | R196Q | | | 3.5 | | 94 | 0.47 | 200 |
| PMD97 | N26E | | | | 4.8 | 0.3 | 206 | 1.37 | 150 |
| PMD116 | F63D | D142D | W308C | | 0.7 | | 212 | 1.56 | 136 |
| PMD114 | F63D | S213N | E223P | W308C | 0.8 | | 216 | 1.75 | 124 |
| PMD121 | F63D | S213N | E223P | | 2.8 | | 425 | 2.86 | 149 |
| PMD111 | F63D | S213N | W308C | | 0.8 | | 269 | 1.98 | 136 |
| PMD115 | F63D | S213N | W308C | | 1.0 | | 252 | 1.82 | 139 |
| PMD120 | F63D | S213N | | | 4.5 | | 505 | 5.57 | 91 |
| PMD113 | F63D | W308C | | | 0.9 | | 242 | 1.80 | 135 |
| PMD118 | F63D | W308C | | | 1.1 | | 296 | 1.90 | 155 |
| PMD119 | F63D | | | | 4.8 | | 501 | 5.63 | 89 |
| PMD101 | D68C | S161A | R196Q | | 5.6 | 0.5 | 30 | 0.09 | 333 |
| PMD103 | D68C | S161A | | | 5.4 | 1.1 | 58 | 0.27 | 215 |
| PMD95 | S161A | R196Q | | | 3.8 | | 148 | 0.60 | 247 |
| PMD96 | S161A | | | | 6.6 | | 99 | 0.43 | 230 |
| PMD96 | S161A | | | | 6.3 | | 335 | 1.68 | 199 |
| PMD96 | S161A | | | | 5.5 | | 366 | 2.75 | 133 |
| PMD96 | S161A | | | | 5.5 | | 364 | 2.37 | 154 |
| PMD87 | R196Q | | | | 4.3 | | 61 | 0.51 | 119 |
| PMD88 | R196Q | | | | 3.8 | | 61 | 0.52 | 118 |
| PMD102 | R196Q | | | | 4.3 | 0.6 | 127 | 0.83 | 153 |
| PMD117 | S213N | | | | 5.2 | 0.6 | 510 | 3.37 | 151 |
| PMD112 | W308C | | | | 0.7 | | 253 | 2.39 | 106 |

| pMD86 | Mutation | | | Na-citr. pH 6.5 | | | |
|---|---|---|---|---|---|---|---|
| ID | 1 | 2 | 3 | 80 | Betamyl | Phad | B/P |
| pMD86 avg | | | | 3.6 | 204 | 1.31 | 157 |
| PMD107 | N26E | D68C | S161A | 2.0 | 94 | 0.43 | 219 |
| PMD105 | N26E | S161A | R196Q | 1.7 | 158 | 0.41 | 385 |
| PMD104 | N26E | S161A | | 1.7 | 280 | 0.81 | 346 |
| PMD106 | S161A | R196Q | | 1.8 | 124 | 0.43 | 288 |
| PMD109 | S161A | | | 2.2 | 310 | 1.69 | 183 |
| PMD89 | R196Q | | | 2.3 | 72 | 0.48 | 149 |
| PMD90 | R196Q | | | 2.5 | 78 | 0.41 | 189 |
| PMD108 | R196Q | | | 1.9 | 192 | 0.86 | 223 |
| PMD91 | S208T | | | 2.8 | 758 | 6.86 | 110 |
| PMD92 | S229N | | | 1.9 | 662 | 6.36 | 104 |

| pMD96 | Mutation | | | | | Na-citr. pH 6.5 | | Na-citr. pH 6.5 + NaCl | | | Na-acet. + NaCl | | | | |
|---|---|---|---|---|---|---|---|---|---|---|---|---|---|---|---|
| ID | 1 | 2 | 3 | 4 | 5/6/7 | 80 | 85 | 75 | 80 | 85 | 80 | 85 | Beta | Phad | B/P |

TABLE 7-continued

| ID | Mut1 | Mut2 | Mut3 | Mut4 | Mut5 | V1 | V2 | V3 | V4 | V5 | V6 | V7 | V8 | V9 |
|---|---|---|---|---|---|---|---|---|---|---|---|---|---|---|
| pMD96 avg | | | | | | 6.0 | 1.4 | 4.6 | 1.7 | 0.6 | 0.7 | 302 | 1.93 | 172 |
| SSM354 C8 | I38M | | | | | 5.2 | | 6.6 | 1.6 | | | 548 | 2.67 | 206 |
| SSM347 B12 | I46F | | | | | | | | 1.8 | | | 413 | 2.33 | 177 |
| SSM328 B5 | K71M | | | | | | | | | | 0.6 | 361 | 1.49 | 242 |
| SSM406 C12 | G104R | | | | | 5.0 | | | 1.9 | 0.7 | | 278 | 1.82 | 153 |
| SSM406 A6 | G104N | | | | | | | | 1.7 | 0.5 | | 456 | 2.29 | 199 |
| PMD135 | N116D | G153A | L157M | A309P | | | | 1.0 | | | | 184 | 0.58 | 317 |
| PMD134 | N116D | G153A | A309P | | | | | 0.0 | | | | 7 | 0.10 | 70 |
| PMD182 | N116D | G153A | A309P | | | | | | | 0.0 | | 202 | 0.49 | 413 |
| PMD136 | N116D | G153A | | | | | | 0.0 | | | | 3 | 0.10 | 30 |
| PMD138 | N116D | L157M | A309P | | | | | | | | | 296 | 1.27 | 232 |
| PMD143 | N116D | L157M | | | | | | 1.0 | | | | 330 | 1.87 | 177 |
| pMD143 | N116D | L157M | | | | | | | | | | 268 | 1.93 | 139 |
| PMD137 | N116D | A309P | | | | | | | | 0.0 | | 289 | 1.00 | 291 |
| PMD139 | N116D | | | | | | | | | 0.0 | 0.0 | 116 | 0.42 | 276 |
| PMD183 | N116D | | | | | | | | | 0.0 | 0.0 | 362 | 1.13 | 319 |
| SSM329 H2 | D124S | | | | | 0.6 | | 4.1 | | | | 379 | 2.96 | 128 |
| pMD126 | E126N | G158T | Y198W | | | | | | | | | 108 | 0.56 | 191 |
| pMD127 | E126N | G158T | S229P | | | | | 4.9 | | | | 471 | 4.30 | 110 |
| PMD132 | E126N | G158T | | | | | | | 1.5 | | | 424 | 3.21 | 132 |
| pMD125 | E126N | Y198W | S229P | | | | 0.4 | 11.8 | 2.2 | | | 114 | 0.57 | 200 |
| PMD122 | E126N | S229P | | | | | | | | | | 645 | 4.53 | 142 |
| SSM359 A5 | E126D | | | | | | | | | | | 548 | 3.24 | 169 |
| PMD128 | E126N | | | | | | | | | | | 603 | 4.33 | 139 |
| SSM411 C10 | N128E | | | | | | | | 1.7 | | | 166 | 1.61 | 103 |
| SSM379 D4 | G144E | | | | | | | 0.5 | | | | 316 | 1.03 | 307 |
| PMD146 | Y146G | G158T | Y198W | S229P | R316S | | | 19.2 | | 3.3 | 1.4 | 84 | 0.22 | 362 |
| PMD147 | Y146G | G158T | Y198W | S229P | A309P | | 9.9 | | 12.5 | 7.8 | 5.5 | 77 | 0.28 | 272 |
| PMD149 | Y146G | G158T | Y198W | S229P | A309P/R316S | | | | 7.6 | 5.9 | 3.7 | 87 | 0.26 | 335 |
| PMD150 | Y146G | G158T | Y198W | S229P | R353T | | | | | 2.3 | 2.4 | 65 | 0.23 | 282 |
| PMD151 | Y146G | G158T | Y198W | S229P | | | 3.4 | | | | 2.8 | 98 | 0.44 | 223 |
| PMD158 | Y146G | G158T | Y198W | S229P | A309P/R316S/R353T | | 13.4 | | 39.0 | 5.2 | 6.1 | 56 | 0.27 | 207 |
| pMD147 bf | Y146G | G158T | Y198W | S229P | A309P | | | | | | | 53 | 0.19 | 276 |
| PMD153 | Y146G | G158T | S229P | A309P | | | | | 3.9 | 2.9 | 2.0 | 233 | 1.42 | 199 |
| PMD154 | Y146G | G158T | S229P | | | | | | 1.8 | 2.3 | | 239 | 1.13 | 212 |
| PMD156 | Y146G | G158T | S229P | R316S | | | | | | 1.8 | | 299 | 1.40 | 214 |
| PMD157 | Y146G | G158T | S229P | A309P | R316S | | | | 3.6 | 1.8 | | 278 | 1.01 | 275 |
| PMD153 | Y146G | G158T | S229P | A309P | | | 8.7 | | | 3.2 | 2.5 | 183 | 0.86 | 213 |
| PMD157 | Y146G | G158T | S229P | A309P | R316S | | 11.8 | | | 3.3 | 1.1 | 319 | 1.42 | 225 |
| SSM381 G12 | Y146G | | | | | 19.2 | 2.6 | | 5.3 | 0.8 | | 409 | 1.71 | 239 |
| SSM381 A3 | Y146G | | | | | 16.0 | 2.5 | | 4.0 | 0.9 | | 424 | 2.43 | 174 |
| SSM381 B9 | Y146E | | | | | | | 2.0 | | | | 308 | 0.91 | 338 |
| SSM381 D7 | Y146D | | | | | | | 0.4 | | | | 267 | 0.61 | 438 |
| SSM413 A4 | N148K | | | | | | | | | 0.0 | | 406 | 1.78 | 228 |
| SSM330 A1 | D149V | | | | | | | | | | | 511 | 4.22 | 121 |
| SSM330 C5 | D149L | | | | | | | | | | | 405 | 3.23 | 125 |
| SSM364 B3 | D151W | | | | | | | 0.0 | | | | 151 | 0.25 | 613 |
| SSM364 D3 | D151A | | | | | | | 0.0 | | 0.0 | | 163 | 0.18 | 904 |
| SSM364 D7 | D151V | | | | | | | 0.0 | | | | 168 | 0.18 | 944 |
| PMD141 | G153A | A309P | | | | | | | 0.0 | | | 215 | 0.76 | 284 |
| PMD161 | L157M | A309P | | | | | | | | | | 53 | 0.22 | 241 |
| PMD140 | L157M | | | | | 7.3 | | | 1.9 | | | 331 | 1.56 | 212 |
| pMD124 | G158T | Y198W | S229P | | | 20.0 | 2.2 | 40.6 | 9.3 | 1.8 | 2.1 | 127 | 0.55 | 231 |
| PMD144 | G158T | Y198W | S229P | A309P | | 46.3 | 11.6 | | 17.8 | 4.3 | | 76 | 0.29 | 261 |
| PMD148 | G158T | Y198W | S229P | A309P | | | 7.4 | | | 4.0 | 2.2 | 70 | 0.26 | 266 |
| PMD152 | G158T | Y198W | S229P | A309P | R316S | | | | | 4.7 | 3.7 | 67 | 0.21 | 313 |
| PMD155 | G158T | S229P | A309P | | | | 6.0 | | | 1.5 | 1.5 | 235 | 1.09 | 216 |
| PMD159 | G158T | S229P | A309P | R316S | R353T | | | | 3.4 | 1.6 | | 81 | 0.29 | 280 |
| PMD131 | G158T | S229P | | | | 7.2 | | | 2.9 | | | 380 | 2.92 | 130 |
| PMD130 | G158T | | | | | 8.0 | 1.7 | | 2.3 | | | 380 | 3.10 | 122 |
| SSM415 G2 | N164R | | | | | | | | | 0.0 | | 362 | 1.68 | 216 |
| SSM410 E1 | Q169K | | | | | 7.5 | | | 1.9 | | | 260 | 1.74 | 149 |
| SSM410 F8 | Q169V | | | | | 5.6 | | | 1.9 | | | 273 | 1.64 | 166 |
| SSM410 E3 | Q169R | | | | | 6.5 | | | 2.2 | | | 344 | 2.52 | 136 |
| SSM410 E2 | Q169G | | | | | | | | | 1.5 | | 307 | 1.37 | 225 |
| SSM410 G5 | Q169E | | | | | | | | | 0.5 | | 377 | 1.41 | 268 |
| SSM410 H9 | Q169N | | | | | | | | | 0.5 | | 356 | 1.46 | 244 |
| SSM348 B10 | R182S | | | | | | | | 1.9 | | | 576 | 3.18 | 181 |
| SSM348 A4 | R182H | | | | | 6.2 | 5.4 | 1.8 | | | | 502 | 2.98 | 169 |
| SSM348 D8 | R182M | | | | | 5.2 | 5.0 | 1.9 | | | | 687 | 3.92 | 175 |
| SSM348 A9 | R182D | | | | | 5.0 | 4.5 | 2.1 | | | | 593 | 3.65 | 163 |

TABLE 7-continued

| ID | Mutation | | | | | | | | | | Beta | Phad | B/P |
|---|---|---|---|---|---|---|---|---|---|---|---|---|---|
| SSM348 D11 | R182S | | | | 5.9 | | 5.0 | 1.7 | | | 584 | 3.40 | 172 |
| SSM348 H4 | R182G | | | | 6.7 | | 5.3 | 1.8 | | | 519 | 2.68 | 194 |
| SSM419 A5 | F192Y | | | | | | | 1.9 | 0.6 | | 158 | 1.50 | 106 |
| SSM419 A11 | F192F | | | | | | | 2.5 | | | 316 | 1.56 | 203 |
| SSM419 B4 | F192M | | | | | | | | | 0.3 | 298 | 1.45 | 205 |
| SSM420 B11 | V195D | | | | | | | | | 0.7 | 181 | 1.22 | 148 |
| pMD129 | Y198W | S229P | | | 9.8 | 2.4 | 16.9 | 6.6 | 1.1 | 0.6 | 183 | 0.77 | 297 |
| SSM383 E8 | A199P | | | | | | | | | | 231 | 0.78 | 296 |
| SSM422 G5 | P200G | | | | 8.0 | | | 2.3 | | | 164 | 0.88 | 187 |
| SSM422 B4 | P200A | | | | 6.1 | | | 2.0 | | | 255 | 1.33 | 192 |
| SSM361 A2 | R202K | | | | | | | 1.6 | | | 228 | 0.87 | 264 |
| SSM325 F3 | S229P | | | | 7.9 | 1.8 | 8.8 | 2.0 | | | 355 | 2.51 | 141 |
| SSM325 F3 | S229P | | | | | | | | | | 289 | 1.76 | 164 |
| SSM341 A9 | G303E | | | | 4.4 | | 4.9 | 1.4 | | | 404 | 1.53 | 264 |
| SSM341 G11 | G303D | | | | 3.7 | | 4.3 | | | | 388 | 1.69 | 230 |
| SSM332 A11 | A309T | | | | | | | | | | 334 | 1.95 | 171 |
| SSM332 A6 | A309E | | | | | | | | | | 359 | 2.18 | 165 |
| SSM332 Q2 | A309M | | | | | | | | | | 465 | 2.63 | 177 |
| SSM332 Q1 | A309V | | | | | | | | | | 465 | 2.29 | 203 |
| SSM332 Q3 | A309I | | | | | | | | | | 404 | 1.87 | 216 |
| SSM332 Q4 | A309P | | | | 7.5 | 2.5 | 5.3 | 2.1 | | | 546 | 2.70 | 202 |
| PMD181 | A309P | | | | | | | 2.1 | | | 364 | 1.46 | 250 |
| SSM318 B2 | D312E | | | | | | | | | | 429 | 3.13 | 137 |
| SSM365 C2 | R316Q | | | | | | | | | | 372 | 1.66 | 224 |
| SSM365 B4 | R316S | | | | 7.5 | 2.5 | 4.8 | 1.8 | | | 330 | 1.52 | 216 |
| SSM365 F4 | R316P | | | | 7.1 | 2.0 | 4.7 | 1.8 | | | 362 | 1.79 | 202 |
| SSM365 C10 | R316K | | | | 11.3 | 5.5 | 5.5 | | | | 342 | 1.22 | 281 |
| SSM407 A5 | T324L | | | | 5.1 | | | 1.7 | 0.4 | | 399 | 1.95 | 205 |
| SSM407 B11 | T324M | | | | 5.4 | | | 1.8 | 0.5 | | 304 | 1.40 | 217 |
| SSM407 A5 | T324L | | | | | | | | | 0.7 | 349 | 1.91 | 183 |
| SSM407 B10 | T324A | | | | | | | | | 0.6 | 345 | 1.83 | 189 |
| SSM333 A9 | H335M | | | | | | | | | | 54 | 0.50 | 108 |
| SSM360 C7 | R353T | | | | 5.6 | | 4.9 | 1.8 | | | 327 | 1.32 | 248 |
| SSM418 B2 | R358A | | | | | | | 1.5 | | | 145 | 1.38 | 105 |
| SSM418 B12 | R358T | | | | | | | 1.8 | | | 153 | 1.46 | 105 |
| SSM418 C6 | R358L | | | | | | | 1.8 | | | 155 | 1.48 | 105 |
| SSM418 C7 | R358V | | | | | | | 2.5 | 0.5 | | 155 | 1.66 | 94 |
| SSM418 E2 | R358Q | | | | | | | 1.7 | 0.5 | | 156 | 1.57 | 99 |
| SSM418 D12 | R358E | | | | | | | 1.8 | 0.5 | | 133 | 1.25 | 106 |
| SSM418 A2 | R358N | | | | | | | | | 0.6 | 358 | 1.53 | 234 |
| SSM418 B5 | R358G | | | | | | | | | 0.8 | 304 | 2.11 | 144 |
| SSM356 A7 | S367R | | | | | | 5.7 | | | | 43 | 0.23 | 190 |
| SSM356 B5 | S367Q | | | | 5.0 | | 7.3 | 2.0 | | | 449 | 2.49 | 180 |
| SSM320 G3 | D390E | | | | | | 1.2 | | | | 542 | 3.17 | 171 |
| SSM320 D1 | D390D | | | | | | | | | | 362 | 2.30 | 158 |
| SSM323 A3 | D422Q | | | | | | 1.2 | | | | 561 | 3.13 | 179 |
| SSM323 A4 | D422P | | | | | | 1.2 | | | | 480 | 2.81 | 171 |

| pMD153 ID | Mutation | | | | Na-citr. pH 6.5 | | Na-citr. pH 6.5 + NaCl | Na-acet. + NaCl | | Beta | Phad | B/P |
|---|---|---|---|---|---|---|---|---|---|---|---|---|
| | 1 | 2 | 3 | 4 | 85 | 90 | 85 | 80 | 85 | | | |
| pMD153 avg | | | | | 12.3 | 1.7 | 3.9 | 3.1 | 2.2 | 208 | 1.14 | 206 |
| pMD233 | G70D | N145D | S225E | H272Q | | | | 5.1 | 1.9 | 541 | 1.01 | 536 |
| pMD234 | G70D | N145D | S225E | H272Q | | | | 4.6 | 1.7 | 512 | 1.00 | 512 |
| pMD212 | G70D | N145D | W339E | | | | 4.7 | | 2.8 | 382 | 0.44 | 876 |
| pMD214 | G70D | N145D | W339E | | | | | 3.7 | 2.7 | 395 | 0.50 | 796 |
| pMD212 bf | G70D | N145D | W339E | | | | | 3.1 | 1.6 | 426 | 0.58 | 734 |
| pMD214 bf | G70D | N145D | W339E | | | | | 2.6 | 0.8 | 381 | 0.53 | 723 |
| pMD212 bf | G70D | N145D | W339E | | | | | 2.7 | 1.0 | 358 | 0.43 | 834 |
| pMD212 bf | G70D | N145D | W339E | | 12.2 | | | 2.6 | | 308 | 0.42 | 733 |
| pMD219 | G70D | N145D | | | | | | 2.3 | 2.0 | 238 | 0.55 | 433 |
| pMD240 | | N145D | | | | | | 5.4 | | 230 | 0.60 | 383 |
| pMD220 | G70D | S225E | H272Q | | | | | 3.4 | 1.3 | 205 | 0.65 | 315 |
| SAS1401 L10 | G70D | | | | | | | | 2.7 | 254 | 1.01 | 268 |
| SAS1401 L10 bf | G70D | | | | | | | | | 271 | 1.02 | 266 |

TABLE 7-continued

| ID | Mutation 1 | Mutation 2 | Mutation 3 | Mutation 4 | 80 | 85 | Beta | Phad | B/P |
|---|---|---|---|---|---|---|---|---|---|
| pMD216 | G70D | | | | | 3.3 | 2.8 | 220 | 1.09 | 202 |
| PMD173 | G104R | Q169R | P200A | T324L | 1.3 | 5.2 | 4.9 | 261 | 1.72 | 151 |
| PMD174 | G104R | Q169R | P200A | | | 4.6 | 2.6 | 299 | 2.28 | 131 |
| PMD177 | G104R | Q169R | T324L | | | 3.9 | 2.0 | 337 | 2.46 | 137 |
| PMD179 | G104R | Q169R | | | | 4.2 | | 320 | 2.40 | 133 |
| pMD188 | G104R | P200A | | | | | 3.5 | 227 | 1.22 | 186 |
| PMD175 | G104R | T324L | | | | 2.9 | 1.4 | 331 | 1.93 | 171 |
| PMD178 | G104R | | | | | 3.0 | | 337 | 1.38 | 244 |
| pMD232 | C140A | C150A | | | | 2.1 | 0.0 | 168 | 1.22 | 138 |
| SSM448 O17 | D142D | | | | | | 4.0 | 378 | 2.05 | 184 |
| SSM448 M7 | D142D | | | | | 3.2 | | 240 | 1.86 | 129 |
| pMD222 | N145D | H272Q | | | | 5.2 | 2.8 | 225 | 0.63 | 357 |
| pMD222 bf | N145D | H272Q | | | | 5.1 | | 237 | 0.65 | 365 |
| pMD215 | N145D | W339E | | | | 2.6 | 2.6 | 288 | 0.53 | 542 |
| SAS1387 D16 | N145D | | | | | | 1.9 | 117 | 0.32 | 366 |
| SAS1387 D16 bf | N145D | | | | | | | 303 | 0.81 | 374 |
| pMD213 | N145D | | | | | 5.1 | 3.7 | 280 | 0.94 | 297 |
| SAS1387 D16 bf | N145D | | | | 22.3 | 8.7 | 1.9 | 293 | 0.95 | 309 |
| PMD164 | L157M | T158G | G303E | | | 1.4 | | 452 | 1.63 | 277 |
| SAS1401C6 | L157M | T158G | | | | | 1.2 | 379 | 1.92 | 197 |
| SAS1401 L17 | L157M | T158G | | | | | 1.3 | 315 | 1.16 | 255 |
| SAS1398 G17 | L157M | T158G | | | | | 2.2 | 294 | 1.14 | 259 |
| SAS1392 I15 | L157M | T158G | | | | | 2.0 | 251 | 1.00 | 251 |
| SAS1396 H24 | L157M | T158G | | | | | 1.9 | 216 | 0.82 | 264 |
| PMD162 | T158G | G303E | R316K | | | 1.6 | | 541 | 1.54 | 351 |
| PMD165 | T158G | G303E | R316K | | | 1.5 | | 394 | 1.02 | 385 |
| PMD169 | T158A | G303E | R316K | | | | | 348 | 1.08 | 322 |
| PMD167 | T158A | G303E | | | | 1.2 | | 413 | 1.48 | 279 |
| PMD172 | T158G | G303E | | | | 1.9 | 0.6 | 461 | 1.10 | 421 |
| pMD172 | T158G | G303E | | | | | | 288 | ND | ND |
| pMD172 | T158G | G303E | | | | | 1.1 | 232 | 0.53 | 438 |
| pMD172 | T158G | G303E | | | | | | 333 | 0.83 | 401 |
| pMD172 bf | T158G | G303E | | | 4.9 | 1.4 | 0.6 | 513 | 0.98 | 523 |
| PMD170 | T158G | R316K | | | | 2.0 | | 545 | 1.75 | 312 |
| PMD171 | T158A | R316K | | | | 2.3 | 0.6 | 531 | 1.90 | 279 |
| PMD168 | T158G | | | | | 2.2 | 2.2 | 0.9 | 512 | 1.92 | 267 |
| pMD184 | T158A | | | | | | 1.4 | 286 | 1.43 | 200 |
| SAS1391 G13 | P168L | | | | | | 1.7 | 212 | 0.83 | 256 |
| PMD176 | Q169R | P200A | T324L | | | 4.9 | 2.6 | 291 | 2.29 | 127 |
| pMD187 | Q169R | | | | 1.1 | | 3.3 | 234 | 1.45 | 162 |
| Hit78 D1 | S225G | | | | | | 1.1 | 330 | 1.73 | 191 |
| Hit78 B1 | S225E | | | | | 2.2 | | 271 | 1.05 | 209 |
| Hit78 G1 | S225V | | | | | | 0.9 | 337 | 1.48 | 228 |
| pMD218 | S225E | | | | | 2.3 | 1.1 | 174 | 0.85 | 205 |
| Hit78 F3 | S237G | | | | | | 1.9 | 174 | 0.94 | 204 |
| Hit78 H7 | W282S | | | | | 2.8 | 2.2 | 220 | 0.79 | 234 |
| pMD221 | W282S | | | | | 4.2 | 0.0 | 192 | 0.94 | 204 |
| PMD163 | G303E | R316K | | | | 2.2 | | 463 | 1.53 | 303 |
| pMD185 | G303E | | | | | | 1.0 | 262 | 0.67 | 391 |
| SAS1402 G14 | W308K | | | | | 2.3 | 1.8 | 284 | 1.21 | 235 |
| SAS1402 G14 bf | W308K | | | | | 0.0 | | 161 | 0.80 | 201 |
| PMD166 | R316K | | | | | 3.0 | 3.6 | 520 | 2.27 | 229 |
| PMD180 | T324L | | | | | | 1.9 | 234 | 0.88 | 265 |
| SAS1379 O9 | W339E | | | | | | 1.3 | 235 | 0.73 | 322 |
| SAS1379 O13 | W339A | | | | | | 1.2 | 199 | 0.65 | 301 |
| pMD217 | W339E | | | | | 2.3 | 1.5 | 235 | 0.63 | 373 |
| SSM433 C3 | Y341E | | | | | 0.0 | | 161 | 0.65 | 247 |
| SSM433 H1 | Y341C | | | | | 2.3 | | 196 | 0.64 | 306 |

| pMD153d1 ID | Mutation 1 | Mutation 2 | Mutation 3 | Na-acet. + NaCl 80 | 85 | Beta | Phad | B/P |
|---|---|---|---|---|---|---|---|---|
| pMD153 avg | | | | 3.1 | 2.2 | 208 | 1.14 | 206 |
| pMD205 | G70D | N145D | W339E | | 3.1 | 322 | 1.15 | 280 |
| pMD206 | G70D | N145D | W339E | | 2.3 | 313 | 0.98 | 320 |
| pMD205 bf | G70D | N145D | W339E | 3.1 | | 632 | 3.94 | 160 |
| pMD206 bf | G70D | N145D | W339E | 2.4 | | 571 | 3.43 | 167 |
| pMD239 | G70D | N145D | | 5.5 | | 159 | 0.94 | 169 |
| pMD211 | G70D | W339E | | | 1.8 | 389 | 1.64 | 237 |
| pMD208 | G70D | | | | 3.1 | 279 | 1.98 | 141 |
| pMD209 | N145D | W339E | | 2.1 | 1.9 | 234 | 0.89 | 263 |
| pMD207 | N145D | | | 3.9 | 4.0 | 284 | 1.46 | 195 |
| pMD210 | W339E | | | | 1.3 | 324 | 1.68 | 193 |

TABLE 7-continued

| pMD172 | Mutation | | | | | Na-citr. pH 6.5 | Na-acet. + NaCl | | | | |
|---|---|---|---|---|---|---|---|---|---|---|---|
| ID | 1 | 2 | 3 | 4 | 5 | 85 | 80 | 85 | Beta | Phad | B/P |
| pMD172 avg | | | | | | 4.9 | 1.4 | 0.8 | | | 446 |
| pMD192 | N26E | L157M | Q169R | P200G | G158T | | 0.7 | 0.4 | 373 | 2.06 | 181 |
| pMD203 | N26E | L157M | Q169R | P200G | | | | 1.0 | 79 | 0.32 | 248 |
| pMD202 | N26E | L157M | P200G | | | | | 0.8 | 94 | 0.25 | 378 |
| pMD198 | N26E | L157M | P200G | | | | | | 337 | 1.66 | 203 |
| pMD189 | N26E | Q169R | P200G | | | | 0.7 | 0.5 | 446 | 1.38 | 324 |
| pMD193 | N26E | Q169R | P200G | | | | 0.7 | 0.3 | 402 | 1.41 | 285 |
| pMD204 | N26E | Q169R | P200G | | | | 0.8 | 0.3 | 337 | 1.38 | 244 |
| pMD190 | N26E | P200G | | | | | 0.8 | 0.5 | 485 | 0.95 | 511 |
| pMD191 | N26E | | | | | | | 0.3 | 404 | 0.86 | 470 |
| pMD200 | N26E | | | | | | | 0.7 | 141 | 0.48 | 294 |
| pMD197 | D142E | Q169R | | | | | | | 117 | 0.41 | 287 |
| pMD225 | N145D | S237D | R233H | | | | 1.0 | 0.4 | 267 | 0.43 | 628 |
| pMD228 | N145D | S237G | H272Q | | | | 1.6 | 1.1 | 257 | 0.37 | 695 |
| pMD231 | N145D | S237D | H272Q | | | | 1.5 | 1.0 | 255 | 0.34 | 750 |
| pMD224 | N145D | S237G | | | | | 1.9 | 1.2 | 159 | 0.26 | 612 |
| pMD230 | N145D | H272Q | | | | | | 2.1 | 208 | 0.29 | 715 |
| pMD230 bf | N145D | H272Q | | | | | 2.2 | 2.3 | 351 | 0.41 | 849 |
| pMD230 bf | N145D | H272Q | | | | | 3.2 | | 230 | 0.24 | 958 |
| pMD194 | Q169R | P200G | | | | | | 0.7 | 366 | 1.19 | 307 |
| pMD201 | P200G | | | | | | | 1.0 | 147 | 0.41 | 358 |
| pMD227 | S237G | L110F | | | | | 1.3 | 1.0 | 296 | 0.67 | 445 |
| pMD223 | S237G | H272Q | | | | | 1.5 | 1.3 | 259 | 0.59 | 439 |
| pMD226 | S237D | | | | | | 1.5 | 1.3 | 287 | 0.65 | 442 |
| pMD229 | H272Q | | | | | | | 2.2 | 243 | 0.52 | 472 |
| pMD229 bf | H272Q | | | | | | 1.7 | 1.7 | 355 | 0.60 | 587 |
| pMD229 bf | H272Q | | | | | | | | 378 | 0.63 | 600 |
| pMD229 bf | H272Q | | | | | 3.7 | 1.9 | | 145 | 0.32 | 453 |
| pMD229 | H272Q | | | | | | | | 500 | 0.76 | 656 |

| pMD212 | Mutation | | Na-citr. pH 6.5 | Na-acet. + NaCl | | | | |
|---|---|---|---|---|---|---|---|---|
| ID | 1 | 2 | 85 | 80 | 85 | Betamyl | Phad | B/P |
| pMD212 avg | | | 12.2 | 2.8 | 1.79 | 368 | 0.47 | 794 |
| pMD238 | G188H | Y198W | | 4.0 | 4.09 | 158 | 0.16 | 1018 |
| pMD238 bf | G188H | Y198W | 6.4 | | | 98 | 0.10 | 980 |
| pMD235 | G188T | | 8.5 | 3.3 | 1.26 | 356 | 0.40 | 894 |
| pMD236 | G188H | | 16.1 | 3.8 | 1.29 | 415 | 0.52 | 796 |
| pMD237 | G188S | | | | 1.76 | 380 | 0.49 | 774 |
| pMD237 bf | G188S | | 12.6 | 3.3 | | 255 | 0.28 | 911 |

| pMD230 | Mutation | | | | Na-acet. + NaCl | | | |
|---|---|---|---|---|---|---|---|---|
| ID | 1 | 2 | 3 | 4 | 80 | Beta | Phad | B/P |
| pMD230 avg. | | | | | 2.7 | | | 841 |
| pMD245 | F121D | A161S | P309A | | 0.64 | 443 | 0.63 | 704 |
| pMD257 bf | F121D | A161S | P309A | W339E | 0.31 | 429 | 0.41 | 1046 |
| pMD257 bf | F121D | A161S | P309A | W339E | | 753 | 0.53 | 1429 |
| pMD243 bf | F121D | A161S | W339E | | 0.59 | 382 | 0.38 | 1014 |
| pMD243 bf | F121D | A161S | W339E | | 0.56 | 245 | 0.22 | 1111 |
| pMD249 | F121D | A161S | | | 1.17 | 472 | 0.66 | 720 |
| pMd249 | F121D | A161S | | | 1.12 | 369 | 0.57 | 647 |
| pMD247 | F121D | P309A | | | 0.59 | 501 | 0.69 | 727 |
| pMD246 | A161S | P309A | W339E | | 0.38 | 495 | 0.67 | 738 |
| pMD248 bf | A161S | P309A | | | 0.96 | 351 | 0.87 | 402 |
| pMD248 bf | A161S | P309A | | | 1.07 | 253 | 0.58 | 436 |
| pMD248 bf | A161S | P309A | | | 0.84 | 321 | 0.64 | 502 |
| pMD248 bf | A161S | P309A | | | | 215 | 0.65 | 331 |
| pMD248 bf | A161S | P309A | | | | 18 | 0.09 | 200 |
| pMD248 bf | A161S | P309A | | | | 0 | — | — |
| pMD260 bf | A161S | | | | 2.78 | 381 | 0.64 | 596 |
| pMD244 | P309A | | | | 1.16 | 421 | 0.58 | 726 |

| pMD248 | Mutation | | Na-acet. + NaCl | | | |
|---|---|---|---|---|---|---|
| ID | 1 | 2 | 80 | Beta | Phad | B/P |
| pMD248 avg | | | 0.9 | | | 386 |
| pMD267 | A3T | G70D | 1.5 | 256 | 0.49 | 525 |

TABLE 7-continued

| ID | Mutation 1 | Mutation 2 | | | | | | |
|---|---|---|---|---|---|---|---|---|
| pMD275 | A3S | G70D | | | 1.0 | 164 | 0.20 | 832 |
| pMD265 | A3T | P229S | | | 1.1 | 239 | 0.43 | 555 |
| pMD274 | A3S | P229S | | | 0.8 | 149 | 0.20 | 741 |
| pMD264 | A3T | | | | 1.1 | 205 | 0.42 | 488 |
| pMD266 | A3S | | | | 1.0 | 301 | 0.64 | 472 |
| pMD268 | G70D | | | | 1.3 | 258 | 0.48 | 536 |
| pMD263 | P229S | | | | 1.3 | 209 | 0.33 | 633 |

| pMD253 ID | Mutation 1 | 2 | 3 | 4 | Na-acet. + NaCl 80 | Beta | Phad | B/P |
|---|---|---|---|---|---|---|---|---|
| pMD253 avg. | | | | | 0.8 | | | 441 |
| pMD277 | A3T | G70D | P229S | | 0.6 | 343 | 0.40 | 863 |
| pMD279 | A3S | G70D | P229S | Y227C | 0.6 | 76 | 0.14 | 543 |
| pMD271 | A3S | G70D | | | 0.8 | 420 | 0.76 | 551 |
| pMD271 bf | A3S | G70D | | | 0.9 | 517 | 0.58 | 886 |
| pMD271 bf | A3S | G70D | | | | 609 | 0.98 | 621 |
| pMD270 | A3S | P229S | | | 0.7 | 304 | 0.60 | 506 |
| pMD276 | A3T | P229S | | | 0.7 | 243 | 0.32 | 758 |
| pMD272 | A3T | | | | 0.8 | 160 | 0.35 | 461 |
| pMD278 | A3S | | | | 0.6 | 275 | 0.41 | 678 |
| SSM463 A5 | T67K | | | | 0.5 | 110 | 0.25 | 432 |
| SSM463 E11 | T67V | | | | 0.7 | 303 | 0.69 | 441 |
| SSM463 B11 | T67Q | | | | 0.7 | 314 | 0.84 | 373 |
| SSM463 H11 | T67H | | | | 0.6 | 292 | 1.16 | 251 |
| SSM463 A1 | T67R | | | | 0.7 | 266 | 1.22 | 219 |
| SSM463 A2 | T67G | | | | 0.7 | 199 | 0.69 | 287 |
| SSM463 C7 | T67G | | | | 0.6 | 159 | 0.61 | 263 |
| SSM463 A12 | T67N | | | | 0.6 | 190 | 0.55 | 342 |
| SSM463 A5 | T67K | | | | 0.7 | 510 | 1.80 | 283 |
| SSM464 A7 | G69M | | | | 0.7 | 166 | 0.40 | 415 |
| SSM464 D9 | G69I | | | | 0.5 | 220 | 0.59 | 374 |
| SSM464 C12 | G69H | | | | 0.7 | 154 | 0.54 | 285 |
| SSM464 A3 | G69E | | | | 0.4 | 356 | 0.75 | 473 |
| SSM464 D8 | G69A | | | | 0.6 | 324 | 0.88 | 369 |
| SSM464 C4 | G69R | | | | 0.5 | 177 | 0.78 | 226 |
| SSM464 C10 | G69P | | | | 0.3 | 142 | 0.59 | 239 |
| SSM464 C5 | G69T | | | | 0.6 | 181 | 0.69 | 264 |
| SSM464 A12 | G69K | | | | 0.6 | 700 | 3.64 | 192 |
| SSM464 D8 b | G69A | | | | 0.5 | 254 | 0.81 | 313 |
| pMD273 | G70D | P229S | G74S | | — | 41 | 0.06 | 633 |
| pMD269 | G70D | P229S | | | 1.0 | 339 | 0.61 | 556 |
| SSM465 A11 | S72E | | | | 0.6 | 364 | 0.79 | 460 |
| SSM465 A2 (1) | S72K | | | | 0.6 | 258 | 0.94 | 273 |
| SSM465 A2 (2) | S72K | | | | — | 132 | 0.45 | 293 |
| SSM465 B6 | S72N | | | | 0.7 | 240 | 0.61 | 394 |
| SSM465 D12 | S72T | | | | 0.7 | 252 | 0.65 | 389 |
| SSM465 A2 (2) | S72K | | | | 0.8 | 320 | 1.08 | 295 |
| SSM466 A1 | G73M | | | | 0.7 | 96 | 0.31 | 313 |
| SSM466 B8 | G73S | | | | 0.5 | 69 | 0.22 | 309 |
| SSM466 A4 | G73T | | | | 0.4 | 76 | 0.26 | 290 |
| SSM466 A3 | G73N | | | | 0.5 | 97 | 0.26 | 368 |
| SSM466 C7 | G73L | | | | — | 88 | 0.30 | 289 |
| SSM466 A8 | G73E | | | | 0.6 | 119 | 0.60 | 197 |
| SSM466 B5 | G73D | | | | — | 24 | 0.21 | 116 |
| SSM466 A1 | G73M | | | | 0.8 | 419 | 1.49 | 281 |
| SSM466 B8 | G73S | | | | 0.6 | 336 | 1.03 | 327 |
| SSM466 A4 | G73T | | | | 0.5 | 229 | 0.73 | 313 |
| SSM466 A3 | G73N | | | | 0.5 | 331 | 0.89 | 371 |
| SSM466 C7 | G73L | | | | 0.8 | 211 | 0.70 | 300 |
| SSM467 D3 | G75C | | | | 0.6 | 100 | 0.19 | 531 |
| SSM467 C10 | G75S | | | | 0.2 | 332 | 0.78 | 423 |
| SSM467 F6 | G75R | | | | 0.0 | 258 | 1.16 | 223 |
| SSM467 A9 | G75Y | | | | 0.0 | 269 | 0.87 | 310 |
| SSM467 F12 | G75S | | | | 0.3 | 260 | 0.62 | 419 |
| SSM467 C12 (1) | G75F | | | | 0.0 | 235 | 0.59 | 401 |
| SSM467 A10 | G75W | | | | 0.0 | 275 | 0.76 | 363 |
| SSM467 C12 (2) | G75F | | | | 0.0 | 221 | 0.64 | 345 |
| SSM467 G10 | G75E | | | | 0.6 | 299 | 0.51 | 582 |
| SSM467 D3 | G75C | | | | 0.4 | 379 | 0.91 | 417 |

| pMS281 ID | Mutation 1 | 2 | 3 | 4 | Na-acet. + NaCl 80 | Beta | Phad | B/P |
|---|---|---|---|---|---|---|---|---|
| pMS281 avg. | | | | | 2.0 | | | 1045 |
| pMS302 | A161S | Q169D | P229S | | 0.7 | 310 | 0.31 | 993 |

TABLE 7-continued

| ID | 1 | 2 | 3 | 4 | 5/6/7 | 80 | Beta | Phad | B/P |
|---|---|---|---|---|---|---|---|---|---|
| pMS303 | A161S | Q169D | P229S | Q272H | | 0.9 | 466 | 0.60 | 778 |
| pMS300 | A161S | Q272H | | | | 1.4 | 120 | 0.08 | 1474 |
| pMS300 bf | A161S | Q272H | | | | | 249 | 0.51 | 488 |
| pMS299 | Q169D | P229S | | | | 1.1 | 408 | 0.23 | 1771 |
| pMS299 bf | Q169D | P229S | | | | 1.1 | 198 | 0.11 | 1840 |
| pMS310 | P229S | Q272H | | | | 1.4 | 190 | 0.16 | 1194 |
| pMS301 | P229S | | | | | 1.5 | 123 | 0.22 | 555 |
| pMS301 bf | P229S | | | | | | 344 | 0.29 | 1196 |
| pMS309 | Q272H | | | | | 1.7 | 229 | 0.19 | 1182 |

| pMS284 ID | Mutation | | | | | Na-acet. + NaCl | | | |
|---|---|---|---|---|---|---|---|---|---|
| | 1 | 2 | 3 | 4 | 5/6/7 | 80 | Beta | Phad | B/P |
| pMS284 avg. | | | | | | 1.0 | 363 | 0.74 | 489 |
| pMS422 | Y33N | G70D | Q272H | E303G | L307K | 2.4 | 132 | 0.49 | 271 |
| pMS423 | N34D | G70D | Q272H | E303G | L307K | 2.1 | 132 | 0.46 | 288 |
| pMS363 | D68C | N145D | G158T | L307K | | | 23 | 0.11 | 209 |
| pMS352 | D68C | N145D | L307R | | | | 59 | 0.12 | 492 |
| pMS367 | D68C | N145D | L307K | | | | 58 | 0.14 | 414 |
| pMS365 | D68C | G158T | E303G | L307K | | | 16 | 0.25 | 64 |
| pMS351 bf | D68C | G158T | L307R | | | | 43 | 0.26 | 163 |
| pMS360 | D68C | E303G | L307K | | | | 56 | 0.33 | 170 |
| pMS354 | D68C | L307R | | | | | 30 | 0.09 | 333 |
| pMS357 | D68C | L307R | | | | | 41 | 0.10 | 410 |
| pMS359 | D68C | L307K | | | | | 71 | 0.21 | 338 |
| pMS362 | D68C | L307K | | | | | 50 | 0.16 | 313 |
| pMS434 OS21 | G70D | E76V | E223G | Q272H | E303G/ L307K | — | 9 | 0.03 | 286 |
| pMS442 | G70D | F121G | A161S | E223G | Q272H/ E303G/ L307K | 0.6 | 148 | 3.34 | 44 |
| pMS444 | G70D | F121G | A161S | Q272H | E303G/ L307K | 0.8 | 139 | 2.93 | 47 |
| pMS445 | G70D | F121G | E223G | Q272H | E303G/ L307K | 0.7 | 148 | 1.61 | 92 |
| pMS425 | G70D | F121G | Q272H | E303G | L307K | 0.8 | 108 | 0.70 | 155 |
| pMS421 | G70D | P141A | Q272H | E303G | L307K | 0.7 | 95 | 0.33 | 288 |
| pMS426 | G70D | N145D | G146Y | Q272H | E303G/ L307K | 0.8 | 124 | 0.41 | 301 |
| pMS402 | G70D | N145D | A161T | E303G | L307H | | 103 | 0.61 | 169 |
| pMS406 | G70K | N145D | A161S | L163M | E303G/ L307R | 1.2 | 99 | 0.65 | 152 |
| pMS402 bf | G70D | N145D | A161T | E303G | L307H | 2.9 | 666 | 4.00 | 166 |
| pMS411 | G70K | D145N | A161S | E303G | | 1.7 | 126 | 1.52 | 83 |
| pMS412 | G70K | N145D | A161S | E303G | L307H | 2.0 | 180 | 1.71 | 105 |
| pMS402 bf | G70D | N145D | A161T | E303G | L307H | | 566 | 3.09 | 183 |
| pMS415 | G70D | N145D | A161S | E303G | L307H | 2.5 | 159 | 0.67 | 237 |
| pMS388 | G70D | N145D | Y198W | E303G | L307K | | 24 | 0.09 | 267 |
| pMS393 | G70D | N145D | Y198W | E303G | L307K | 3.2 | 21 | 0.09 | 233 |
| pMS380 | G70D | N145D | Q272H | E303G | L307K | 2.7 | 481 | 2.13 | 226 |
| pMS383 | G70K | N145D | Q272H | E303G | L307K | 2.2 | 407 | 2.66 | 153 |
| pMS375 | G70D | N145D | E303G | L307K | | 2.1 | 545 | 2.03 | 268 |
| pMS384 | G70K | N145D | E303G | L307K | | 2.4 | 460 | 2.88 | 160 |
| pMS381 bf | G70K | N145D | E303G | L307K | | 2.9 | 471 | 3.53 | 133 |
| pMS387 | G70D | N145D | E303G | L307K | | 3.7 | 125 | 0.40 | 313 |
| pMS390 | G70K | N145D | E303G | L307K | | 3.2 | 112 | 0.63 | 178 |
| pMS396 | G70D | N145D | E303G | L307H | | 1.7 | 214 | 0.54 | 396 |
| pMS390 bf | G70K | N145D | E303G | L307K | | | 424 | 2.49 | 170 |
| pMS390 bf | G70K | N145D | E303G | L307K | | | 349 | 2.23 | 157 |
| pMS410 | G70K | D145N | E303G | N302K | | 1.7 | 126 | 1.25 | 101 |
| pMS410 (b) | G70K | D145N | E303G | N302K | | | 72 | 0.56 | 129 |
| pMS396 bf | G70D | N145D | E303G | L307H | | | 963 | 3.11 | 310 |
| pMS413 bf | G70K | N145D | E303G | L307H | 1bpdel | | 4 | 0.01 | 440 |
| pMS396 bf | G70D | N145D | E303G | L307H | | | 650 | 1.91 | 340 |
| pMS439 | G70D | G146Y | Q272H | E303G | L307K | | 68 | 0.66 | 103 |
| pMS433 OS21 | G70D | L157I | Q272H | E303G | L307K | 0.9 | 132 | 0.37 | 357 |
| pMS443 | G70D | A161S | E223G | Q272H | E303G/ L307K | 1.4 | 116 | 1.62 | 72 |
| pMS427 | G70D | A161S | Q272H | E303G | L307K | 1.8 | 103 | 0.85 | 121 |
| pMS398 | G70K | A161S | E303G | L307K | | | 60 | 1.17 | 51 |
| pMS399 | G70K | A161S | E303G | L307H | | 1.3 | 140 | 1.61 | 87 |
| pMS401 | G70K | A161S | E303G | L307H | | 1.4 | 128 | 1.57 | 82 |
| pMS401 bf | G70K | A161S | E303G | L307H | | 1.4 | 752 | 8.73 | 86 |
| pMS428 | G70D | F178L | Q272H | E303G | L307K | 1.1 | 102 | 0.34 | 303 |
| pMS429 | G70D | T179A | Q272H | E303G | L307K | 2.1 | 111 | 0.38 | 296 |
| pMS395 | G70D | Y198W | E303G | L307H | | | 48 | 0.16 | 300 |
| pMS438 | G70D | E223G | Q272H | E303G | L307K | | 74 | 0.70 | 106 |
| pMS446 | G70D | E223G | Q272H | E303G | L307K | | 97 | 0.45 | 214 |

TABLE 7-continued

| | | | | | | | | | |
|---|---|---|---|---|---|---|---|---|---|
| pMS430 | G70D | P229S | Q272H | E303G | L307K | 2.0 | 113 | 0.32 | 353 |
| pMS437 OS21 | G70D | V267I | Q272H | E303G | L307K | 2.0 | 124 | 0.38 | 326 |
| pMS382 | G70D | Q272H | E303G | L307K | | 2.1 | 100 | 0.54 | 185 |
| pMS382 bf | G70D | Q272H | E303G | L307K | | | 295 | 1.84 | 160 |
| pMS382 bf | G70D | Q272H | E303G | L307K | | 2.1 | 442 | 2.64 | 167 |
| pMS382 bf | G70D | Q272H | E303G | L307K | | 2.1 | 421 | 2.84 | 148 |
| pMS382 bf | G70D | Q272H | E303G | L307K | | | 410 | 2.66 | 154 |
| pMS382 bf | G70D | Q272H | E303G | L307K | | | 333 | 1.97 | 169 |
| pMS431 | G70D | Q272H | E303G | L307K | P334S | 0.8 | 97 | 0.26 | 373 |
| pMS432 | G70D | Q272H | E303G | L307H | | 2.7 | 238 | 0.65 | 366 |
| pMS382 bf; kontrolprøve | G70D | Q272H | E303G | L307K | | 2.2 | 470 | 2.28 | 206 |
| pMS435 OS21 | G70D | Q272H | E303G | L307K | | 2.0 | 104 | 0.36 | 290 |
| pMS436 OS21 | G70D | Q272H | E303G | P309A | | 1.2 | 221 | 0.60 | 368 |
| pMS441 | G70D | Q272H | E303G | L307K | P309A | | 63 | 0.43 | 147 |
| pMS432 | G70D | Q272H | E303G | L307H | | | 231 | 0.91 | 254 |
| pMS435 | G70D | Q272H | E303G | L307K | | | 132 | 0.65 | 203 |
| pMS435 | G70D | Q272H | E303G | L307K | | | 110 | 0.59 | 186 |
| pMS391 bf | G70K | E303G | L307K | | | 1.6 | 321 | 2.43 | 132 |
| pMS403 | G70K | E303G | L307R | | | 2.0 | 85 | 0.39 | 218 |
| pMS418 | G70D | E303G | L307H | | | 1.7 | 160 | 1.18 | 136 |
| SSM474 A02 | G70K | | | | | | 305 | 0.64 | 477 |
| SSM474 A03 | G70G | | | | | | 278 | 0.51 | 545 |
| SSM474 B01 | G70E | | | | | | 330 | 0.47 | 702 |
| SSM474 C05 | G70S | | | | | | 70 | 0.18 | 384 |
| SSM474 D04 | G70G | | | | | | 187 | 0.46 | 407 |
| SSM474 D10 | G70G | | | | | | 105 | 0.25 | 425 |
| SSM474 E06 | G70Q | | | | | | 131 | 0.35 | 373 |
| SSM474 E09 | G70A | | | | | | 125 | 0.32 | 393 |
| SSM474 G02 | G70S | | | | | | 130 | 0.31 | 424 |
| SSM474 G11 | G70V | | | | | | 160 | 0.40 | 401 |
| SSM474 H02 | G70L | | | | | | 204 | 0.38 | 537 |
| SSM474 B06 | G70P | | | | | | 106 | 0.25 | 432 |
| SSM474 C03 | G70D | | | | | | 85 | 0.18 | 465 |
| pMS368 | N145D | G158T | L307K | | | | 78 | 0.26 | 300 |
| pMS368 bf | N145D | G158T | L307K | | | | 288 | 0.94 | 306 |
| pMS368 bf | N145D | G158T | L307K | | | 1.8 | 243 | 0.78 | 312 |
| pMS405 | N145D | A161S | E303G | L307R | | 2.7 | 89 | 0.50 | 178 |
| pMS405 bf | N145D | A161S | E303G | L307R | | 3.2 | 525 | 3.27 | 160 |
| pMS409 | D145N | A161S | E303G | Q305L | | 1.6 | 107 | 0.91 | 118 |
| pMS416 | D145N | A161S | E303G | | | 1.9 | 130 | 0.48 | 270 |
| pMS386 | N145D | Y198W | G70K | E303G | L307K | | 19 | 0.18 | 106 |
| pMS372 bf | N145D | Y198W | E303G | L307K | | 3.2 | 510 | 2.48 | 206 |
| pMS358 | N145D | E303G | L307K | | | | 134 | 1.71 | 79 |
| pMS364 | N145D | E303G | L307K | | | | 173 | 0.59 | 293 |
| pMS364 bf | N145D | E303G | L307K | | | 2.2 | 483 | 1.54 | 314 |
| pMS364 bf | N145D | E303G | L307K | | | 2.4 | 470 | 1.31 | 359 |
| pMS364 bf | N145D | E303G | L307K | | | 2.5 | 364 | 1.80 | 202 |
| pMS376 | N145D | E303G | L307H | | | 2.1 | 894 | 3.40 | 263 |
| pMS379 | N145D | E303G | L307H | | | 2.2 | 1064 | 4.42 | 241 |
| pMS385 | N145D | E303G | L307K | | | 2.5 | 471 | 2.50 | 188 |
| pMS389 | N145D | E303G | L307K | | | 3.6 | 110 | 0.34 | 324 |
| pMS392 | N145D | E303G | L307K | | | 3.1 | 100 | 0.42 | 238 |
| pMS397 | N145D | E303G | L307H | | | 1.5 | 204 | 0.61 | 334 |
| pMS389 bf | N145D | E303G | L307K | | | | 410 | 1.43 | 287 |
| pMS414 | N145D | E303G | L307R | | | 3.2 | 113 | 0.32 | 353 |
| pMS389 bf | N145D | E303G | L307K | | | | 461 | 1.75 | 263 |
| pMS389 bf | N145D | E303G | L307K | | | | 326 | 0.96 | 340 |
| pMS407 | D145N | E303G | | | | 2.1 | 169 | 0.76 | 222 |
| pMS353 | N145D | L307R | | | | | 135 | 0.21 | 643 |
| pMS355 bf | N145D | L307R | | | | | 417 | 0.58 | 719 |
| pMS361 | N145D | L307K | | | | | 146 | 0.26 | 562 |
| pMS408 | D145N | | | | | 1.5 | 72 | 0.16 | 450 |
| SSM475 A01 | G158G | | | | | | 195 | 0.37 | 533 |
| SSM475 A02 | G158F | | | | | | 131 | 0.34 | 381 |
| SSM475 A03 | G158G | | | | | | 292 | 0.54 | 541 |
| SSM475 B01 | G158P | | | | | | 24 | 0.51 | 46 |
| SSM475 B02 | G158I | | | | | | 72 | 0.35 | 204 |
| SSM475 B04 | G158A | | | | | | 58 | 0.13 | 448 |
| SSM475 B06 | G158T | | | | | | 65 | 0.18 | 357 |
| SSM475 D04 | G158V | | | | | | 121 | 0.36 | 335 |
| SSM475 E04 | G158L | | | | | | 67 | 0.21 | 326 |
| SSM475 F02 | G158Q | | | | | | 115 | 0.29 | 392 |
| SSM475 F03 | G158C | | | | | | 28 | 0.05 | 520 |
| SSM475 G02 | G158S | | | | | | 78 | 0.20 | 401 |
| pMS400 | A161S | E303G | L307H | | | 1.4 | 142 | 1.37 | 104 |
| pMS404 | A161S | E303G | L307R | | | 1.6 | 59 | 0.60 | 98 |
| pMS400 bf | A161S | E303G | L307H | | | 1.5 | 788 | 8.62 | 91 |
| SSM470 A01 | A161A | | | | | | 215 | 0.41 | 524 |
| SSM470 A03 | A161K | | | | | | 92 | 0.86 | 106 |

TABLE 7-continued

| ID | Mut1 | Mut2 | Mut3 | Mut4 | Na-acet.+NaCl 80 | Beta | Phad | B/P |
|---|---|---|---|---|---|---|---|---|
| SSM470 A04 | A161P | | | | | 154 | 0.77 | 201 |
| SSM470 C06 | A161G | | | | | 192 | 0.68 | 283 |
| SSM470 F03 | A161R | | | | | 76 | 0.79 | 96 |
| SSM470 G11 | A161H | | | | | 121 | 1.92 | 63 |
| pMS298 | Q169D | | | | | 213 | 0.36 | 592 |
| pMS328 | W232F | | | | | 65 | 0.13 | 500 |
| pMS329 | W232G | | | | | 46 | 0.09 | 512 |
| pMS330 | W232H | | | | | 55 | 0.11 | 521 |
| pMS331 | W232I | | | | | 52 | 0.10 | 515 |
| pMS332 | W232K | | | | | 64 | 0.15 | 439 |
| pMS333 | W232L | | | | | 62 | 0.12 | 521 |
| pMS335 | W232N | | | | | 80 | 0.14 | 549 |
| pMS336 | W232P | | | | | 1 | 0.01 | 180 |
| pMS337 | W232Q | | | | | 100 | 0.17 | 597 |
| pMS338 | W232R | | | | | 60 | 0.14 | 438 |
| pMS339 | W232S | | | | | 107 | 0.19 | 553 |
| pMS341 | W232Y | | | | | 103 | 0.21 | 492 |
| pMS340 | W232T | | | | | 184 | 0.31 | 594 |
| pMS424 | Q272H | E303G | L307K | | 1.9 | 103 | 0.54 | 188 |
| pMS369 | Q272H | L307K | | | 1.0 | 374 | 0.92 | 407 |
| pMS356 bf | E303G | L307R | | | | 442 | 1.83 | 241 |
| pMS366 | E303G | L307K | | | | 156 | 0.82 | 190 |
| pMS366 bf | E303G | L307K | | | 1.4 | 367 | 1.91 | 192 |
| pMS366 bf | E303G | L307K | | | | 506 | 2.28 | 222 |
| pMS356 bf | E303G | L307R | | | 1.3 | 452 | 1.39 | 325 |
| pMS366 bf | E303G | L307K | | | 1.5 | 335 | 1.38 | 243 |
| pMS366 bf | E303G | L307K | | | 1.6 | 375 | 2.10 | 179 |
| pMS394 | E303G | L307H | | | 1.4 | 244 | 0.89 | 274 |
| pMS366 bf | E303G | L307K | | | 2.1 | 336 | 2.09 | 161 |
| SSM471 A01 | L307L | | | | | 240 | 0.55 | 439 |
| SSM471 B10 | L307R | | | | | 132 | 0.20 | 660 |
| SSM471 C04 | L307K | | | | | 108 | 0.24 | 456 |
| SSM471 C07 | L307G | | | | | 301 | 0.40 | 747 |
| SSM471 E02 | L307P | | | | | 74 | 0.02 | 3510 |
| SSM471 E04 | L307I | | | | | 250 | 0.48 | 521 |
| SSM471 E12 | L307S | | | | | 257 | 0.48 | 536 |
| SSM471 F01 | L307R | | | | | 71 | 0.03 | 2629 |
| SSM471 H07 | L307M | | | | | 266 | 0.50 | 538 |
| SSM471 C04 | L307K | | | | | 106 | 0.2 | 461 |
| SSM471 C04 bf | L307K | | | | | 288 | 0.6 | 450 |
| SSM471 C04 bf | L307K | | | | | 372 | ND | ND |
| SSM471 C04 bf | L307K | | | | | 315 | 0.80 | 392 |
| pMS343 | L307K | | | | | 32 | 0.11 | 291 |
| pMS344 | L307Q | | | | | 72 | 0.22 | 327 |
| pMS345 | L307V | | | | | 70 | 0.21 | 333 |
| pMS346 | L307W | | | | | 180 | 0.62 | 290 |
| pMS347 | L307Y | | | | | 179 | 0.47 | 381 |
| pMS348 | L307C | | | | | 31 | 0.09 | 344 |
| pMS349 | L307F | | | | | 50 | 0.13 | 385 |
| SSM471 B10 bf | L307R | | | | 0.8 | 384 | 0.72 | 537 |
| SSM471 C04 bf | L307K | | | | 1.0 | 268 | 0.79 | 339 |
| pMS370 bf | L307H | | | | 0.5 | 730 | 1.67 | 437 |
| pMS371 | L307E | | | | 0.4 | 288 | 0.61 | 472 |
| SSM472 A01 | W308W | | | | | 318 | 0.56 | 572 |
| SSM472 B06 | W308N | | | | | 60 | 0.15 | 395 |
| SSM472 B09 | W308R | | | | | 62 | 0.10 | 592 |
| SSM472 E07 | W308T | | | | | 97 | 0.17 | 577 |
| SSM472 G03 | W308S | | | | | 119 | 0.19 | 630 |
| SSM472 G05 | W308G | | | | | 168 | 0.15 | 1104 |
| SSM472 G07 | W308Q | | | | | 168 | 0.23 | 725 |
| SSM472 H12 | W308A | | | | | 226 | 0.26 | 884 |
| pMS334 | W323M | | | | | 53 | 0.09 | 606 |
| SSM473 A04 | P334P | | | | | 136 | 0.26 | 523 |
| SSM473 A06 | P334Q | | | | | 105 | 0.19 | 565 |
| SSM473 B08 | P334T | | | | | 74 | 0.15 | 498 |
| SSM473 B11 | P334H | | | | | 72 | 0.11 | 642 |
| SSM473 C02 | P334T | | | | | 85 | 0.16 | 525 |
| SSM473 C11 | P334S | | | | | 116 | 0.26 | 441 |
| SSM473 C12 | P334A | | | | | 134 | 0.24 | 558 |
| SSM473 D03 | P334K | | | | | 61 | 0.12 | 499 |
| SSM473 D04 | P334M | | | | | 79 | 0.14 | 568 |
| SSM473 H07 | P334L | | | | | 65 | 0.15 | 432 |

| pMS292 ID | Mutation 1 | Mutation 2 | Mutation 3 | Mutation 4 | Na-acet.+NaCl 80 | Beta | Phad | B/P |
|---|---|---|---|---|---|---|---|---|
| pMS292 avg. | | | | | 4.1 | | | 547 |
| pMS317 | N34D | A161S | Q169D | | 1.5 | 275 | 0.57 | 482 |

TABLE 7-continued

| pMS ID | Mutation 1 | Mutation 2 | Mutation 3 | Mutation 4 | Na-acet. + NaCl 80 | Beta | Phad | B/P |
|---|---|---|---|---|---|---|---|---|
| pMS311 | N34D | A161S | Q272H | | 2.8 | 266 | 0.89 | 299 |
| pMS316 | N34D | P229S | Q272H | | 4.3 | 294 | 0.56 | 525 |
| pMS321 | N34D | Q272H | | | 3.0 | 311 | 0.44 | 707 |
| pMS324 | D149H | | | | 0.7 | 310 | 1.04 | 297 |
| pMS304 | A161S | Q169D | P229S | Q272H | 1.6 | 443 | 1.23 | 360 |
| pMS306 | A161S | Q169D | P229S | | 1.6 | 454 | 0.94 | 485 |
| pMS313 | A161S | Q169D | P229S | Q272H | 1.4 | 250 | 0.85 | 294 |
| pMS305 | Q169D | P229S | Q272H | | 1.7 | 534 | 0.78 | 684 |
| pMS322 | Q169D | P229S | Q272H | G276R | 0.0 | 15 | 0.05 | 300 |
| pMS308 | Q169D | P229S | | | 1.8 | 453 | 0.57 | 795 |
| pMS319 | Q169D | | | | 1.8 | 461 | 0.68 | 678 |
| pMS307 | P229S | Q272H | | | 2.8 | 170 | 0.29 | 578 |
| pMS318 | P229S | Q272H | | | 3.6 | 329 | 0.80 | 411 |
| pMS315 | P229S | | | | 3.0 | 230 | 0.52 | 442 |
| pMS320 | Q272H | | | | 4.0 | 467 | 1.34 | 349 |

| pMS382 ID | Mutation 1 | Na-acet. + NaCl 80 | Beta | Phad | B/P |
|---|---|---|---|---|---|
| pMS382 avg. | | 2.1 | | | 170 |
| pMS454 | E223E | 2.1 | 181 | 0.9 | 212 |
| pMS455 | E223I | 1.2 | 170 | 0.8 | 220 |
| pMS456 | E223L | 1.4 | 152 | 0.6 | 238 |
| pMS457 | E223V | 1.4 | 101 | 0.7 | 140 |
| pMS458 | E223F | 1.6 | 197 | 0.6 | 346 |
| pMS459 | E223E | 2.0 | 152 | 0.7 | 220 |
| pMS460 | E223C | 1.6 | 75 | 0.1 | 682 |
| pMS461 | E223A | 2.2 | 177 | 1.1 | 167 |
| pMS462 | E223G | 1.5 | 109 | 0.7 | 147 |
| pMS463 | E223P | 1.8 | 205 | 0.6 | 353 |
| pMS464 | E223T | 1.5 | 231 | 0.7 | 325 |
| pMS465 | E223S | 2.1 | 254 | 1.7 | 149 |
| pMS466 | E223Y | 1.4 | 148 | 0.7 | 205 |
| pMS467 | E223W | 1.6 | 130 | 0.4 | 361 |
| pMS468 | E223Q | 1.9 | 204 | 0.9 | 217 |
| pMS469 | E223N | 2.1 | 225 | 1.1 | 199 |
| pMS470 | E223D | 2.3 | 209 | 1.1 | 192 |
| pMS471 | E223H | 1.8 | 160 | 0.7 | 232 |
| pMS472 | E223K | 1.8 | 142 | 0.3 | 414 |
| pMS473 | E223R | 1.8 | 122 | 0.5 | 263 |
| pMS474 | E223M | 1.7 | 154 | 0.6 | 269 |

What is claimed is:

1. A method of processing starch comprising liquefying a starch and/or saccharifying a starch liquefact to form a saccharide syrup by adding a *Pseudomonas saccharophila* amylase (PS4) variant having amylase activity, wherein said variant comprises a polypeptide sequence which is:
   (a) SEQ ID NO: 1;
   (b) SEQ ID NO: 2;
   (c) residues 1 to 429 of SEQ ID NO: 1;
   (d) a polypeptide sequence having at least 90% sequence identity to SEQ ID NO: 1;
   (e) a polypeptide sequence having at least 90% sequence identity to SEQ ID NO: 2; or
   (f) a polypeptide sequence having at least 90% sequence identity to residues 1 to 429 of SEQ ID NO: 1,
   whereby saccharide syrup is formed.

2. The method of claim 1, wherein the PS4 variant comprises a polypeptide sequence having at least 95% sequence identity to:
   (a) SEQ ID NO: 1;
   (b) SEQ ID NO: 2; or
   (c) residues 1 to 429 of SEQ ID NO: 1.

3. The method of claim 1, wherein the PS4 variant comprises one or more substitutions corresponding to substitutions at positions in SEQ ID NO:1 selected from the group consisting of A3T, A8N, I38M, I46F, G104R, G158P, S161H, Q169R, G188A, P200A/G, S213N, T324L, and D422N.

4. The method of claim 1, wherein the PS4 variant comprises an amino acid sequence that has up to 25 amino acid deletions, additions, insertions, or substitutions compared to the amino acid sequence of SEQ ID NO: 1, residues 1 to 429 of SEQ ID NO: 1, or SEQ ID NO: 2.

5. The method of claim 1, wherein the PS4 variant has an altered thermostability compared to the protein of SEQ ID NO: 1, the fragment of the protein of SEQ ID NO:1 consisting of residues 1 to 429, or the protein of SEQ ID NO: 2.

6. The method of claim 5, wherein the PS4 variant is more thermostable than the protein of SEQ ID NO: 1, the fragment of the protein of SEQ ID NO:1 consisting of residues 1 to 429, or the protein of SEQ ID NO: 2.

7. The method of claim 1, wherein the PS4 variant has an altered endo-amylase activity, an altered exo-amylase activity, and/or an altered ratio of exo- to endo-amylase activity compared to the protein of SEQ ID NO: 1, the fragment of the protein of SEQ ID NO:1 consisting of residues 1 to 429, or the protein of SEQ ID NO: 2.

8. The method of claim 7, wherein the PS4 variant has an increased endo-amylase activity or a decreased ratio of exo- to endo-amylase activity compared to the protein of SEQ ID NO: 1, the fragment of the protein of SEQ ID NO:1 consisting of residues 1 to 429, or the protein of SEQ ID NO: 2.

9. The method of claim 7, wherein the PS4 variant has an increased exo-amylase activity or an increased ratio of exo- to endo-amylase activity compared to the protein of SEQ ID NO: 1, the fragment of the protein of SEQ ID NO: 1 consisting of residues 1 to 429 of SEQ ID NO: 1, or the protein of SEQ ID NO: 2.

10. The method of claim 1 further comprising adding a debranching enzyme, an isoamylase, a pullulanase, a protease, a cellulase, a hemicellulase, a lipase, a cutinase, or any combination of said enzymes, to the starch liquefact.

11. The method of claim 1, wherein the starch is from corns, cobs, wheat, barley, rye, milo, sago, cassava, tapioca, sorghum, rice, peas, bean, banana, or potatoes.

12. The method of claim 1 further comprising fermenting the saccharide syrup to produce ethanol.

13. The method of claim 12 further comprising recovering the ethanol.

14. The method of claim 13 further comprising distilling the starch to obtain the ethanol, wherein the fermenting and the distilling are carried out simultaneously, separately, or sequentially.

15. The method of claim 1, wherein the PS4 variant comprises one or more amino acid substitutions at positions corresponding to positions 8, 38, 104, 169, 200, 324 of SEQ ID NO: 1.

16. The method of claim 15, wherein the PS4 variant comprises one or more amino acid substitutions corresponding to substitutions in SEQ ID NO:1 selected from the group consisting of A8N, I38M, G104R, Q169R, P200A/G, and T324L.

17. The method of claim 16, wherein the amino acid substitution is a substitution corresponding to substitution P200A in SEQ ID NO: 1.

18. The method of claim 16, wherein the amino acid substitution is a substitution corresponding to substitution P200G in SEQ ID NO: 1.

* * * * *